US005641847A

United States Patent [19]
Hozumi et al.

[11] Patent Number: 5,641,847
[45] Date of Patent: Jun. 24, 1997

[54] OIL-ABSORBENT POLYMER AND USE THEREFOR

[75] Inventors: Yoshiyuki Hozumi; Toru Inaoka; Tomoki Gomi; Takakiyo Goto; Toru Uno; Kenji Rakutani, all of Yokohama, Japan

[73] Assignee: Nippon Shokubai Kagaku Kogyo Co., Ltd., Osaka, Japan

[21] Appl. No.: 579,888

[22] Filed: Dec. 28, 1995

Related U.S. Application Data

[62] Division of Ser. No. 285,429, Aug. 1, 1994, abandoned, which is a division of Ser. No. 126,731, Sep. 27, 1993, Pat. No. 5,374,600, which is a continuation of Ser. No. 647,064, Jan. 29, 1991, abandoned.

[30] Foreign Application Priority Data

| Jan. 29, 1990 | [JP] | Japan | 2-15994 |
| Feb. 16, 1990 | [JP] | Japan | 2-33635 |
| Mar. 22, 1990 | [JP] | Japan | 2-69797 |
| Apr. 4, 1990 | [JP] | Japan | 2-88131 |
| Apr. 13, 1990 | [JP] | Japan | 2-96537 |
| May 9, 1990 | [JP] | Japan | 2-117705 |
| Jun. 8, 1990 | [JP] | Japan | 2-148669 |
| Jun. 8, 1990 | [JP] | Japan | 2-148670 |
| Jun. 20, 1990 | [JP] | Japan | 2-159923 |
| Jun. 20, 1990 | [JP] | Japan | 2-159924 |
| Aug. 3, 1990 | [JP] | Japan | 2-205100 |
| Aug. 3, 1990 | [JP] | Japan | 2-205101 |
| Oct. 8, 1990 | [JP] | Japan | 2-270097 |
| Oct. 22, 1990 | [JP] | Japan | 2-285094 |
| Nov. 29, 1990 | [JP] | Japan | 2-336268 |
| Nov. 29, 1990 | [JP] | Japan | 2-336269 |

[51] Int. Cl.$^6$ .................. C08F 220/10; C08K 5/01; C08K 5/05; C08K 5/07; C08K 5/10
[52] U.S. Cl. .................. 526/328.5; 524/379; 524/356; 524/284
[58] Field of Search .................. 526/328.5; 524/284, 524/356, 379

[56] References Cited

U.S. PATENT DOCUMENTS

| 3,720,534 | 3/1973 | Macaulay et al. | 526/328.5 |
| 3,819,514 | 6/1974 | Clampitt et al. | 210/40 |
| 4,497,710 | 2/1985 | Wagu et al. | 210/635 |
| 4,812,319 | 3/1989 | Hsu et al. | 426/127 |
| 4,940,578 | 7/1990 | Yoshihara et al. | 424/70 |

FOREIGN PATENT DOCUMENTS

| 0441512A2 | 8/1991 | European Pat. Off. . |
| 0441512A3 | 8/1991 | European Pat. Off. . |
| 2153358 | 5/1973 | France . |
| 2513895 | 4/1983 | France . |
| 45-27081 | 9/1970 | Japan . |
| 50-15882 | 2/1975 | Japan . |
| 50-59486 | 5/1975 | Japan . |
| 4-15286 | 1/1992 | Japan . |
| 4-41583 | 2/1992 | Japan . |
| 5209017 | 8/1993 | Japan . |
| 1191141 | 5/1970 | United Kingdom . |

*Primary Examiner*—Joseph L. Schofer
*Assistant Examiner*—Wu C. Cheng
*Attorney, Agent, or Firm*—Burns, Doane, Swecker & Mathis, LLP

[57] ABSTRACT

A swellable oil-absorbent agent formed of a cross-linked polymer (P) obtained by polymerizing a monomer component comprising 90 to 99.999% by weight of a monomer having as a main moiety thereof an alkyl (meth)acrylate the alkyl group of which has 10 to 16 carbon atoms and possessing one polymerizable unsaturated group in the molecular unit thereof and 0.001 to 10% by weight of a cross-linkable monomer possessing at least two polymerizable unsaturated groups in the molecular unit thereof (providing that the total of the amount of the polymerizable monomer and that of the cross-linkable monomer is 100% by weight).

14 Claims, No Drawings

OIL-ABSORBENT POLYMER AND USE THEREFOR

This application is a divisional of application No. 08/285,429, filed Aug. 1, 1994, abandoned which is a divisional of application No. 08/126,731, filed Sep. 27, 1993, U.S. Pat. No. 5,374,600 which is a continuation of application No. 07/647,064, filed Jan. 29, 1991, abandoned.

BACKGROUND OF THE INVENTION

1. Field of the Invention

This invention relates to an oil-absorbent polymer and uses found therefor. More specifically, relates to a swelling absorbent for oil which swells by efficiently absorbent oil and exhibits a markedly improved oil-absorbent capacity at low temperatures, uses found therefor such as, for example, substrate for gradual release of aquatic chemical agents, gelled aromatic composition, gelled insectifugal, insecticidal, and fungicidal compositions, aquatic antifouling composition, fish-luring composition, solid fuel composition, oil absorbent material, oil mist filter, oil sealing material, paper excellent in printability, thermosensitive recording material, and pressure sensitive recording sheet, a method for the production of an oil-absorbent material, and a method for the removal of oil dissolved in water.

2. Description of the Prior Art

In recent years, the recovery of oil from the sea contaminated by accidentally effused oil and from the oil-containing waste water has come to constitute itself a serious problem in terms of environmental control. The desirability of the debut of a method for convenient disposal of spent oils discarded in small amounts from homes and plants and machine oils and other oils leaking from plants has been finding earnest recognition.

As one of the dominant means for the recovery of accidentally effused oil or oil entrained by waste water or for the disposal of spent oil or leaking oil, the procedure which comprises causing an absorbent for oil to absorb the unwanted oil and then subjecting the oil-impregnated absorbent to incineration or some other similar after-treatment has been heretofore adoped. The commercially available absorbents for oil which are effectively usable in this procedure include natural plant type oil absorbents such as rice hulls, straw, pulp, peat, and cotton; inorganic type oil absorbents produced by subjecting inorganic porous powders of lime, silica, and pearlite to a treatment for impartation of water repellency; synthetic fiber type oil absorbents using polypropylene fibers, polystyrene fibers, and polyurethane fibers; and foam resin type oil absorbents using polyurethane foam, for example.

Most of these conventional oil absorbents, however, fail to offer a fully satisfactory capacity for oil absorption. Further, because of their oil-absorbing mechanism which resides in causing a given oil to be absorbed and retained fast in the voids or pores distributed in their textures, these conventional oil absorbents suffer from the following disadvantages: (1) They produce virtually no voluminal change from the absorbed oil and gain so greatly in bulk density as to inconvenience the works of storage and handling. (2) They are deficient in ability to retain the absorbed oil. Particularly the natural plant type, synthetic fiber type, and foam resin type oil absorbents readily release the absorbed oil even under only slight external pressure. As a result, they call for highly complicated aftertreatments. (3) Though they generally have undergone a treatment for impartation of water repellency, they suffer from a decline of their oil-absorbing ability because of the infiltration of water in the voids after their protracted use in an oil-water mixture system. (4) Though they are capable of absorbing oil from the suspension of oil in water to a certain extent, they are incapable of substantially absorbing oil from the water containing dissolved oil.

As a means for the solution of these problems, oil absorbents of the type using synthetic resins as polymers adapted to absorb a given oil and swell with the absorbed oil have been reported in several articles of literature. The copolymer of t-butyl styrene/divinyl benzene [JP-A-45-27,081(1970)], the cross-linked polymer of t-butyl methacrylate and/or neopentyl methacrylate [JP-A-50-15,882(1975)], the cross-linked polymer of menthyl methacrylate [JP-A-50-59,486(1975)], and the polynorbornene rubber [represented by the product of CdF Corp. marketed under trademark designation of "Norsolex AP"] are examples of the oil absorbent of this type.

The cross-linked polymer of t-butyl methacrylate and/or neopentyl methacrylate, however, fails to exhibit a fully satisfactory absorbing capacity for aliphatic hydrocarbon type oils, though it possesses an appreciable absorbing capacity for such aromatic hydrocarbon type low boiling oils as benzene. The copolymer of t-butyl styrene/divinyl benzene, the cross-linked polymer of menthyl methacrylate, and the polynorbornene rubber manifest an appreciable absorbing capacity for aromatic and aliphatic low boiling hydrocarbon type oils but an inferior absorbing capacity for fatty acid ester type oils, fatty acids, higher alcohols and other similar polar oils, and highly viscous oils. These synthetic resin type oil absorbents, therefore, find utility only in applications of their own limits. They are particularly unfit for the disposal of used edible oils. Moreover, these oil absorbents are slow in absorbing an oil. Particularly at low temperatures, most of these oil absorbents exhibit either a very low oil-absorbing capacity or virtually no oil-absorbing capacity. Thus, they have the disadvantage that they manifest their effects only with difficulty when they are used in a cold district.

Heretofore, in the fields of agriculture, forestry, fishery, and water treatment which have something to do with water, various underwater dissolvable chemical agents have been used for the purpose of extirpating insects, fungi, and weeds in farmlands, rustproofing metals, purifying solutions, defoaming liquids, protecting marine farms from algae, promoting growth of organisms, and luring fish in the sea. These chemical agents have been used by being thrown or scattered in a body of water under treatment either in their unmodified form or in the form of a solution or a dispersant. This method of use, however, has the disadvantage that the chemical agent manifests only a transient effect and overflows the body of water under treatment to be wasted and suffered to contaminate the environment and adversely affect human bodies. In recent years, therefore, the desirability of developing a technique for gradual release of a chemical agent has been finding growing recognition.

As such techniques for gradual release of a chemical agent, several methods which generally comprise depositing a chemical agent on a substrate and allowing the deposited chemical agent to be gradually released from the substrate under water have been reported; e.g. (1) methods which comprise preparing a solid substance having a chemical agent contained in a substrate of an inorganic substance or a polymeric compound and placing this solid substance in a given body of water thereby allowing the chemical agent to be gradually released from the substrate into the water and (2) methods which comprise preparing a coating material having a chemical agent incorporated in a substrate of a non-crosslinking film-forming macromolecular compound, applying this coating material to a given structure, and immersing the coated structure in a body of water thereby allowing the chemical agent to be gradually released from the applied coating.

In the group (1) are included a method which uses clay or a mineral substance as a substrate and causes a chemical agent to be contained in this substrate, a method which uses cement or calcined plaster as a substrate and impregnates this substrate with a chemical agent [JP-A-53-138,885 (1978)], and a method which causes a chemical agent to be contained in an aqueous gel [JP-A-57-163,302(1982)], for example. These methods, however, have the disadvantage that the solid product is liable to disintegrate or dissolve, deficient in ability to retain the chemical agent, susceptible to the influence of water temperature or water current and, therefore, deficient in ability to control the speed of release of the chemical agent, and incapable of easily retaining the effect of the chemical agent for a long time.

In the group (2) are included methods which use non-crosslinking copolymers of (meth)acrylic esters as coating macromolecular compounds [JP-A-51-7,034(1976) and JP-A-58-120,678(1983) and JP-B-1-54,388(1989)], for example. These methods, however, have the disadvantage that since the polymeric compounds used therein are deficient in ability to retain a chemical agent in spite of their possession of a film-forming property, they do not easily allow preparation of a coating material capable of retaining the film-forming property and, at the same time, containing a chemical agent in a large amount and further that since the compounds maintain no sufficient control over the speed of release of the chemical agent, they do not allow the produced coating material to manifest the efficacy of the chemical agent continuously for a long time.

In consequence of changes in the residential environment and improvements in comfortableness of the living spaces, consumers taking a serious interest in the scent have been on the increase and aromatic agents have been establishing themselves as daily necessities in recent years. These aromatic agents have been heretofore used mainly in water closets. At present, they are finding growing utility additionally in room interiors and car interiors. They are expected to find utility in increasingly numerous fields.

The aromatic agents come in various types such as the spray type, liquid type, solid type, and gel type. The aromatic compositions of the gel type, among other types, find particularly popular acceptance because they excel in ability to effect gradual release of the aromatic scent and have no possibility of entailing liquid leakage even when they topple.

The aromatic compositions of the gel type are generally classified under the aqueous gel type and the oily gel type. The aromatic compositions of the aqueous gel type are produced by gelling water with such gelling agents as agar, carrageenan [JP-A-54-135,229(1979)], and a water-soluble polymeric compound [JP-A-55-81,655(1980)] thereby preparing aqueous gels and causing an aromatic essence to be dispersed or solubilized in the aqueous gels in the presence of a surfactant.

These aromatic agents of the aqueous gel type, however, have only a limited aromatic essence content because the aromatic essences are insoluble in water. Since they are generally used as containing an aromatic essence only in a concentration on the order of several percent, they are poor in intensity of aroma and are deficient in ability to retain aroma. They further have the disadvantage that the speed of diffusion of aroma is varied by humidity and the water in the gel is separated and frozen at low temperatures and the gel possesses low strength and yields to dissolution at high temperatures.

In contrast, the aromatic agents of the oily gel type are produced by gelling an aromatic essence or a mixture of an aromatic essence with an oily diluent by using such gelling agents as sodium stearate [JP-A-55-141,243(1980)], benzylidene sorbitol [JP-A-59-77,859(1984)], an amino acid type gelling agent [JP-A-61-206,450(1986)], a styrene-butadiene-styrene copolymer [JP-A-62-249,652(1987)], and a styrene-ethylene-butylene-styrene copolymer [JP-A-62-249,653(1987)], for example. Most of them embody improvements which are capable of eliminating the drawbacks of the aromatic agents of the aqueous gel type.

When sodium stearate, an amino acid type gelling agent, a styrene-butadiene-styrene copolymer, or a styrene-ethylene-butylene-styrene copolymer is used as a gelling agent, the dissolution of the gelling agent in the aromatic essence necessitates a high temperature and consequently tends to entail diffusion, degeneration, discoloration, etc. of the aromatic essence. Further, the oily gel has the disadvantage that the gel which is formed elaborately is re-dissolved once it is exposed to a high temperature as in the car interior.

A procedure which comprises cross-linking an acetoacetylated oligomer in an aromatic essence thereby producing an aromatic gel has been disclosed in [JP-A-62-19,171(1987)]. Specifically, this procedure comprises in cross-linking and gelling acetoacetylated 1,4-polybutadiene in the aromatic essence at normal room temperature in the presence of a cross-linking agent. Most aromatic essences generally possess a reactive substitutent. When such an aromatic essence is used, there ensues the disadvantage that the reaction between the acetoacetyl group and the aromatic essence proceeds to the extent of precluding the formation of the gel. The procedure under present discussion, therefore, requires to use only a specific aromatic essence and dilute this aromatic essence with a large amount of an oily diluent and, therefore, finds utility only in a narrow range of applications. Moreover, the aromatic agent using this acetoacetylated oligomer suffers from the disadvantage that the aromatic essence emits the aroma feebly and tends to lose the constant level of scent.

The gel produced by using the aforementioned conventional oily gelling agent betrays poor strength. For the produced gel to acquire ample strength, therefore, the amount of the gelling agent to be used must be remarkably increased. More often than not, the gel using the gelling agent has the disadvantage that it contains the residue of the gelling agent in a large amount and acquires an opacified texture. Further, the aromatic agents of the conventional oily gel type have the disadvantage that the aromatic essence contained therein in a high concentration is refractory to an attempt to gradually releasing the aroma at a constant level of scent over a long period of time and, actually, the aromatic essence is diffused very quickly or only a specific component of the aromatic essence is diffused in the early stage of use to bring about early impairment of the constant level of scent.

In recent years, in the field of insectifuges for use with clothing, such subliming solid agents as P-dichlorobenzene, naphthalene, and camphor which have heretofore found popular acceptance are now discouraging consumers from continuing their use on account of smell and toxicity. Volatile liquid insectifuges which emit no (or scanty) odor and operate with high safety (such as, for example, the synthetic pyrethroid type insectifuge) have come to attract attention instead. This trend has been giving rise to a demand for a technique capable of providing stable and lasting gradual release of a volatile chemical agent. In the field of such agricultural pesticides as insecticides and fungicides, generally those of the liquid spray type have been heretofore used. In recent years, since these pesticides manifest their effects only transiently, a demand for a technique which allows gradual release of these pesticides and enables the effects of the pesticides to be manifested continuously for a long time has come to take shape in this field.

Several techniques for gradual release of such chemical agents have been reported to the art, including the method which gels a given chemical agent by the use of a gelling agent and the method which causes a chemical agent to be incorporated in a polymeric matrix, for example.

The products obtained in accordance with the method which gels a chemical agent by the use of a gelling agent include an aqueous gel using locust bean gum and xanthane gum as gelling agents [JP-A-53-50,346(1978)], a gel type insecticide using an N-acylamino acid derivative as a gelling agent [JP-A-63-222,104(1988)], and a gel-like solid agent endowed with enhanced viscosity by the use of finely divided silica and alcohol [JP-A-54-92,630(1979)], for example.

These methods which rely on use of a gelling agent invariably have drawbacks. The aqueous gel has the disadvantage that since the speed of diffusion of the chemical agent used therein is affected to a large extent by changes in temperature and humidity, the effect of the chemical agent cannot be stably maintained for a long time, the water in the gel tends to be frozen or separated, and the gelling treatment cannot be effectively applied to a chemical agent which is susceptible of hydrolysis.

When an N-acylamino acid derivative is used as a gelling agent, it requires to be mixed with a volatile chemical agent and preparatorily dissolved at a high temperature. Thus, the method using thie gelling agent cannot be applied to a chemical agent of low boiling point or a chemical agent ready to degenerate with heat and the produced gel has very low strength.

The gel-like solid agent using finely divided silica acquires its enhanced viscosity owing to the thixotropic effect of the finely divided silica. It, therefore, has the disadvantage that it is deficient in stability of the gel and liable to entail separation and disintegration while in storage or in use.

The products reported to the art as obtained in accordance with the method which comprises having a chemical agent incorporated in a polymeric matrix include a mildewcide having a gasifiable chemical agent dispersed in an ethylene-vinyl acetate copolymer [JP-A-56-26,811(1981)] and an insecticidal composition obtained by mixing an insecticide with a copolymer of styrene or α-methylstyrene and an unsaturated carboxylic anhydride and cross-linking the resultant solution by the use of a cross-linking agent [JP-A-57-80,302(1982)], for example. Though the product using the ethylene-vinyl acetate copolymer indeed manifests its effect as a carrier for a gasifying solid chemical agent, it nevertheless has the disadvantage of being inapplicable to a liquid chemical agent.

The method which comprises cross-linking the copolymer of styrene or α-methylstyrene and the unsaturated carboxylic anhydride has the disadvantage that it is applicable only to limited chemical agents and inapplicable to any chemical agent containing in the molecular unit thereof a substituent reactive with the carboxylic anhydride or the cross-linking agent because this method requires to mix the copolymer with the chemical agent preparatorily and solidify the resultant solution with the cross-linking agent.

The conventional method which comprises causing a chemical agent to be incorporated in a polymeric matrix has the disadvantage that the product exhibits a poor ability to retain the effect of the chemical agent for a long time, produces the residue in a very large amount at the end of its service, and encounters difficulty in displaying the extent of consumption of the effect of the chemical agent because this method is incapable of effecting the incorporation of the chemical agent in an ample amount.

Further, most of the conventional techniques described above have the disadvantage that the products thereof exhibit a poor ability to control the diffusion of the chemical agent, suffer the chemical agent to diffuse abruptly in a large amount in the initial stage of service, and fail to manifest the effect of the chemical agent amply for a long time.

Heretofore, in the field of fishing and angling alike, the practice of scattering ground bait within a fixed area for the purpose of attracting fish and enhancing the efficiency of catch has been followed. As baits, such natural creatures as angleworms, lugworms, krills, and shellfish have been generally used either in their unmodified form or in a form kneaded with bean-curd refuse or bread crumb.

These natural baits have the disadvantage that they have no stable supply, encounter difficulty in allowing protracted conservation, necessitate cold storage for prevention of putrefaction, and inconvenience transportation because of bulkiness.

In recent years, the feasibility of a technique for producing a bait capable of gradual release of a fish-luring substance and enhancing the efficiency of catch has been under study. So far, fish-luring agents and false baits having a fish-attracting substance incorporated in an inorganic or polymeric compound have been reported to the art.

To be specific, a fish-luring agent produced by impregnating cement or calcined gypsum with a fish-attracting substance such as fish oil [JP-A-53-138,885(1978)], a false bait grade aqueous gel composition comprising of a polysaccharide and a polyvalent metallic compound [JP-A-62-190,037(1987)], and false bait grade organic polymer compositions allowing a fish-attracting component to be dissolved out simultaneously with a water-soluble organic polymer from a water-insoluble organic polymer [JP-A-59-74,937 (1984), JP-A-59-98,637(1984), and JP-A-60-153,738(1985)], have been reported, for example.

These conventional products, however, have the disadvantage that they provide lasting manifestation of a fish-attracting effect at a constant level only with difficulty and necessitate early replenishment or replacement with new supply because they exhibit a poor ability to retain such fish-attracting oils as fish oil, animal oil, vegetable oil, and insect oil and betray their inability to effect full control of the speed of release of such oils.

Such underwater objects as bottom parts of ships, underwater structures, and fish nets are susceptible to attachment of such aquatic organisms as barnacles, polyzoans, and sea lettuces and, as a result, the ships incur loss of cruising speed, the underwater structures succumb to corrosion, and the fish nets suffer from clogging of their meshes and entail mass destruction of fish enclosed therein. To preclude these disadvantages, antifouling agents have been used as scattered in bodies of water under treatment or applied to the bottom parts of the ships or to the fish nets. The conventional antifouling agents, however, have the problems of poor economy and exertion of adverse effects on the environment inclusive of human bodies because they produce an effective antifouling action only for a short time and, therefore, necessitate frequent repetition of scattering or application and their excesses flow out of the bodies of water under treatment immediately after the scattering or application. In the circumstances, the necessity for developing a technique for enabling an antifouling agent to manifest a lasting effect for a long time has come to find mounting recognition.

Methods which produce antifouling agents endowed with an improved effect-retaining property by the use of rosins and non-crosslinked copolymers of (meth)acrylic esters as vehicles therefor [JP-A-51-7,034(1976), JP-A-58-120,678 (1983), and JP-B-1-54,388(1989)], for example, have been known to the art. Since the vehicles used for these antifouling agents, however, have only a poor ability to retain an antifouling component in spite of the possession of a film-forming property, they are susceptible to the influences of the temperature and current of water and incapable of fully controlling the speed of release of the antifouling component. Further, these vehicles have a disadvantage that they are not easily enabled to incorporate therein a large amount of an antifouling agent while retaining the film-forming property and they are not capable of retaining the effect of the antifouling agent for a long time.

Solid fuels have been heretofore used for camping and tabletop cooking. Most of them are products obtained by using such a low boiling alcohol as methanol or alcohol as a fuel component and gelling the fuel component by the use of a metallic soap or a sorbitol type gelling agent and, therefore, have the following drawbacks.

(1) These fuels have a small calorific value and are incapable of producing an intense fire stably for a long time.

(2) The possibility that, by the heat of the combustion, the components for combustion of these fuels will be partly consumed in the combustion and partly diffused into the ambient air as accompanied by leakage of such harmful substances as methanol and aldehyde and the fuels, on exposure to an elevated temperature while in storage, will induce ignition is high.

(3) The gels incorporating the combustion components are fluidified and eventually liquefied at an elevated temperature.

In recent years, the recovery of the oil accidentally effused on the sea or the oil entrained by the waste water has come to pose a serious problem to the environmental conservation. A strong desire has been expressed for the development of a method for convenient disposal of waste oil discarded in a small amount from homes and plants and machine oil and other similar oils leaking from plants.

As one efficient means for recovering the effused oil or the oil entrained by the waste water or for disposing of the waste oil or leaking oil, the method which comprises causing an absorbent to absorb the oil and subjecting the impregnated absorbent to an aftertreatment of incineration has been in use to date. The absorbents used heretofore for this method include synthetic resin type absorbents formed of such hydrophobic fibers as polypropylene fibers, polystyrene fibers, and polyethylene fibers or non-woven fabrics of such hydrophobic fibers.

Since the conventional synthetic resin type absorbents effect the absorption of oil by causing the voids distributed therein to absorb and retain the oil fast therein, they have the following disadvantages.

(1) They are deficient in ability to retain the absorbed oil, substantially destitute of ability to retain any oil of low viscosity, and ready to release the absorbed viscous oil even under very slight pressure and liable to let down the viscous oil, rendering very difficult the aftertreatment of the impregnated absorbents.

(2) When they are used for the recovery of the oil contained in the oil-water mixture or the oil floating in the form of a thin film on the surface of water, since they absorb the oil only in a low ratio and absorb a large amount of water as well, they sink under water and render their recovery difficult and, after recovery, they are incinerated with great difficulty.

(3) Since the absorbents produce virtually no voluminal change from the absorbed oil, they have high bulkiness before absorbing oil. Thus, they inconvenience the work of storage and handling.

The ventilating fans in kitchens and the ventillating devices in plants are prone to adhesion thereto of oil mist drifted in the air. They, therefore, entail the disadvantage that they tend to grow sticky and collect dirt rather quickly, incur serious impairment of appearance, suffer loss of hygiene, and sacrifice operational efficiency.

At such places as painting plants which inevitably emit oil mist, persons seeking a measure to prevent degradation of labor environment have expressed a strong desire for the development of a method which is capable of providing convenient removal of the oil mist.

For the removal of the oil mist in these circumstances, the method which comprises setting a filter capable of absorbing oil as opposed to the front surface of a ventillating device or an air circulating device has been heretofore employed. Particularly in recent years, for the purpose of obviating the necessity for cleaning this filter, the method which comprises using the non-woven fabric of such sysnthetic resin as polypropylene or polyester as a disposable filter has come to find growing utility.

These conventional filters, however, are deficient in ability to absorb oil mist or incapable of absorbing a large amount of oil mist and, therefore, have the disadvantage that their surfaces collect trickles formed of absorbed oil mist and grow sticky with absorbed oil mist and soil a user's hands when the user changes the used filter with a new supply. Further, since the absorbed oil forms a film on the filter and induces clogging of the filter and seriously degrades the ventilating fan's operational efficiency, these conventional filters incur the disadvantage that they must be frequently replaced.

As a means for sealing joints in an oil pipeline or parts of such machines as pumps which are exposed to oil, the method which comprises improving the oil tightness of such joints by using a sealing material made of an oil-swelling elastomer has been known to the art. An example of the sealing material is produced by kneading such an oil-swelling substance as natural rubber with an oil-resistant synthetic rubber.

The conventional sealing materials, however, require to incorporate therein a fairly large amount of the oil-swelling substance for the purpose of enabling the entire elastomer to be suitably swelled. Thus, they have the disadvantage that the elastomer, after absorbing the oil, suffers the shape-retaining property thereof to be markedly degraded. Most of these conventional sealing materials have the problem of suffering from slow absorption of oil and requiring a long time before manifesting the effect of precluding oil leakage.

In recent years, in consequence of a vigorous growth in the demand for color prints such as gravures and calendars as well as for letterpress prints such as newspapers, magazines, and various publications, the desirability of developing a technique for producing prints at a high speed with high accuracy has been finding enthusiastic recognition.

As a promising means for improving the printability of paper, the concept of enhancing the receptivitity of the paper for ink specifically by enabling the solvent component of the ink to be quickly absorbed in the paper has been proposed.

As a means for enhancing the absorption of the solvent component of the ink by the paper, the method which comprises causing the paper or the applied coating layer on a coated paper to incorporate therein porous inorganic particles possessing an ability to absorb the solvent has been known to the art. In the case of the coated paper, the method which comprises adjusting the interstices between pigment particles in the applied coating layer to a suitable size and allowing the solvent component of the ink to be absorbed in the resultant capillaries has been popularly in practice.

Although these conventional techniques, however, have advantages that the pigment component of the ink allows relatively easily to remain on the surface by adjusting the diameter of pores because the solvent component of the ink is absorbed in the pores, there is disadvantage that it is difficult that only solvent component allows to absorb under remaining a binder polymer and pigment dissolved in the solvent and fixness of the ink lacks.

The thermosensitive recording material is a product to be obtained by forming on a substrate such as paper or film a thermosensitive coloring layer which produces a color on exposure to heat. It has heretofore found utility in printer papers, facsimile papers, passenger tickets issued from automatic vending machines, etc.

The thermosensitive recording material, however, has the disadvantage that, in the course of the application of heat at the time of recording, part of the molten substance occurring in the thermosensitive coloring layer adheres to the thermal head and consequently gives rise to a ropy deposit and impairs the regularity of paper feeding and the ropy deposit on the thermal head solidifies and consequently smears dots and obscures the recording. Further, the thermosensitive recording material offers only poor resistance to oils and solvents. It, therefore, has the disadvantage that when the record produced thereby touches oil such as the grease from the human skin or the hair cream or solvent such as contained in the adhesive tape or the adhesive agent, the colored part of the record fades or vanishes and the white part thereof produces a color, with the result that the recorded image is obscured.

As a means for solving this disadvantage, the method which comprises causing the thermosensitive coloring layer to incorporate therein a filler such as calcium carbonate, aluminum hydroxide, silica, or clay thereby preventing the molten substance in the thermosensitive coloring layer from adhering to the thermal head has been heretofore used. The effect of this method, however, does not deserve to be called fully satisfactory.

The method which, for the purpose of improving the resistance to oil, comprises causing a metal salt of a P-alkylbenzonic acid or a metal salt of an O-benzoylbenzonic acid to be incorporated in a photosensitive coloring layer containing a basic colorless dye and a monophenolic 4-hydroxyphenyl compound [JP-B-2-26,874 (1990)] has been reported to the art. This method, however, manifests its effect only in the case of a specific developer and sparingly manifests its effect in the case of a combination with other developer possessing a high developing effect.

The pressure-sensitive recording sheets which are used as for copying slips in business offices each comprises an upper sheet having formed on the lower surface of a substrate such as of paper a layer including microcapsules containing an involatile oily solution of a color-producing dye such as a leuco dye and a lower sheet having formed on the upper surface of a substrate a layer containing a developing agent capable of reacting with the color-producing dye and causing the color-producing dye to produce a color. They are stacked with their upper sheets superposed severally on their lower sheets in such a manner that the microcapsule-containing layer and the developer-containing layer are opposed to each other. The pressure of a stylus exerted downwardly on the upper surface of the upper sheet fractures the microcapsules and establishes contact between the color-producing dye and the developing agent and consequently forms a given recorded image on the lower sheet.

The pressure-sensitive recording sheets enjoy the advantage that the color-producing dye quickly permeates the developer-containing layer (hereinafter referred to occasionally as a "developer layer") and quickly effects the production of color because this color-producing dye is in the form of a solution in an involatile oily solvent. They, however, have the disadvantage that the color-producing dye blurs the recorded image and prevents its from acquiring a beautiful finish. They also suffer from the disadvantage that the recording image is blurred or vanished when it is suffered to touch oil such as the grease from the human skin or the hair cream or solvent as contained in the adhesive tape or the adhesive agent.

In recent years, the necessity for a technique capable of purifying waste water to a high degree for the sake of conservation of the environment and reclamation of the plant effluent or the household sewage has come to find mounting recognition. Also in ease where a river or a lake, in consequence of contamination, is utilized as a source of water and purified to produce tap water such as city water, this technique for thorough purification of contaminated water is yearned for.

The impurities which are contained in the waste water or the contaminated water mainly include organic compounds, water-soluble inorganic compounds, solid particles, and various fungi, for example. Among other impurities cited above, the oily impurities exert adverse effects on the environment inclusive of human bodies and induce various problems due to offensive odor, displeasing taste, foaming, and coloration even when they are dissolved only slightly in water. Particularly recently, the removal of halogen compounds extremely harmful to human bodies from a water having them dissolved therein has come to pose an important task to the conservation of the environment.

As a means for removing such oily impurities dissolved in water, the method which comprises mixing the waste water or the contaminated water resulting from a primary treatment with granular activated carbon thereby subjecting the dissolved oily impurities to a treatment of adsorption and purifying the water to a high degree has been adopted to date.

The activated carbon, however, exhibits the ability of adsorption not only to the oily impurities desired to be removed but also to such other impurities than the oily impurities as highly water-soluble substances and sparingly water-soluble colloidal particles. In the waste water or the contaminated water containing these impurities, the activated carbon's effect in removing the oily impurities does not last long because the sites of adsorption and the pores in the activated carbon are quick to be clogged with the impurities other than the oily impurities. Further, the activated carbon has no fully satisfactory ability to adsorb the oily impurities and, therefore, suffers from the disadvantage that it is incapable of providing thorough removal of oily impurities from the waste water or the contaminated water containing the oily impurities in a high concentration. Moreover, the granular activated carbon effects the adsorption at a low speed and, therefore, requires an amply long contact time with the waste water or the contaminated water. When it is used for the removal of oily impurities as packed in a column, for example, it has the problem of very poor efficiency of treatment because the speed of passage of the water under treatment through the column cannot be increased.

An object of this invention is to provide an oil-absorbent polymer and uses therefor.

Another object of this invention is to provide a swelling absorbent for oil, which absorbs any of a wide range of oils including edible oils and fatty esters at a high speed with a great capacity and retains the absorbed oil with ample fastness and, moreover, manifests this oil-absorbing ability fully even at low temperatures.

Still another object of this invention is to provide a substrate for underwater gradual release of a chemical agent such as insecticide, fungicide, herbicide, rustproofing agent, purifying agent, deforming agent, algicide, growth accelerator for organisms, and fish-luring agent, which substrate allows the chemical agent to dissolve out into water at a fixed speed and consequently enables it to manifest its effect for a long time.

Yet another object of this invention is to provide an oily gel aromatic agent composition which permits the production thereof to proceed satisfactorily at normal room temperature, excels in the ability to control the diffusion of an aromatic essence without reference to the kind of aromatic essence and the ability to retain the shape of the gel, contains the aromatic component in a high concentration, produces a residue only in a small amount at the end of service, and exhibits highly satisfactory transparency.

A further object of this invention is to provide a gel-like insectifugal, insecticidal, or fungicidal composition which exhibits a high shape-retaining property even at normal room temperature, contains a volatile insectifugal, insecticidal, or fungicidal component in a high concentration, produces a residue in a very small amount at the end of service, excels in the ability to control the diffusion of the chemical component, and exhibits highly satisfactory transparency.

A further object of this invention is to provide a fish-luring composition which allows a fish-luring substance contained therein such as fish oil, animal oil, vegetable oil, or insect oil to be dissolved out in water at a constant rate for a long time, manifests a lasting fish-luring effect, and ensures a high efficiency of catch.

A further object of this invention is to provide an underwater antifouling composition which allows a chemical agent capable of retaining an antifouling effect without reference to such environmental conditions as water temperature and water current to be released at a constant speed for a long time and enables the antifouling effect to last for a long time.

A further object of this invention is to provide a solid fuel composition which produces stable combustion with a high calorific value for a long time, suffers spontaneous diffusion of the fuel component into the ambient air only sparingly even on exposure to elevated temperatures in the process of combustion or storage, and defies fluidization of the solid fuel and therefore enjoys safety.

A further object of this invention is to provide an oil-absorbent material which selectively and efficiently absorbs oil from the oil-water mixture or the sea surface having oil suspended in the form of a thin film thereon, retains the absorbed oil with high fastness, defies release (leakage) of the absorbed oil, enjoys high efficiency of oil recovery, and permits easy disposal as by incineration.

A further object of this invention is to provide an oil mist filter which absorbs oil mist efficiently, prevents the absorbed oil from trickling down or forming a ropy deposit on the surface, and offers effective use for a long time.

A further object of this invention is to provide an oil-absorbent pack which selectively and efficiently absorbs oil from the oil-water mixture or the sea surface having oil suspended in the form of a thin film thereon, excels in the ability to retain the absorbed oil, and allows easy storage and handling because of a very small volume to be assumed before absorption of oil.

A further object of this invention is to provide a sealing material for oil which, on contact with oil, quickly swells to bring about a high sealing effect on the oil, and retains such a high material strength as to escape loss of shape even after swelling with the absorbed oil.

A further object of this invention is to provide a highly printable paper which quickly absorbs selectively the solvent contained in an ink and consequently ensures effective reception of the ink, provides highly satisfactory fixation of the ink thereon even in the process of high-speed printing, and produces a print of beautiful finish free as from fogging.

A further object of this invention is to provide a thermosensitive recording material which prevents the molten substance in the thermosensitive coloring layer from adhering to and accumulating on the thermal head and inducing such adverse phenomena as formation of ropy deposit, impaired regularity of paper feeding, and missing dots and offers highly satisfactory resistance to oils and solvents such that, when the produced record is suffered to touch oil such as the grease of the human skin and the hair cream or solvent such as is contained in the adhesive tape or the adhesive agent, it is not obscured by yielding the colored part thereof to discoloration and the white part thereof to coloration.

A further object of this invention is to provide a pressure-sensitive recording sheet which produces, in response to the pressure exerted by a stylus, a recorded image suffering sparingly from blurring and enjoying a beautiful finish and offers highly satisfactory resistance to oils and solvents such that, when the recorded image is suffered to touch oil such as the grease of the human skin and the hair cream or solvent such as is contained in the adhesive tape or the adhesive agent, it is not blurred or vanished.

A further object of this invention is to provide a method for producing by a technically convenient procedure with high repeatability an oil-absorbent material which provides selective and efficient absorption of oil from the oil-water mixture or the sea surface having oil suspended in the form of a thin film thereon, retains the absorbed oil with high fastness, avoids spontaneous release (or leakage) of the absorbed oil and consequently enjoys highly satisfactory efficiency of oil recovery, and permits easy disposal as by incineration.

A further object of this invention is to provide a method for the removal of oil dissolved in water, which allows oil of meager or sparing solubility in water contained as dissolved in such water as the waste water or the polluted reservoir water to be selectively and quickly removed even when various impurities such as water-soluble substances and water-insoluble colloidal particles are present therein in addition to the oil.

SUMMARY OF THE INVENTION

The objects described above are accomplished by a swellable oil-absorbent agent formed of a cross-linked polymer (P) obtained by polymerizing a monomer component comprising 90 to 99.999% by weight of a monomer having as a main moiety thereof an alkyl (meth)acrylate the alkyl group of which has 10 to 16 carbon atoms and possessing one polymerizable unsaturated group in the molecular unit thereof and 0.001 to 10% by weight of a cross-linkable monomer possessing at least two polymerizable unsaturated groups in the molecular unit thereof (providing that the total of the amount of the polymerizable monomer and that of the cross-linkable monomer is 100% by weight).

These objects are also accomplished by a substrate for underwater gradual release of a chemical agent, which substrate is formed of the cross-linked polymer (P).

These objects are further accomplished by an underwater antifouling composition formed by causing an antifouling component to be incorporated in the cross-linked polymer (P).

These objects are further accomplished by a gel-like aromatic agent composition formed by causing an aromatic component to be incorporated in the cross-linked polymer (P).

These objects are further accomplished by a gel-like insectifugal, insecticidal, and fungicidal composition comprising the cross-linked polymer (P) and a volatile effective component containing at least one chemical agent selected from the group consisting of insectifuges, insecticides, and fungicides.

These objects are further accomplished by a fish-luring composition comprising the aforementioned cross-linked polymer (P) and a fish-luring substance.

These objects are further accomplished by a solid fuel composition comprising the aforementioned cross-linked polymer (P) and a liquid fuel component.

These objects are further accomplished by an oil-absorbing composite having carried on a substrate a cross-linked polymer (P).

These objects are further accomplished by an oil-absorbent pack having a bag of hydrophobic porous fabric filled with particles of the cross-linked polymer (P).

These objects are further accomplished by an oil-absorbent material, depositing the cross-linked polymer (P) on a hydrophobic porous substrate.

These objects are further accomplished by a method for manufacturing an oil-absorbent material which comprises impregnating a monomer component comprising 90 to 99.999% by weight of a monomer having as a main moiety thereof an alkyl (meth)acrylate the alkyl group of which has 10 to 16 carbon atoms and possessing one polymerizable unsaturated group in the molecular unit thereof and 0.001 to 10% by weight of a cross-linkable monomer possessing at least two polymerizable unsaturated groups in the molecular unit thereof (providing that the total of the amount of the polymerizable monomer and that of the cross-linkable monomer is 100% by weight), with a hydrophobic porous substrate, dipping said impregnated substrate into a water bath, and polymerizing said monomer component thereby supporting a cross-linked polymer (P) on said hydrophobic porous substrate.

These objects are further accomplished by a method for the removal of an oil component dissolved in water, which method comprises mixing the aforementioned cross-linked polymer (P) as an underwater absorbent for dissolved oil with a body of water having the oil component dissolved therein thereby causing the absorbent to absorb and retain therein the dissolved oil component.

Since the swelling oil-absorbent agent of this invention comprises a (meth)acrylate type cross-linked polymer possessing within the molecular unit thereof a multiplicity of specific long-chain aliphatic hydrocarbon groups effective in causing manifestation of an oil-absorbing ability, it quickly absorbs a large amount of any of a wide variety of oils including not only aromatic hydrocarbon and aliphatic hydrocarbon type oils but also fatty acid ester type oils, higher fatty acids, higher alcohols, and ethers while absorbing virtually no water. The oil-absorbing ability of this agent is affected only slight by changes in temperature and is retained at a high level even at low temperatures.

The swelling oil-absorbent agent of this invention, therefore, manifests the effect thereof in the recovery of the oil accidentally effused on the sea, the recovery of floating oil, and the recovery of oil contained in the waste water even at low temperatures. It also finds utility in a very wide range of applications including emulsion breaker, agent for disposal of leaked oil, agent for disposal of used edible oil, agent for disposal of spent machine oil, household and industrial oil-wiping agent, chemical dustcloth, leaked oil sensor, oil-sealing agent, and various oil-retaining agents. Further, since the swelling oil-absorbent agent of this invention is capable of absorbing and retaining a wide variety of oils, it can be used also as a substrate for gradual release of various aromatic agents, insecticides, fish-luring agents, etc.

The substrate formed of a specific cross-linkable polymer of this invention and used for underwater gradual release of a chemical agent is capable of absorbing and retaining therein a water-soluble chemical agent by virtue of high interactivity and, therefore, is allowed to form a stable composition containing therein a large amount of a chemical agent dissoluble in water. The substrate of this invention, therefore, enables the water-dissoluble chemical agent once absorbed and retained therein to be efficaciously released at a fixed rate into water and, owing to this highly effective control of the gradual release, allows the chemical agent to manifest its effect continuously for a long time.

Further, since this substrate can be used in a varying form befitting a particular purpose to be selected, it finds utility in a wide variety of applications which have something to do with water. Moreover, it is economical and incapable of exerting adverse effects on the environment and on human bodies.

The underwater antifouling composition of the present invention contains a specific cross-linked polymer which exhibits high power to retain an antifouling component and, therefore, allows the antifouling component to be contained in a large amount therein. Thus, this composition enables the antifouling component to be efficaciously released at a fixed rate into water and, owing to this highly effective control of the gradual release, allows the antifouling agent to manifest its effect continuously for a long time.

The underwater antifouling composition of the present invention, therefore, obviates the necessity for replenishing the composition being used in the water under treatment or repeating the application of the composition to the bottom part of a ship or to the fish net. It is economical and has virtually no possibility of exerting any adverse effect on the environment and human bodies.

The gel-like aromatic composition of this invention is a product which is obtained by having an aromatic component incorporated in a specific cross-linked polymer. It can be otherwise produced by causing the cross-linked polymer to be impregnated with the aromatic component by virtue of absorption at normal room temperature. It, therefore, has no possibility of the aromatic component being diffused, degenerated, or discolored in the process of production of the composition. Since the cross-linked polymer used in the composition is derived from a monomer possessing high compatibility with the aromatic component, the composition shows a stable ability to retain the intensity and tone of aroma to a wide variety of aromatic components.

Further, since the gel-like aromatic composition of this invention is gelled by the use of a specific cross-linked polymer, it possesses high gel strength, excels in ability to retain shape, avoids dissolution even at elevated temperatures, and, at the same time, attains diminution in the amount of the residue owing to the improved capacity of the composition for the aromatic component. The gel-like aromatic composition of this invention is rich in transparency and excellent pre-eminently in appearance. The gel-like aromatic composition of this invention, therefore, can be used as an aromatic agent for car interiors, room interiors, water closets, bathrooms, and telephone sets. This aromatic composition mixed with a medicine or an insecticide can be effectively used as a multi-purpose aromatic agent in a rich variety of applications.

The gel-like insectifugal, insecticidal, and fungicidal composition of this invention is a product which is obtained by causing a specific cross-linked polymer to incorporate therein a volatile effective component containing an insectifuge, insecticide, and fungicide. It may be otherwise produced by causing the cross-linked polymer to be impregnated with the volatile effective component by virtue of absorption at normal room temperature. This composition, therefore, has no possibility of the volatile effective component being diffused, degenerated, or discolored in the process of production of the composition. Since the cross-linked polymer used in the composition is obtained from a monomer which exhibits high compatibility with the volatile effective component, the composition excels in ability to control the diffusion of the active component and produce the insectifugal, insecticidal, and fungicidal effect of constant intensity continuously for a long time.

Further, the gel-like insectifugal, insecticidal, and fungicidal composition of this invention abounds in transparency, enjoys beautiful appearance, excels in heatproofness and shape-retaining property, readily tells the degree of consumption of the active component because the amount of the residue to be produced at the end of service is small.

The fish-luring composition of this invention is a product which is obtained by causing a specific cross-linked polymer to be impregnated with a fish-luring substance by virtue of absorption at normal room temperature. It, therefore, has no possibility of the fish-luring substance being diffused or degenerated in the process of production of the composition.

Further, since the fish-luring composition of this invention is stably gelled owing to the interaction of the fish-luring substance and the cross-linked polymer, it enables the fish-luring substance contained in the gel to be gradually released at a constant rate into the water and allows the fish-luring effect to be manifested continuously for a long time.

The fish-luring composition of this invention does not allow the fish-luring substance initially incorporated therein to be released in the form of droplets under an external pressure such as of water. Thus, the possibility of the fish-luring substance leaking from the composition, floating to the water surface, and polluting the environment is nil.

The fish-luring composition of this invention, when amply lodged as in a net by impregnation and immersed in situ in water, can be used as a highly effective fish-luring agent. Since the fish-luring composition excels in ability to retain the shape of the gel and consequently the fish-luring agent can be recovered completely after wholly releasing the fish-luring substance therefrom, this composition proves to be highly desirable from the standpoint of environmental conservation.

A product obtained by incorporating the fish-luring composition of this invention in a false bait in popular use can be used as a false bait endowed with a lasting fish-luring effect. Further, since the fish-luring composition of this invention is a tenacious gelled product, it can be molded directly in the shape of a false bait and put to use as a false bait. Otherwise, a product obtained by applying this fish-luring composition in the form of a film to the surface of a skeleton molded in advance with a suitable material in the shape of a false bait may be used as a false bait.

The fish-luring composition of this invention can find extensive utility in applications such as fish-luring agents for fishing and angling, false baits endowed with a fish-luring effect, and fish-luring agents for culture ponds which are invariably aimed at luring and catching fish.

The solid fuel composition of this invention is a product obtained by causing a cross-linked polymer resulting from the polymerization of a specific monomer to absorb and retain therein a large amount of a liquid fuel component and subsequently gelling the resultant composite, therefore, defies liquefaction even at elevated temperatures and, on ignition, produces combustion of the liquid fuel component thereof with a constant calorific value.

Further, since the solid fuel composition of this invention contains a liquid fuel component possessing a high calorific value, it produces a fire of great intensity and permits a notable reduction in size of the composition as compared with the conventional solid fuel using alcohol. In terms of toxicity, since this solid fuel composition allows the option on the selection of a safe fuel, it has no possibility of emitting a toxic gas in the process of combustion or storage.

Moreover, the cross-linked polymer which is used in the solid fuel composition of this invention is capable of swelling by absorbing a large amount of a fuel component even at normal room temperature and subsequently forming a galled composition. When the cross-linked polymer remains intact during or after the use of the solid fuel composition, the solid fuel composition may be regenerated for reuse by causing the remaining cross-linked polymer to absorb the liquid fuel component.

The solid fuel composition of this invention, therefore, manifests its excellent function in camping and in table-top cooking at private residences and business establishments as well.

The oil-absorbing composites contemplated by this invention are allowed to form various products by varying the substrate to be used and the procedure to be employed for deposition of an effective component and manifest various effects which are inherent in such products.

For example, an oil-absorbent material is obtained by using a hydrophobic porous material as a substrate and depositing the aforementioned cross-linked polymer on this substrate. This oil-absorbent material performs the function of causing the cross-linked polymer to swell by absorbing the oil already adsorbed on the hydrophobic porous substrate, it possesses the outstanding oil-absorbing properties shown in (1) and (2) below as compared with the conventional oil-absorbent material.

(1) It excels in ability to retain the absorbed oil and allows very easy disposal thereof at the end of service without giving rise to any ropy residue.

(2) It provides selective absorption of oil while absorbing virtually no water and, therefore, ensures highly effective recovery of oil from the oil-water mixture or from the sea surface having oil suspended in the form of a thin film thereon.

The oil-absorbent material of this invention, therefore, provides highly effective disposal of the used oil at private residences, the spent oil at plants, the leaked oil, and the oil accidentally effused in pits, harbors, lakes and swamps, and seas, for example.

When the oil-absorbent composite of this invention is adapted to serve as an oil mist filter and set in place in the inlet of a ventillating device or an air circulating device, it efficiently recovers oil mist drifted in a kitchen or a plant and cleans the air and, at the same time, prevents the oil from being deposited on the fan and the inner part of the ventillating device or the air circulating device. Since the oil recovered by this oil mist filter neither trickles down nor forms a ropy deposit on the surface thereof, the oil mist filter can be very easily disposed of at the end of service.

Further, the oil mist filter of this invention enjoys a long service life because the oil mist is absorbed and retained by the cross-linked polymer contained in the filter and, consequently, the oil neither forms any film on the surface of the filter nor clogs the texture of the filter.

The oil mist filter of this invention, therefore, manifests an extremely high effect in the removal of oil mist as a filter for the ventillating fan in a household kitchen or the ventillating device or air circulating device in a plant or a manufactory, for example.

A thermosensitive recording material is obtained by depositing the aforementioned cross-linked polymer on a thermosensitive coloring layer as a substrate or on the carrier thereof. This thermosensitive recording material discourages the molten substance occurring in the thermosensitive coloring layer during the application of heat at the time of recording from adhering to or accumulating on the thermal head. It, therefore, produces a record of highly satisfactory clarity because the possibility of the molten substance smearing the thermal head and producing a ropy deposit, impairing the regularity of paper feeding, and giving rise to missing dots is nil.

Even when the thermosensitive recording material of this invention is suffered to touch oil such as the grease of the human skin or the hair cream or solvent such as is contained in the adhesive tape or the adhesive agent, the colored part of the produced record is neither discolored nor vanished and the white part thereof is not colored. Thus, the thermosensitive recording material excels in resistance to oil and solvent.

The detailed mechanism of the operation of the cross-linked polymer remains yet to be elucidated. The ability of the cross-linked polymer of this invention to deject the adhesion or accumulation of the molten substance to or on the thermal head may be logically explained by a postulate that this cross-linked polymer has an ability to absorb a wide variety of oils and, when the thermosensitive coloring layer is heated, absorb and retain the molten substance already deposited and accumulated on the thermal head. When oil or solvent is suffered to adhere to the thermosensitive recording material, the possibility that the colored part of the produced record is discolored as it is dissolved in the oil or the solvent and the white part thereof is colored as the coloring components such as basic dye and a metal salt of organic acid contained therein and the developer are dissolved in the oil or the solvent and consequently caused to react with each other is precluded presumably because the cross-linked polymer absorbs the oil or the solvent.

The thermosensitive recording material of this invention produces a record of beautiful finish and excels in resistance to oils and solvents and, therefore, finds utility extensively in facsimiles, measuring recorders, passenger tickets issued by automatic vending machines, computer terminals, and labels, for example.

A pressure-sensitive recording sheet is obtained by depositing the cross-linked polymer on a developing layer as a substrate or on the supporting member thereof. When the recorded image produced on this pressure-sensitive recording sheet is suffered to contact oil such as the grease of human skin or the hair cream or solvent such as is contained in the adhesive tape or the adhesive agent, it is blurred or vanished very sparingly.

The detailed mechanism of the operation of this cross-linked polymer remains yet to be elucidated. The ability of the cross-linked polymer used in this invention to prevent the recorded image from being blurred by the oil or the solvent may be logically explained by a postulate that when the microcapsules containing an involatile oily solution of coloring dye are ruptured by the pressure as of a stylus, the cross-linked polymer absorbs the unnecessary involatile oily solvent already permeated the developing agent layer immediately after coloration. When oil or solvent is suffered to adhere to the pressure-sensitive recording sheet, the recorded image is prevented from being blurred or vanished presumably because the cross-linked polymer quickly absorbs the oil or the solvent.

The pressure-sensitive recording sheet of this invention produces a recorded image of beautiful finish and excels in ability to resist oils and solvents and, therefore, finds extensive utility as copying slips for business offices, serial slips, passenger tickets issued from automatic vending machines, and output sheets of computers, for example.

An oil sealing material is obtained by using a thermoplastic resin and/or an elastomer as a substrate and dispersing the aforementioned cross-linked polymer in the substrate. This oil sealing material shows a high sealing effect to oil because this material, on contact with oil, quickly and suitably swells by absorbing the oil owing to the interaction between the cross-linked polymer and the substrate. It amply tolerates long continuous service because it defies deformation due to absorption of oil and retains the stated shape intact for a long time.

The oil sealing material of this invention, therefore, finds extensive utility as a sealing material at joints in an oil piping, an oil-stopping agent for leaked oil, an oil stopper, and various sorts of packing, for example.

A paper of high printability of this invention is obtained by using a paper or a paper coating layer thereon as a substrate and depositing the aforementioned cross-linked polymer on the substrate. This paper contains a cross-linked polymer which swells by absorbing a large amount of the solvent in the ink. It follows that when a printing ink is transferred onto this paper, the paper selectively and quickly absorbs the solvent in the ink.

When the paper of this invention is used in printing, therefore, the ink dries quickly on the paper and the active component of the ink efficiently fixes itself on the paper. Thus, the ink is neither blurred nor fogged but is enabled to produce a print of high density and beautiful finish.

Thus, the paper provided by this invention effectively improves the finish of color prints such as high-speed prints, gravures, and calendars and also improves the accuracy of printing and contributes greatly to the growth of industry.

The paper of this invention can be easily obtained by using an aqueous dispersion of a specific cross-linked polymer as mixed with an aqueous dispersion of pulp or a paper coating.

The oil-absorbent pack of this invention is a product which is obtained by filling a bag of hydrophobic porous cloth with particles of a cross-linked polymer resulting from the polymerization of a specific hydrophobic monomer component. Since the cross-linked polymer used in this oil-absorbent pack performs the function of swelling by absorbing the oil already adsorbed on the hydrophobic porous cloth, the oil-absorbent pack possesses the outstanding oil-absorbing properties shown in (1) to (3) as compared with the conventional oil-absorbing materials.

(1) It excels in ability to retain the absorbed oil, avoids producing a ropy deposit, and permits very easy disposal of itself at the end of service.

(2) It absorbs virtually no water and selectively absorbs oil and, therefore, provides highly effective recovery of oil from the oil-water mixture or from the sea surface having oil suspended in the form of a thin film thereon.

(3) Since it quickly absorbs a large amount of oil and assumes a very small volume prior to use, it can be stored or handled with ease.

The oil-absorbent pack of this invention, therefore, is used very effectively in the disposal of the used oil at private residences, the spent oil at plants, the leaked oil, and the waste water, and the oil accidentally effused in pits, harbors, lakes and swamps, and seas, for example.

In accordance with the method of this invention for the production of an oil-absorbent material, the oil-absorbent cross-linked polymer can be fixed uniformly and firmly on the hydrophobic porous substrate by a technically convenient procedure. Moreover, the oil-absorbent material obtained by the method of this invention possesses highly desirable properties as compared with the conventional oil-absorbent materials.

Specifically, since the oil-absorbent material obtained by the method of this invention possesses an oil-absorbing mechanism such that the oil-absorbent cross-linked polymer swells by absorbing the oil already adsorbed on the hydrophobic porous substrate, it possesses highly satisfactory oil-absorbing properties shown in (1) and (2) below as compared with the conventional oil-absorbent materials.

(1) It excels in ability to retain the abnsorbed oil, avoids producing a ropy deposit, and permits very easy disposal as by incineration.

(2) It absorbs virtually no water and selectively absorbs oil and, therefore, attains highly effective recovery of oil from the oil-water mixture or the sea surface having oil suspended in the form of a thin film thereon.

Thus, this invention provides a method for the production of an oil-absorbent material which befits the disposal of the used oil at private residences, the spent oil at plants, the leaked oil, and the waste water, and the oil accidentally effused in pits, harbors, lakes and swamps, and seas, for example.

The method of this invention for the removal of oil dissolved in water consists in using a cross-linked polymer resulting from the polymerization of a specific hydrophobic monomer component as an absorbent for the dissolved oil in water. The cross-linked polymer to be used in this invention possesses a great ability to absorb oil. It is capable of quickly absorbing the oil dissolved in water and retaining it. The cross-linked polymer to be used in this invention, unlike the activated carbon, avoids absorbing organic and inorganic substances possessing high solubility in water. Since this cross-linked polymer possesses no pore in the texture thereof, the possibility of this polymer having its ability of absorption degraded by clogging of pores by colloidal particles is nil. By the method of this invention for the removal of oil dissolved in water, therefore, the oil which is meagerly or sparingly soluble in water can be selectively and quickly removed not only when this oil is dissolved alone in water but also when various impurities such as water-soluble substances and water-insoluble colloidal particles are contained in water besides the oil. Even the portion of the oil which escapes solution in water because of saturation and remains in a suspended state therein can be efficiently absorbed and removed by this method.

The method of this invention for the removal of oil dissolved in water, therefore, is highly effective in removing from the waste water or polluted water a harmful oil which is meagerly or sparingly soluble in water. As a means for purifying a polluted water to a high degree, this method is highly effective in disposing of the plant effluent or the household sewage or in reclaiming tap water such as city water from oil-containing polluted water as the source of water.

EXPLANATION OF THE PREFERRED EMBODIMENT

This invention is directed to a cross-linked polymer (P) obtained by polymerizing a monomer component comprising 90 to 99.999% by weight of (A) a monomer having as a main moiety thereof a (meth)acrylate of a monovalent aliphatic alcohol of 10 to 16 carbon atoms and possessing one polymerizable unsaturated group in the molecular unit thereof and 0.001 to 10% by weight of (B) a cross-linkable monomer possessing at least two polymerizable unsaturated groups in the molecular unit thereof (providing that the total of the amounts of the monomers (A) and (B) is 100% by weight). The cross-linked polymer (P) is useful as a swellable oil-absorbent agent.

The (meth)acrylate which constitutes itself the main moiety of the monomer (A) of this invention possessing one polymerizable unsaturated group in the molecular unit thereof is a (meth)acrylate of a monovalent aliphatic alcohol of 10 to 16 carbon atoms represented by the general formula,

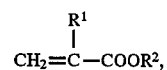

wherein $R^1$ is a hydrogen atom or methyl group and $R^2$ is an aliphatic hydrocarbon group of 10 to 16 carbon atoms. The number of carbon atoms of the aliphatic hydrocarbon group in the (meth)acrylate must be in the range of 10 to 16. If the number of carbon atoms is less than 10, the produced cross-linked polymer possesses no sufficient ability to absorb oil. If the (meth)acrylate to be used is such that the number of carbon atoms in the aliphatic hydrocarbon group thereof exceeds 16, since the crystallinity between the side chains is high, the produced cross-linked polymer exhibits a conspicuously low oil-absorbing property at normal room temperature.

The (meth)acrylates of monovalent aliphatic alcohols having 10 to 16 carbon atoms which are effectively usable herein include decyl (meth)acrylates, dodecyl (meth)acrylates, tetradecyl (meth)acrylates, and hexadecyl (meth)acrylates, for example. These (meth)acrylates may be used either singly or in the form of a combination of two or more members.

The amount of the (meth)acrylate of a monovalent aliphatic alcohol of 10 to 16 carbon atoms to be used in the monomer (A) is such that the (meth)acrylate accounts for a main moiety, namely not less than 50% by weight, of the monomer (A). If the proportion of the (meth)acrylate to the total amount of the monomer (A) is less than 50% by weight, the produced cross-linked polymer is deficient in oil-absorbing properties, particularly at low temperatures and relative to polar oils and highly viscous oils.

For this invention, therefore, the monomer (A) requires to contain therein not less than 50% by weight of the (meth)acrylate represented by the aforementioned general formula. This monomer (A) may contain therein in a proportion not exceeding 50% by weight a monomer excluding the (meth)acrylate and possessing one polymerizing unsaturated group in the molecular unit thereof.

The monomers which are effectively usable in combination with the (meth)acrylate in the monomer (A) include (meth)acrylates of monovalent aliphatic alcohols of not more than 9 carbon atoms such as methyl (meth)acrylates, ethyl (meth)acrylates, butyl (meth)acrylates, 2-ethylhexyl (meth)acrylates, and n-octyl (meth)acrylates; (meth)acrylates of monovalent aliphatic alcohols of not less than 17 carbon atoms such as octadecyl (meth)acrylates and behenyl (meth)acrylates; (meth)acrylates of alicyclic alcohols such as cyclohexyl (meth)acrylates and menthyl (meth)acrylates; (meth)acrylates of phenols such as phenyl (meth)acrylates and octylphenyl (meth)acrylates; aminoalkyl (meth)acrylates such as dimethylaminoethyl (meth)acrylates and diethylaminoethyl (meth)acrylates; (meth)acrylates possessing a polyoxyethylene chain such as polyethylene glycol mono(meth)acrylates and methoxypolyethylene glycol mono(meth)acrylates; (meth)acrylamides such as (meth)acrylamides, N-methylol (meth)acrylamides, and dimethylaminoethyl (meth)acrylamides; polyolefins such as ethylene and propylene; aromatic vinyl compounds such as styrene, α-methyl styrene, and t-butyl styrene; and vinyl chloride, vinyl acetate, acrylonitrile, and (meth)acrylic acids, for example. These monomers may be used either singly or in the form of a combination of two or more members.

The cross-linkable monomer (B) to be used in this invention possesses at least two polymerizable unsaturated groups in the molecular unit thereof and functions as a cross-linking agent.

The cross-linkable monomers (B) which are effectively usable herein include ethylene glycol di(meth)acrylates, diethylene glycol di(meth)acrylates, polyethylene glycol di(meth)acrylates, polyethylene glycol polypropylene glycol di(meth)acrylates, polypropylene glycol di(meth)acrylates, 1,3-butylene glycol di(meth)acrylates, N,N-propylene bis-acrylamide, diacrylamide dimethyl ether, N,N-methylene bis-acrylamide, glycerol di(meth)acrylates, neopentyl glycerol di(meth)acrylates, 1,6-hexane diol di(meth)acrylates, trimethylol propane tri(meth)acrylates, tetramethylol propane tetra(meth)acrylates, polyfunctional (meth)acrylates obtained by the esterification of alkylene oxide adducts of polyhydric alcohols (such as, for example, glycerin, neopentyl glycol, trimethylol propane, trimethylol ethane, and tetramethylol methane) with (meth)acrylic acids, and divinyl benzene, for example. These cross-linking monomers may be used either singly or in the form of a combination of two or more members.

The ratio of the monomers (A) and (B) in the monomer component to be used in the production of the cross-linked polymer (P) is such that the monomer (A) accounts for a proportion in the range of 90 to 99.999% by weight and the monomer (B) for a proportion in the range of 0.001 to 10% by weight, based on the total of the amounts of the monomers (A) and (B). If the proportion of the monomer (A) exceeds 99.999% by weight or that of the cross-linkable monomer (B) is less than 0.001% by weight, the produced cross-linked polymer gains in solubility in oil and, after absorbing an oil, assumes flowability and consequently suffers from a decline in the oil-retaining property. If the proportion of the cross-linkable monomer (B) is so large as to exceed 10% by weight, the produced cross-linked polymer assumes an unduly high cross-link density and, after contacting an oil, exhibits an insufficient swelling property and fails to absorb the oil in a sufficiently large amount.

Copolymerization of the aforementioned monomer component by the use of a polymerization initiator suffices to effect production of the cross-linked polymer (P). This copolymerization may be accomplished by any of the known methods such as polymerization in a solvent, emulsion polymerization, suspension polymerization, and bulk polymerization, for example.

The solution polymerization can be carried out in a solvent in the presence of an oil-soluble polymerization initiator. The solvents which are effectively usable herein include alcohols such as ethyl alcohol and isopropyl alcohol, aromatic or aliphatic hydrocarbons such as benzene, toluene, xylene, cyclohexane, and n-hexane, ketches such as methylethyl ketone, and esters such as ethyl acetate, for example. The oil-soluble polymerization initiators which are effectively usable herein include organic peroxides such as benzoyl peroxide, lauroyl peroxide, and cumene hydroperoxide and azo compounds such as 2,2'-azobis-isobutylonitrile and 2,2'-azobis-dimethylvaleronitrile, for example. The polymerization temperature is generally in the range of 0° to 150° C. The apparatus to be used for this polymerization may be a stirring tank or a kneader. By the solution polymerization to be performed as described above, a viscous liquid or a gel which contains a cross-linked polymer (P) aimed at can be obtained.

The emulsion polymerization is accomplished by supplying the monomer component in combination with a water-soluble polymerization initiator such as ammonium persulfate or potassium persulfate or a redox type polymerization initiator composed of the water-soluble polymerization initiator and a reducing agent such as sodium hydrogen sulfite to water, emulsifying them by the use of an emulsifier possessing a high HLB value, and polymerizing the resultant emulsion at a temperature in the range of 0° to 100° C. It consequently produces an aqueous emulsion which contains the cross-linked polymer (P) in the form of minute particles approximately 0.01 to 10 μm in diameter.

The suspension polymerization is accomplished by suspending the monomer component in water by the use of an emulsifier having a high HLB value or a protective colloid agent such as polyvinyl alcohol, hydroxyethyl cellulose, or gelatin and polymerizing the resultant suspension in the presence of an oil-soluble polymerization initiator. The polymerization temperature is preferable to be in the range of 0° to 150° C. The cross-linked polymer (P) in a granular form can be produced by filtering the aqueous suspension of minute resin particles 1 to 1,000 μm in diameter and drying the filtrate.

The bulk polymerization is accomplished, for example, by casting the monomer component in the presence of a polymerization initiator into a die and polymerizing the monomer component in the die at a temperature of 0° to 150° C. Consequently, the cross-linked polymer (P) can be obtained as molded in conformity with the die.

The swellable oil-absorbent agent of this invention which comprises the cross-linked polymer (P) obtained as described above can be used in various forms. For example, the swellable oil-absorbent agent of this invention may be used directly as added to or sprayed in an oil-water mixed system or an oil system such as an oil-water suspension or an aqueous solution having oil dissolved therein. It may be used as packed in a release container like a cylindrical tube. Otherwise, the swelling oil-absorbing agent of this invention may be used as attached fast to or occluded in a fibrous substance or packed in a textile bag or package.

Further, the swellable oil-absorbent agent may be used as combined with such known oil absorbents or fillers as rice hull, straw, pulp, cotton, porous lime, porous silica, porous pearlite, and polypropylene fiber.

The cross-linked polymer (P) of this invention which is effectively used as a sustrate for an underwater gradual release of chemical agent can be mixed with an underwater dissolving chemical agent and used as an underwater gradual release chemical agent composition. The underwater dissolving chemical agent is required to exhibit solubility in oil, possess solubility of at least 1 ppm in water, and manifest the efficacy of an insecticide, fungicide, herbicide, rustproofing agent, a purifying agent, a defoaming agent, algicide, organic growth accelerator, fish-luring agent, etc. so as to suit the particular purpose of use. It can be selected from various substances meeting the requirement. The underwater dissolving chemical agents which are effectively usable herein include alcohols such as octanol and tridecanol; carboxylic acids and salts thereof such as caproic acid, oleic acid, copper laurate, calcium myristate, and naphthenic acid and salts thereof; thiols such as dodecyl mercaptan; amines and salts thereof such as butyl amine, tributyl amine, diphenyl amine and salts thereof, and lauryl amine and salts thereof; animal and vegetable oils such as rapeseed oil, castor oil, whale oil, and beef tallow; quaternary ammonium salts such as benzene thorium chloride and alkyl pyridinium salts; phenols such as alkyl phenols, trichlorophenol, and eugenol; esters such as dibutyl phthalate, dioctyl phthalate, and ethyl oxybenzoate; organic chlorine compounds such as 3-chloro-2-methyl-propene and dichlorobenzene; organic tin compounds such as triphenyl tin chloride; this ethers such as dialkyl sulfide; amino acids such as histidine and glutamine; hydrocarbons such as kerosene, benzene, toluene, and xylene; carbamates such as 2-isopropylphenyl-N-methyl carbamate; phosphates such as 4-methylthiophenyl dipropyl phosphate; pyrethroids such as Empenthline and Arethline; nucleic acids such as adenine and adenosine; and phospholipids such as lecitin. These underwater dissolving chemical agents may be used either singly or in the form of a combination of two or more members.

When the underwater chemical agent gradual release substrate of this invention comprising the cross-linked polymer (P) and the underwater dissolving chemical agent are mixed to produce the underwater gradual release chemical agent composition, though their mixing ratio is not particularly restricted, the cross-linked polymer (P) is desired to account for a proportion in the range of 2 to 80% by weight and the underwater dissolving chemical agent for a proportion in the range of 20 to 98% by weight based on the total amount of the composition. If the amount of the cross-linked polymer (P) to be used is less than 2% by weight, the disadvantage arises that the underwater dissolving chemical agent is not completely absorbed in the produced composition but suffered to remain in a free state. If this amount exceeds 80% by weight, the disadvantage ensues that the underwater dissolving chemical agent is not dissolved out in an amount enough to manifest the effect of the chemical agent. The composition may incorporate therein, in addition to the substrate and the chemical agent, organic solvents and other similar additives which lack the efficacy of a chemical agent and serve the purpose of facilitating the handling of the chemical agent and controlling the speed of release of the chemical agent.

As means for producing the underwater gradual release of chemical agent composition by mixing the underwater chemical agent gradual release substrate of this invention with the underwater dissolving chemical agent, the method which comprises mixing a liquid containing the cross-linking polymer (P) with the underwater dissolving chemical agent and thereafter expelling the solvent from the resultant mixture, the method which comprises keeping the cross-linked polymer (P) in a pelletized or molded form immersed for a prescribed time in a bath of the underwater dissolving chemical agent thereby causing the cross-linked polymer (P) to absorb the underwater dissolving chemical agent and subsequently removing the produced underwater gradual release chemical agent composition from the bath, or the method which comprises mixing the monomer component destined to form the cross-linked polymer (P) with the underwater dissolving chemical agent and polymerizing the resultant monomer component solution thereby producing the underwater gradual release chemical agent composition may be adopted. When the cross-linked polymer (P) is caused to absorb the underwater dissolving chemical agent, the absorption of the chemical agent may be accelerated by applying heat to an extent short of inducing diffusion or degeneration of the underwater dissolving chemical agent or by using a solution having the underwater dissolving chemical agent dissolved or dispersed in a solvent.

For the use of the composition resulting from the mixture of the underwater chemical agent gradual release substrate of this invention with the underwater dissolving chemical agent, there may be employed a varying method which is selected to suit the particular purpose for which the composition is used or the particular place at which the composition is used. The method which comprises dissolving the composition comprising the cross-linked polymer (P) and the underwater dissolving chemical agent in a solvent, applying the resultant liquid substance to the surface of a structure such as wall, plate, concrete, or net, then expelling the solvent from the applied layer of the liquid substance, and immersing the structure now coated with the chemical agent composition in water thereby allowing it to fulfil its function, the method which comprises causing the cross-linked polymer (P) to absorb the underwater dissolving chemical agent, enclosing the resultant chemical agent composition with a cloth or net, and immersing the produced package in water thereby allowing the chemical agent to fulfil its function, and the method which comprises packing a cylindrical tube with the chemical agent composition and passing water through the cylindrical tube thereby allowing the chemical agent composition to fulfil its function may be cited, for example.

The composition which results from the mixture of the underwater chemical agent gradual release substrate of this invention with the underwater dissolving chemical agent, when necessary, may incorporate therein suitable additives such as antioxidant, pigment, and perfume.

The underwater antifouling agent composition of this invention is obtained by mixing the cross-linked polymer (P) with the antifouling component.

The antifouling component to be used in this invention may be any of the known antifouling chemical agents including organic copper compounds such as copper naphthenate and copper salts of fatty acids; organic tin compounds such as tributyl tin fumarate, triphenyl tin oxide, and triphenyl tin chloride; phenol type compounds such as alkyl phenols and trichlorophenol; nitrogen compounds such as alkyl pyridiniums and maleimide compounds; organic phosphorus compounds such as tributyl phosphate; and thiuram compounds, organic zinc compounds, and organic fluorine compounds, for example. These antifouling agents may be used either singly or in the form of a combination of two or more members. In these antifouling agents, those which are soluble in oil and exhibit solubility of not less than 1 ppm in water are usable particularly effectively.

Though the mixing ratio of the cross-linked polymer (P) and the antifouling component in this composition is not particularly restricted, it is desired to be such that the cross-linked polymer (P) accounts for a proportion in the range of 2 to 80% by weight and the antifouling component for a proportion in the range of 20 to 98% by weight based on the total amount of the composition. If the amount of the cross-linked polymer (P) to be used is less than 2% by weight, the disadvantage arises that the antifouling component is not completely absorbed in the produced composition but suffered to remain therein in a free state. If this amount of the cross-linked polymer (P) exceeds 80% by weight, the disadvantage ensues that the antifouling component is not released in an amount enough to manifest its antifouling effect.

For the production of the underwater antifouling agent composition of this invention, the method which comprises mixing a solution or dispersion containing the cross-linked polymer (P) with the antifouling component and thereafter expelling the solvent from the resultant mixture, the method which comprises keeping the cross-linked polymer (P) in a pelletized or molded form immersed for a prescribed time in a bath containing the antifouling component thereby causing the cross-linked polymer (P) to absorb the antifouling component and thereafter removing the resultant gelled mass from the bath and using the gelled mass as the antifouling agent composition, or the method which comprises mixing the monomer component destined to form the cross-linked polymer (P) with the antifouling component and polymerizing the resultant monomer solution may be employed, for example. When the cross-linked polymer (P) is caused to absorb the antifouling component, this absorption may be accelerated by applying heat to an extent short of inducing degeneration of the antifouling component or by using a solution having the antifouling component dissolved or dispersed in a solvent.

The antifouling agent composition of this invention, when necessary, may incorporate therein various solvents or suitable additives such as iron oxide red, talc, pigments like titanium dioxide and calcium carbonate, coloring matter, surfactant, and plasticizer which lack the efficacy of an antifouling component and serve the purpose of facilitating the handling of the antifouling component and improving the control of the release of the antifouling component.

The gel-like aromatic agent composition of the present invention is obtained by causing the cross-linked polymer (P) to incorporate therein the perfume component. This production can be easily accomplished, for example, by mixing the cross-linked polymer (P) with the perfume component thereby causing the cross-linked polymer (P) to be swelled with the perfume component and consequently converted into a gel. The absorption of the perfume component by the cross-linked polymer (P) in the resultant mixture may be accelerated by heating this mixture to an extent short of inducing diffusion or degeneration of the perfume component.

The aromatic component to be used in this invention is formed of perfume alone or of a mixture of perfume with an oily diluent. The perfumes which are effectively usable in this invention include natural spices such as jasmine oil and citric oils like lemon oil and lime oil and synthetic perfumes represented by monoterpene type hydrocarbons such as limonene; diterpene type hydrocarbons such as abietene; aromatic hydrocarbons such as Parathimen; terpene type alcohols such as linalool, citronelool, nelol, and 1-menthol; alcohols such as benzyl alcohol and α-phenyl ethanol; aliphatic aldehydes such as decanal; terpene type aldehydes such as citrol, citroneral, and lilal; aromatic aldehydes such as benzaldehyde and cinnamaldehyde; terpene type ketones such as menthone and carbone; aromatic ketones such as p-methyl acetophenone and benzophenone; alicyclic ketones such as α, β, γ-ionone and α, β, γ-ilone; macrocyclic ketones such as muscone and civetone; ethers such as diphenyl ether; cyclic ethers such as rose oxide and linalool oxide; acetals such as cytral dimethyl acetal; carboxylic esters such as isocyalacetate; lactones such as -heptyl butyrolactone; and heterocyclic compounds such as indole and methyl quinoline, for example. These perfumes may be used as freely compounded.

The oily diluent has no particular restriction except for the sole requirement that it should be an oily liquid capable of dissolving the perfume and exhibiting diffusibility at normal room temperature. The oily diluents which are effectively usable herein include paraffin type oils (preferably isoparaffins having approximately 8 to 16 carbon atoms), alcohols, ketones, esters, and ethers, for example. They can be used as mixed in a desired ratio with the perfume.

The mixing ratio of the cross-linked polymer (P) and the perfume component in the produced composition is preferable to be such that the cross-linked polymer (P) accounts for a proportion in the range of 2 to 40% by weight and the perfume component for a proportion in the range of 60 to 98% by weight, based on the total of the amount of the composition. If the amount of the cross-linked polymer (P) to be used is less than 2% by weight, the disadvantage arises that the perfume component is not completely absorbed to swell the cross-linked polymer (P) but suffered to remain in an unaltered form. If this amount of the cross-linked polymer (P) exceeds 40% by weight, the disadvantage ensues that the produced composition is deficient in ability to manifest a lasting effect as an aromatic agent and is liable to give rise to an unduly large residue after use.

For the production of the gel-like aromatic agent composition of this invention, the method which comprises keeping the cross-linked polymer (P) immersed in a large amount of the perfume component at normal room temperature for a prescribed time thereby causing the cross-linked polymer (P) to absorb the perfume component and thereafter removing the resultant gelled mass from the perfume component and using the gel as the aromatic agent composition can be employed advantageously.

The gel-like aromatic agent composition of this invention, when necessary, may incorporate therein suitable additives such as antioxidant, coloring matter, insecticide, and medicine.

The gel-like insectifugal-insecticidal-fungicidal agent composition of this invention is obtained by causing the cross-linked polymer (P) to incorporate therein the volatile active component (Q). For example, the production can be easily accomplished by mixing the cross-linked polymer (P) with the volatile active component (Q) thereby causing the cross-linked polymer (P) to be swelled with the volatile active component (Q) and consequently converted into a gel. The absorption of the volatile active component (Q) by the cross-linked polymer (P) in the resultant mixture may be accelerated by heating this mixture to an extent short of inducing diffusion and degeneration of the volatile active component (Q).

The volatile active component (Q) to be used in this invention is a mixture which comprises at least one member selected from the group consisting of volatile liquid insectifuges, insecticides, and fungicides or at least one member selected from the group consisting of liquid or solid insectifuges, insecticides, and fungicides and a volatile oily diluent.

The volatile active components (Q) which are effectively usable in this invention include pyrethroid type insecticides such as Empenthline; carbamate type insecticides such as 1-naphtyl-N-methyl carbamate, 2,3-dihydro-2,2-dimethyl-7-benzofuranyl-N-methyl carbamate, S-methyl-N-(methyl carbamoyloxy) thioacetimidate, and 2-methyl-2-(methyl thio) propionaldehyde-O-methyl carbamoyloxime; organophosphate type insecticides such as 3-(dimethoxy phosphinyloxy)-N-methyl-cis-crotonamide; insectifugal perfumes such as eugenol and citronelol; fungicides such as Captane and 1-4-dichloro-2,5-dimethoxy benzene; acaricides such as Chlorobenzilate; expellants such as alkyl esters of phthalic acid; and fumigants such as chloropicrin, for example. These insectifuges, insecticides, and fungicides may be used either singly or in the form of a combination of two or more members.

The volatile oily diluent which is used in combination with such insectifugal, insecticidal, and fungicidal agents has no particular restriction except for the sole requirement that it should be an oily liquid capable of dissolving the insectifuge, insecticide, and fungicide and manifesting volatility at normal room temperature. The volatile oily diluents which are usable advantageously herein include kerosene, benzene, toluene, and various paraffins. In these volatile oily diluents, paraffin type hydrocarbons having approximately 8 to 16 carbon atoms are used particularly advantageously in terms of speed of diffusion. The volatile oily diluent can be used as mixed in a desired ratio with the insectifuge, insecticide, and fungicide.

Though the mixing ratio of the cross-linked polymer (P) and the volatile active component (Q) in the composition is not particularly restricted, it is preferable to be such that the cross-linked polymer (P) accounts for a proportion in the range of 2 to 40% by weight and the volatile active component (Q) for a proportion in the range of 60 to 98% by weight. If the amount of the cross-linked polymer (P) to be used is less than 2% by weight, the disadvantage arises that the volatile active component (Q) is not completely absorbed but suffered to remain in an unaltered form. If this amount of the cross-linked polymer (P) exceeds 40% by weight, there ensues the disadvantage that the ability of the composition to retain its insectifugal-insecticidal-fungicidal effect is unduly low and the residue after use is too large to tell the degree of consumption of the efficacy.

For the production of the gel-like insectifugal-insecticidal-fungicidal agent composition of this invention, the method which comprises keeping the cross-linked polymer (P) immersed in a large amount of the volatile active component (Q) at normal room temperature for a prescribed time thereby causing the cross-linked polymer (P) to absorb the volatile active component (Q) and then removing the resultant gelled mass from the volatile active component (Q) and using the gel as the insectifugal-insecticidal-fungicidal agent composition can be employed advantageously.

Optionally, the insectifugal-insecticidal-fungicidal agent composition of this invention, when necessary, may incorporate therein suitable additives such as antioxidant, coloring matter, attractant, and perfume.

The fish-luring agent composition of this invention is obtained by causing the cross-linked polymer (P) to incorporate therein the fish-luring substance. This production can be easily accomplished, for example, by mixing the cross-linked polymer (P) with the fish-luring substance thereby causing the cross-linked polymer (P) to be swelled with the fish-luring substance and consequently converted into a gel. Optionally, the absorption of the fish-luring substance by the cross-linked polymer (P) in the mixture may be accelerated by heating the mixture to an extent short of inducing diffusion and degeneration of the fish-luring substance.

The fish-luring substances which are effectively usable in this invention include fish oils such as sardine oil, saury oil, orange raffy oil, cod liver oil, shark liver oil, squid liver oil, whale oil, and seal oil; animal oils such as beef tarrow, pork lard, and milk fat; vegetable oils such as avocado oil, linseed oil, sesame oil, soybean oil, and corn oil; and natural fats such as insect oil, for example. Further, the fish-luring substances which are soluble in such natural oils and fats as mentioned above and therefore are usable herein include amino acids such as histidine and glutamine, amines such as butyl amine, fatty acids such as caproic acid and lauric acid, nucleic acids such as adenine and adenosine, and phospholipids such as lecitin, for example. These natural oils and fats and fish-luring substances may be used either singly or in the form of a combination of two or more members.

Though the mixing ratio of the cross-linked polymer (P) and the fish-luring substance in the composition is not particularly restricted, it is desired to be such that the cross-linked polymer (P) accounts for a proportion in the range of 2 to 70% by weight and the fish-luring substance for a proportion in the range of 30 to 98% by weight. If the amount of the cross-linked polymer (P) to be used is less than 2% by weight, the disadvantage arises that the fish-luring substance is not completely absorbed but suffered to remain in an unaltered form. If this amount of the cross-linked polymer (P) exceeds 70% by weight, the disadvantage ensues that the fish-luring substance is not dissolved out in an amount enough to manifest a desired fish-luring effect.

For the production of the fish-luring agent composition of this invention, the method which comprises keeping the cross-linked polymer (P) immersed in a large amount of the fish-luring substance at normal room temperature for a prescribed time thereby causing the cross-linked polymer (P) to be swelled with the fish-luring substance and then removing the resultant gelled mass from the fish-luring substance and using the gel as the fish-luring agent composition can be advantageously employed.

The fish-luring agent composition of this invention, when necessary, may further incorporate therein suitable additives such as antioxidant, coloring matter, fluorescing agent, fish meal, insect flour, and perfume.

The solid fuel composition of this invention is obtained by causing the cross-linked polymer (P) to incorporate therein the liquid fuel component. The production can be easily accomplished, for example, by mixing the cross-linked polymer (P) with the liquid fuel component thereby causing the cross-linked polymer (P) to absorb and retain therein the liquid fuel component and consequently assume the form of gel. Optionally, the absorption of the liquid fuel component by the cross-linked polymer (P) in the mixture may be accelerated by heating this mixture to an extent short of inducing diffusion and degeneration of the liquid fuel component.

The liquid fuel component to be used in this invention is a liquid oily organic compound which permits ready ignition at normal room temperature, produces combustion of high energy, and finds popular utility as fuel. Preferably, it is an organic compound whose heat of combustion at 25° C. under normal pressure is not less than 8,000 cal/g.

The liquid fuel components which are effectively usable in this invention include aliphatic hydrocarbons such as n-pentane, iso-pentane, neo-pentane, n-hexane, 2-methyl pentane, 3-methyl pentane, n-heptane, n-octane, 2,2,4-trimethyl pentane, and n-decane; alicyclic compounds such as cyclopentane, cyclohexane, and cycloheptane; aromatic compounds such as benzene, toluene, xylene, ethyl benzene, n-propyl benzene, and isopropyl benzene; alcohol compounds such as hexanol and cyclohexanol; and paraffin compounds such as paraffin and iso-paraffin, petroleums such as light oil, kerosene and gasolin for example, and these liquid fuel component can be used solely or in combination with two or more.

Though the mixing ratio of the cross-linked polymer (P) and the liquid fuel component in the composition is not particularly restricted, it is desired to be such that the cross-linked polymer (P) accounts for a proportion in the range of 2 to 50% by weight and the liquid fuel component for a proportion in the range of 50 to 98% by weight. If the amount of the cross-linked polymer (P) to be used is less than 2% by weight, the disadvantage arises that the complete absorption and retention of the liquid fuel component by the cross-linked polymer (P) is attained only with difficulty and the produced composition retains flowability and provides no sufficient inhibition of the diffusion of the liquid fuel component. If this amount of the cross-linked polymer (P) exceeds 50% by weight, the disadvantage ensues that the produced composition possesses an unduly low fuel component content and incurs difficulty in providing stable lasting generation of a high calorific value.

For the production of the solid fuel composition of this invention, the method which comprises keeping the cross-linked polymer (P) immersed in a large amount of the liquid fuel component thereby causing the cross-linked polymer (P) to absorb and retain therein the liquid fuel component and then removing from the liquid fuel component the gelled mass of the cross-linked polymer (P) swelled with the liquid fuel component can be employed advantageously.

The cross-linked polymer (P) to be used in the solid fuel composition of this invention is capable of absorbing a large amount of the liquid fuel component even at normal room temperature and consequently swelling and forming a gel. When this cross-linked polymer (P) continues to exist during or after the use of the solid fuel composition of this invention, therefore, it can be used repeatedly for the production of the composition by the incorporation therein of the liquid fuel component.

The solid fuel composition of this invention, when necessary, may further incorporate therein a solid fuel such as charcoal or coal briquette. Further, the solid fuel composition of this invention may be used as packed in a non-flammable or inflammable container.

The oil-absorbent material of this invention is obtained by depositing the cross-linked polymer (P) on the hydrophobic porous substrate.

The hydrophobic porous substrate to be used in this invention has no particular restriction except for the requirement that it should be a porous substrate possessing hydrophobicity enough to prevent itself from dissolving in or swelling with water, preferably possessing high oleophilicity enough to adsorb oil, and possessing a large surface area enough to carry the cross-linked polymer (P) effectively thereon and containing voids enough to absorb and retain oil. For example, a substrate formed of synthetic fibers or of natural fibers which have undergone a treatment for impartation of hydrophobicity can be used. For the sake of allowing production of an oil-absorbing material possessing a highly satisfactory oil-absorbing capacity, the substrate is particularly preferable to be a non-woven fabric or a woven fabric which is made of at least one synthetic resin selected from the group consisting of polyolefins such as polypropylene and polyethylene, polyesters, nylons, and polyurethane.

The method to be used for the production of the oil-absorbent material of this invention, therefore, has no parlticular restriction except for the requirement that the cross-linked polymer (P) should be deposited on the hydrophobic porous substrate so fast that it will not separate from the substrate while the oil-absorbent matelrial is in service. The method which comprises causing the cross-linked polymer (P) to be nipped between two opposed hydrophobic porous substrates, the method which comprises preparing a mixture of the cross-linked polymer (P) with hydrophobic fibers or a fleece thereof and molding this mixture in the shape of a sheet thereby allowing the cross-linked polymer (P) to be dispersed and deposited fast within the hydrophobic porous substrate, the method which comprises causing the cross-linked polymer (P) to adhere fast to the hydrophobic porous substrate through the medium of adhesive agent, and the method which comprises causing the monomer component destined to form the cross-linked polymer (P) by polymerization to impregnate the hydrophobic porous substrate and thereafter polymerizing the monomer component on the hydrophobic porous substrate thereby forming the cross-linked polymer (P) on the hydrophobic porous substrate and, at the same time, immobilizing the cross-linked polymer (P) on the substrate may be cited, for example.

For the fast deposition of the cross-linked polymer (P) on the hydrophobic porous substrate, the method which comprises spraying the aforementioned aqueous suspension of the cross-linked polymer (P) obtained by suspension polymerization on the hydrophobic porous substrate, optionally shaking the hydrophobic porous substrate thereby causing the sprayed aqueous suspension to be uniformly dispersed in the texture of the hydrophobic porous substrate, and thereafter drying the resultant wet composite can be advantageously employed. For the purpose of enforcing the fastness of the deposition, the cross-linked polymer (P) and the hydrophobic porous substrate already united by the deposition may be jointly impregnated with an adhesive agent and consequently enabled to adhere fast to each other. Further, the method which comprises mixing the cross-linked polymer (P) with hydrophobic fibers such as of a polyolefin or a fleece thereof and then forming the resultant mixture in the shape of a sheet by the needle punch technique or the spun bond technique which is popularly employed for the production of non-woven fabric can be employed more preferably.

Further for the deposition of the cross-linked polymer (P) on the hydrophobic porous substrate, the method which comprises impregnating the hydrophobic porous substrate with the monomer component and thereafter polymerizing the monomer component as deposited on the substrate is advantageously employed. The impregnation of the hydrophobic porous substrate with the monomer component in this case may be accomplished by mixing the monomer component with a polymerization initiator and blowing the resultant mixture against the substrate by the use of a spray, by applying the mixture to the substrate by the use of a brush or by the known printing technique using a roller or a screen, or by immersing the substrate in the aforementioned mixed solution and thereafter optionally squeezing the wet substrate until the contained solution decreases to a prescribed amount. The polymerization of the monomer component on the substrate may be accomplished by heating or exposing to an ultraviolet light the substrate wet with the monomer component. By this method, the cross-linked polymer (P) formed by the polymerization is allowed to produce a uniform coating on the surface of the hydrophobic porous substrate and add greatly to the surface area of the cross-linked polymer (P) and expedite the absorption of oil. This uniform coating also serves the purpose of minimizing the possibility of the cross-linked polymer (P) leaking or separating from the hydrophobic porous substrate.

Though the amount of the cross-linked polymer (P) to be deposited on the hydrophobic porous substrate in the oil-absorbing material of this invention is not particularly restricted, it is desired to be such that this amount of the cross-linked polymer (P) is in the range of 10 to 500 parts by weight based on 100 parts by weight of the hydrophobic porous substrate. If the amount of the cross-linked polymer (P) to be deposited is less than 10 parts by weight, the disadvantage arises that the produced oil-absorbent material is deficient in ability to absorb oil or in ability to retain the absorbed oil. If this amount of the cross-linked polymer (P) exceeds 500 parts by weight, the disadvantage ensues that the cross-linked polymer (P) plugs the voids in the hydrophobic porous substrate and the oil-absorbing material acquires an inferior oil-absorbing capacity.

The oil mist filter of the presesnt invention is obtained by the deposition of the cross-linked polymer (P) on the porous substrate.

The porous substrate to be used in this invention has no particular restriction except for the requirement that it should be a porous substrate possessing a wide surface area enough to provide effective deposition of the cross-linked polymer (P) and voids enough to allow effective absorption and retention of oil. It may be formed of synthetic fibers or natural fibers, for example. For the purpose of allowing production of an oil mist filter possessing a highly desirable oil-absorbing capacity, the porous substrate is desired to be formed of a non-woven fabric or a woven fabric of at least one synthetic resin selected from the group consisting of polyolefins such as polypropylene and polyethylene, polyesters, nylons, and polyurethane.

The method to be used for the production of the oil mist filter of this invention, therefore, has no particular restriction except for the requirement that it should be capable of depositing the cross-linked polymer (P) on the porous substrate so fast that the cross-linked polymer (P) will not separate from the substrate. The method which comprises nipping the cross-linked polymer (P) between two opposed porous substrates, the method which comprises mixing the cross-linked polymer (P) with a fleece of fibers and molding the resultant mixture thereby allowing the cross-linked polymer (P) to be dispersed and deposited fast in the texture of the porous substrate, the method which comprises causing the cross-linked polymer (P) to adhere fast to the porous substrate through the medium of an adhesive agent, and the method which comprises impregnating the porous substrate with the monomer component destined to form the cross-linked polymer (P) and then polymerizing the monomer component thereby forming the cross-linked polymer (P) on the porous substrate and, at the same time, immobilizing the cross-linked polymer (P) on the substrate may be cited, for example.

For the deposition of the cross-linked polymer (P) on the porous substrate, the method which comprises spraying on the porous substrate an aqueous suspension of the cross-linked polymer (P) obtained by suspension polymerization or emulsion polymerization, optionally shaking the porous substrate thereby inducing uniform dispersion of the sprayed aqueous suspension in the texture of the porous substrate, and thereafter drying the wet porous substrate proves to be particularly preferable among other methods. The cross-linked polymer (P) and the porous substrate already joined by the deposition may be impregnated with adhesive agent for the purpose of reinforcing their mutual adhesion. Further, the method which comprises mixing the cross-linked polymer (P) with hydrophobic fibers such as of a polyolefin or a fleece thereof and thereafter molding the resultant mixture in the shape of a sheet by the needle punch technique or the spun bond technique which has been popularly used for the production of non-woven fabric can be employed more advantageously.

Further, the deposition of the cross-linked polymer (P) on the porous substrate is advantageously accomplished by the method which comprises impregnating the porous substrate with the monomer component and thereafter polymerizing the monomer component on the substrate. The impregnation of the porous substrate with the monomer component in this case may be attained by blowing a mixed solution formed by addition of a polymerization initiator to the monomer component against the substrate by the use of a spray, by applying the mixed solution to the substrate by the use of a brush or by the known printing method using a roller or a screen, or by immersing the substrate in the aforementioned mixed solution and thereafter optionally squeezing the wet substrate until the contained solution is decreased to a prescribed amount. The polymerization of the monomer component on the substrate is accomplished by heating or exposing to an ultraviolet light the substrate wet with the monomer component. By this method, the cross-linked polymer (P) to be formed by the polymerization is enabled to produce a uniform coating on the surface of the porous substrate, add greatly to the surface area of the cross-linked polymer (P), and expedite the absorption of oil mist. The uniform coating further serves the purpose of minimizing the possibility of the cross-linked polymer (P) leaking or separating from the porous substrate.

Though the amount of the cross-linked polymer (P) to be deposited on the porous substrate in the oil mist filter of the present invention is not particularly restricted, it is desired to be such that this amount of the cross-linked polymer (P) is in the range of 2 to 200 parts by weight based on 100 parts by weight of the porous substrate. If the amount of the cross-linked polymer (P) to be deposited is less than 2 parts by weight, the disadvantage arises that the produced oil mist filter is deficient in ability to absorb oil mist. Conversely, if this amount of the cross-linked polymer (P) exceeds 200 parts by weight, the disadvantage ensues that the cross-linked polymer (P) plugs the voids in the porous substrate and, consequently, the filter suffers from clogging and degrades the operational efficiency of a ventilating device or an air circulating device.

The oil mist filter can be put to use, for example, by being fitted in the inlet to the ventilating device or the air circulating device.

The thermosensitive recording material of this invention can be obtained by causing the cross-linked polymer (P) produced as described above to be superposed on a supporting base used for carrying thereon a thermosensitive coloring layer or to be incorporated in the thermosensitive coloring layer.

The method of thermosensitive coloration for which the thermosensitive recording material of this invention can be effectively used is suitably selected from among the known methods, including the method of dye coloration (NCR type) which consists in effecting coloration of a basic colorless dye (chiefly a leuco dye) with a developer formed of a basic substance, the method of metallic compound (3M type) which consists in effecting coloration by the combination of a metallic salt of an organic acid and an electron donating component, and the method which effects coloration of an azo type dye by the reaction thereof with a developer.

The basic colorless dyes which are effectively usable in the method of dye coloration (NCR type) include phthalide type compounds such as 3,3-bis(p-dimethylaminophenyl)-6-dimethylaminophthalide and 3,3-bis(p-dimethylaminophenyl) phthalide; fluoran type compounds such as 3-diethylamino-6-methyl fluoran, 3-diethylamino-6-methyl-7-anilinofluoran, and 3-pyrrolidino-6-methyl-7-anilinofluoran; triphenyl methane type compounds such as 4,4'-bis(dimethylamino)triphenyl methane and 4,4-bis(dimethylamino)triphenyl methanol; phenothiazine type compounds such as 3,7-bis(dimethylamino)-10-benzoyl phenothiazine; and spiropyran type compounds such as 1,3,3-trimethyl indolin-2,2'-spiro-6'-nitro-8'-methoxybenzopyran, for example. The developer to be used in combination with the basic colorless dye is an acidic substance which effects coloration of the basic colorless dye by contact therewith. The developers which are effectively usable herein include bisphenol A, 2,2-bis(4-hydroxyphenyl) n-heptane, 1,1-bis(4-hydroxyphenyl) cyclohexane, p-phenylphenol, resorcin, kaolin, zeolite, activated clay, oxalic acid, maleic acid, stearic acid, citric acid, benzoic acid, and gallic acid, for example.

The metal salts of organic acids which are effectively usable in the method of metal compound (3M type) include ferric stearate, ferric myristate, copper stearate, zinc stearate, nickel acetate, nickel palmitate, and lead myristate, for example. The electron donating components which are effectively usable in combination with the metal salt of organic acid include gallic acid, tannic acid, thiosemicarbazic acid, thio-urea derivatives, thio-oxamide derivatives, and thioacetamide, for example.

The incorporation of the cross-linked polymer (P) in the thermosensitive coloring layer is effected, for example, by the well-known method which comprises uniformly dispersing an aqueous dispersion of the cross-linked polymer (P) obtained by the aforementioned suspension polymerization or emulsion polymerization in a thermosensitive coloring layer-forming liquid thereby forming a uniform dispersion, applying the uniform dispersion to a supporting base, and thereafter drying the applied layer of the dispersion at low temperature. Incidentally, the thermosensitive coloring layer-forming liquid can be prepared, for example, by finely dividing and dispersing the basic colorless dye and the developer mentioned above in the aqueous solution of a protective colloid agent or a low-molecular surfactant formed of such a water-soluble macromolecular substance as polyvinyl alcohol, carboxymethyl cellulose, methyl cellulose, ethyl cellulose, nitrocellulose, hydroxyethyl cellulose, or starch by the use of a ball mill or a sand mill, and optionally adding to the resultant dispersion a binding agent such as a water-soluble polymeric substance or styrene-butadiene latex, a sensitizer such as p-benzyl biphenyl, 2-benzyloxy naphthalene, or stearic acid amide, a shelf life enhancer such as a hindered phenol, zinc acrylate, or an epoxy compound, a filler such as calcium carbonate, aluminum hydroxide, silica, or clay, a defoaming agent, etc. Preferably, the dispersion of the cross-linked polymer (P) in the thermosensitive coloring layer-forming liquid is attained by the method which comprises carrying out the fine division of the basic colorless dye and the developer in the aqueous solution of the water-soluble macromolecular substance and the low-molecular surfactant in the presence of the cross-linked polymer (P) thereby effecting fine division of the cross-linked polymer (P) simultaneously with the fine division of the basic colorless dye and the developer.

For the production of the thermosensitive recording material of this invention by the superposition of the cross-linked polymer (P) on the supporting base carrying thereon the thermosensitive coloring layer, the method which comprises applying an aqueous dispersion of the cross-linked polymer (P) obtained by the aforementioned suspension polymerization or emulsion polymerization or a viscous liquid containing the cross-linked polymer (P) obtained by solution polymerization to the supporting base, drying the applied layer of the aqueous dispersion or aqueous liquid, and then applying to the dried layer the aforementioned thermosensitive coloring layer-forming liquid thereby forming the thermosensitive coloring layer can be employed, for example. The methods which are usable advantageously for the superposition of the cross-linked polymer (P) on the supporting base include the method which comprises applying to the supporting base a monomer component composed of a monomer (A), a monomer (B), and a polymerization initiabor and then polymerizing the monomer component and the method which comprises dissolving the monomer component in a solvent, applying the resultant solution to the supporting base, polymerizing the monomer component in the applied layer of the solution and, after the polymerization is completed, drying the layer thereby expelling the solvent therefrom, for example, can be employed.

Though the amount of the cross-linked polymer (P) to be used relative to the thermosensitive coloring layer is not particularly restricted, this amount of the cross-linked polymer (P) is desired to be in the range of 0.1 to 100% by weight, based on the amount of the thermosensitive coloring layer (the total amount of the components of the thermosensitive coloring layer-forming liquid minus the amount of the cross-linked polymer (P) where the thermosensitive coloring layer contains the cross-linked polymer (P)). If the amount of the cross-linked polymer (P) to be used is less than 0.1% by weight, the disadvantage arises that the produced thermosensitive recording material forms a beautiful recorded image only with difficulty and attains only an inconspicuous improvement in resistance to oil or resistance to solvent. Conversely, if this amount of the cross-linked polymer (P) exceeds 100% by weight, the disadvantage ensues that the thermosensitive coloring layer possibly suffers from a decline of strength and a decline in surface smoothness.

The pressure-sensitive recording sheet of this invention can be produced by causing the cross-linked polymer (P) obtained as described above to be superposed on a supporting base carrying a developer layer thereon or to be incorporated in the developer layer. In terms of structure, the pressure-sensitive recording sheet is represented by a separate type copying pressure-sensitive recording sheet in which a layer containing microcapsules enclosing therein an involatile oily solution of a coloring dye is formed on the lower surface of an upper sheet, a layer incorporating therein a developer is formed on the upper surface of a lower sheet, and the upper sheet and the lower sheet are superposed in such a manner that the microcapsule-containing layer of the upper sheet and the developer containing layer of the lower sheet confront each other. It is also represented by a self-coloring type pressure-sensitive recording sheet in which the microcapsule-containing layer and the developer-containing layer are formed on one common supporting base so that coloration is attained by exertion of pressure on the layers. Thus, this invention can be embodied in various types of pressure-sensitive recording sheets.

The coloring dye to be used as one of the components of the pressure-sensitive recording sheet of this invention is identical to that which is used in the thermosensitive recording sheet described above.

The involatile oily solvents which are usable effectively for dissolving the coloring dye include alkyl naphthalenes such as diisopropyl naphthalene; alkyl biphenyls such as diphenyl methane; triaryl dimethanes such as triphenyl dimetnane; alkyl benzenes; carboxylic esters such as diethyl phthalate; vegetable oils such as castor oil, soybean oil, and cottonseed oil; and high-boiling solvents such as natural mineral oils, for example. These involatile oily solvents may be used either singly or in the form of a combination of two or more members.

Further, the production of the microcapsules enclosing therein an involatile oily solution of a coloring dye (hereinafter referred to a "dye component") can be attained by employing the well-known method heretofore practised for the production of microcapsules. Specifically, the method of coacervation which comprises dispersing the dye component in an aqueous gelatin solution, adding gum arabic to the resultant dispersion, and adjusting the pH value of the produced mixture thereby inducing capsulation, the method of interface polymerization which comprises dispersing in water a mixture of a capsule wall-forming component such as polyisocyanate with the dye component and adding to the produced aqueous dispersion a polyamine or a polyhydric alcohol thereby inducing condensation polymerization of the polyisocyanate with the polyamine or polyhydric alcohol in the oil-water interface and consequent capsulation, the method of in-situ polycondensation which comprises dispersing the dye component in water, adding a melamine/formaldehyde prepolymer to the resultant dispersion, adjusting the pH value of the resultant mixture, and subjecting the mixture to polycondensation and consequently inducing capsulation, the method of in-situ addition polymerization which comprises adding a polyisocyanate and a polyhydriic alcohol to the dye component, dispersing the resultant mixture in water, and subjecting the produced dispersion to addition polymerization by application of heat thereby effecting capsulation, and the method of in-situ radical polymerization which comprises adding a monomer such as acrylonitrile and a polymerization initiator to the dye component, dispersing the resultant mixture in water, and subjecting the aqueous dispersion to radical polymerization thereby inducing capsulation, for example, are available for the production of the microcapsules.

The developer to be used in the present invention is identical to that which is used for the thermosensitive recording material described above.

The formation of the microcapsule-containing layer and the developer-containing layer by the fixation of the microcapsules and the developer on the supporting base is attained, for example, by preparing an aqueous coating liquid optionally by the use of a well-known binder, applying this coating liquid to the supporting base, and drying the applied layer of the coating liquid. The binders which are effectively usable for the preparation of the coating liquid include such macromolecular compounds as polyvinyl alcohol, carboxymethyl cellulose, methyl cellulose, ethyl cellulose, nitrocellulose, hydroxyethyl cellulose, and isobutylene-maleic anhydride copolymer, for example. For the incorporation of the cross-linked polymer (P) in the developer layer, the method which comprises dispersing an aqueous dispersion of the cross-linked polymer (P) obtained by the suspension polymerization or emulsion polymerization described above in a developer coating liquid prepared as generally practised, applying the resultant dispersed mixture to the supporting base, and drying the applied layer of the mixture is available, for example. Besides, the method which comprises pulverizing the cross-linked polymer (P) in water in the presence of a dispersant such as a surfactant and a protective colloid agent formed of a water-soluble macromolecular substance such as polyvinyl alcohol, carboxymethyl cellulose, methyl cellulose, ethyl cellulose, nitrocellulose, hydroxyethyl cellulose, or starch, mixing the produced aqueous dispersion with the developer coating liquid, applying the resultant dispersed mixture to the supporting base, and drying the applied layer of the mixture is similarly available.

For the production of the pressure-sensitive recording sheet of this invention by the superposition of the cross-linked polymer (P) on the supporting base carrying the developer layer thereon, the method which comprises applying an aqueous dispersion of the cross-linked polymer (P) obtained by the suspension polymerization or emulsion polymerization mentioned above or a viscous liquid containing the cross-linked polymer (P) obtained by solution polymerization to the supporting base, drying the applied layer of the aqueous dispersion or aqueous liquid, and thereafter applying the aforementioned well-known developer layer coating liquid to the dried layer thereby forming the developer layer thereon can be adopted. The application of the cross-linked polymer (P) to the supporting base is desirably attained by the method which comprises applying a monomer component composed of a monomer (A), a monomer (B), and a polymerization initiator to the supporting base and then polymerizing the monomer component and the method which comprises dissolving the monomer component in a solvent, applying the produced solution to the supporting base, polymerizing the monomer component in the applied layer of the solution and, after the polymerization is completed, drying the applied layer thereby expelling the solvent therefrom, for example.

The amount of the cross-linked polymer (P) to be used relative to the developer layer is desired to be in the range of 0.1 to 100% by weight, based on the amount of the developer layer (the total amount of the components of the developer layer minus the amount of the cross-linking polymer (P) where the developer layer embraces the cross-linked polymer (P)). If the amount of the cross-linked polymer (P) to be used is less than 0.1% by weight, the disadvantage arises that the pressure-sensitive recording sheet encounters difficulty in forming a beautiful recorded image and attains only an insignificant improvement in resistance to oil or resistance to solvent. Conversely, if this amount of the cross-linked polymer (P) exceeds 100% by weight, the disadvantage ensues that the developer layer possibly suffers from a decline of strength and a decline in surface smoothness.

The oil sealing material of this invention is produced by dispersing the cross-linked polymer (P) as uniformly in the thermoplastic resin and/or rubber as possible. The method to be used for this dispersion is not particularly restricted. Specifically, the method which comprises kneading the cross-linked polymer (P) and the substrate (R) by the use of a conventional mixing device such as kneader, roll, or Banbury mixer, the method which comprises dispersing the cross-linked polymer (P) in a monomer or prepolymer destined to form the substrate (R) and then polymerizing the polymer or curing the prepolymer, and the method which comprises mixing an aqueous dispersion of the cross-linked polymer (P) obtained by emulsion polymerization with an aqueous dispersion of the substrate (R) and then drying the resultant mixture as molded in the shape of film are available for the production, for example.

The substrate (R) in which the cross-linked polymer (P) is dispersed in this invention can be suitably selected from among various kinds of thermoplastic resins and/or elastomers.

The thermoplastic resins which are effectively usable herein include ethylene-vinyl acetate copolymer, saponified ethylene-vinyl acetate copolymer, ethylene-isobutylene copolymer, ethylene-acrylic acid copolymer, ethylene-acrylic ester copolymers, vinyl chloride polymer, polyurethane, polyethylene, polypropylene, polystyrene, ABS resin, polyamides, and polyvinyl acetate, for example.

The elastomers which are effectively usable herein include ethylene-propylene rubber, polybutadiene rubber, polyisoprene rubber, styrene-butadiene copolymer rubber, chloroprene rubber, fluorine rubber, silicone rubber, urethane rubber, polysulfide rubber, acryl rubber, butyl rubber, epichlorohydrin rubber, and natural rubbers, for example.

The mixing ratio of the cross-linked polymer (P) and the substrate (R) in the oil sealing material of this invention cannot be specifically defined because it is variable with the kind of the substrate to be used, the method to be employed for the dispersion of the cross-linked polymer (P), or the purpose for which the sealing material is to be used. Generally, this mixing ratio is desired to be such that the cross-linked polymer (P) accounts for a proportion in the range of 1 to 75% by weight and the substrate (R) for a proportion in the range of 25 to 99% by weight. If the amount of the cross-linked polymer (P) is less than 1% by weight, the disadvantage arises that the oil sealing material does not swell sufficiently on contact with oil and, therefore, manifests only a poor sealing effect. If this amount of the cross-linked polymer (P) exceeds 75% by weight, the disadvantage ensues that the sealing material is deficient in strength and incapable of retaining its shape intact after swelling.

The oil sealing material of this invention, when necessary, may incorporate therein a filler such as carbon black, calcium silicate, calcium carbonate, zinc oxide, or clay, a modifier such as rosin, petroleum resin, cumarone resin, or phenol resin, a vulcanizer such as sulfur or polysulfide rubber, a vulcanization accelerator such as 2-mercaptobenzothiazole or dibenzothiazyl disulfide, stabilizer, antioxidant, pigment, processing auxiliary, or plasticizer.

Further, the oil sealing material of this invention can be formed by various methods such as, for example, the press molding method. It, therefore, can be molded in various shapes such as packings and plugs to suit the purposes of use.

The paper of this invention possessing high printability can be produced by causing the cross-linked polymer (P) obtained as described above to be incorporated in a varying form in paper.

Specifically, the production of the paper of high printability can be accomplished by mixing an aqueous dispersion of the cross-linked polymer (P) obtained by the aforementioned suspension polymerization or emulsion polymerization with pulp as the raw material for paper in an aqueous medium and thereafter molding the resultant dispersed mixture in the shape of sheet. The content of the cross-linked polymer (P) in the paper in this case is desired to be in the range of 0.1 to 20% by weight. If this content is less than 0.1% by weight, the produced paper possesses only a small capacity for absorbing the solvent in the ink and, therefore, exhibits inferior printability. If this content exceeds 20% by weight, the disadvantage arises that the produced paper is deficient in strength. In the production of the paper, the cross-linked polymer (P) may be used in combination with the conventional additives for paper such as, for example, pigment, sizing agent, and paper strength enhancer.

Optionally, a coated paper excelling in printability can be produced by applying to paper a coating liquid containing an aqueous dispersion of the cross-linked polymer (P) and then drying the applied layer of the coating liquid. The coating liquid to be used in this case can be prepared by simply admixing an aqueous dispersion of the cross-linked polymer (P) with an aqueous coating liquid containing well-known active components (pigment such as clay or calcium carbonate, latex binder such as styrene-butadiene type latex, aqueous binder such as starch, and other auxiliaries, for example). The cross-linked polymer (P) is desired to be contained in a proportion in the range of 0.1 to 30% by weight, based on the total amount of the active components of the coating liquid. If this content is less than 0.1% by weight, the coated paper to be produced possesses a small capacity for absorbing the solvent in the ink and, therefore, exhibits inferior printability. If the content exceeds 30% by weight, the disadvantage arises that the coated layer betrays lack of balance and the paper of high quality aimed at inherently by a coated paper is not obtained. Further, since the cross-linked polymer (P) functions additionally as a latex binder, the latex binder contained in the popularly used coating liquid may be substituted by the cross-linked polymer (P).

The oil-absorbent pack of this invention is obtained by packing a bag made of the hydrophobic porous cloth with particles of the cross-linked polymer (P). Though the method to be used for this packing is not particularly restricted, the packing is desired to be effected by the steps of filling a bag of the hydrophobic porous cloth with an aqueous dispersion of the cross-linked polymer (P) obtained by suspension polymerization and then drying the filled bag until excess water is removed by draining.

The hydrophobic porous cloth to be used in this invention has no particular restriction except for the requirement that it should inherently possess hydrophobicity enough to avoid dissolving in or swelling with water, preferably exhibit oleophilicity high enough to allow adsorption of oil, and contain a multiplicity of holes not allowing leakage therethrough of particles of the cross-linked polymer (P) but permitting easy passage therethrough of oil. A cloth made of synthetic fibers or natural fibers which have undergone a treatment for impartation of oleophilicity, for example, can be used. Particularly, for the purpose of providing an oil-absorbent pack which excels in ability to absorb oil, this cloth is desired to be a non-woven fabric or woven fabric made of at least one synthetic resin selected from the group consisting of polyolefins such as polypropylene and polyethylene, polyesters, nylons, and polyurethane.

The shape of the cross-linked polymer (P) used in the oil-absorbent pack of this invention is sphere, preferably having 10 to 2000 μm of an average particle diameter. If the diameter exceeds 2000 μm, surface area of the cross-linked polymer (P) decreases considerably and the oil absorbent pack has low oil-absorbing rate. On the contrary, if the diameter is less than 10 μm, and the oil-absorbent pack has low oil absorbing rate and the cross-linked polymer (P) sometimes leaks from holes of the hydrophobic porous cloth.

The oil absorbing pack of this invention can be used as molded in virtually any desired shape such as cylinder, cube, sphere, or sausage, to suit the purpose of use.

Further, the oil absorbing pack of this invention may contain various oil absorbent or filler such as, for example, rice hull, straw, pulp, cotton, porous lime, porous silica, porous pearlite, or expanded polyurethane foam.

Though the method for manufacturing the oil-absorbent material to be employed for the impregnation of the hydrophobic porous substrate with the monomer component in this invention is not particularly restricted, this impregnation can be attained by blowing the monomer component against the substrate by the use of a spray, by applying the monomer component to the substrate with a brush, by making this application by the conventional printing technique using a roller or a screen, or by immersing the substrate in the monomer component and then optionally squeezing the wet substrate until the amount of the contained monomer component decreases to a prescribed level.

Though the amount of the monomer component to be deposited in the hydrophobic porous substrate is not particularly restricted, it is desired to be in the range of 10 to 500 parts by weight, based on 100 parts by weight of the hydrophobic porous substrate. If the amount of the monomer component so deposited is less than 10 parts by weight, the disadvanrage arises that the produced oil absorbing material is possibly deficient in ability to absorb oil and in ability to retain the absorbed oil. If this amount of the monomer component exceeds 500 parts by weight, the disadvantage ensues that the oil-absorbing cross-linked polymer formed by polymerization plugs the voids in the hydrophobic porous substrate and, consequently, the oil absorbing material possibly suffers from a decline of its capacity for oil absorption.

In the method for manufacturing the oil-absorbent material of this invention, in order for the monomer component deposited on the hydrophobic porous substance to be polymerized, the monomer component as carried on the hydrophobic porous substance must be kept immersed in a hot water bath while the polymerization is in process. When this polymerization is carried out in the air or in an inert gas instead of in the hot water bath, since the polymerization is not easily controlled and the oil-absorbent polymer obtained in process of the polymerization is suffered to assume viscosity partly on its surface, the produced cross-linked polymer fails to acquire the quality fit for an oil absorbing material. As a result, the oil absorbing material obtained by depositing the cross-linked polymer on the hydrophobic porous substrate cannot be produced with high repeatability and the viscosity persisting on the produced oil absorbing material entails a problem of difficulty encountered in the storage or the use of the product.

Though the polymerization conditions of temperature and time involved when the polymerization is performed in the hot water bath are variable with the kind and amount of a polymerization initiator or the kind and composition of the monomer component, the oil absorbing material of this invention can be advantageously produced generally by keeping the monomer component deposited on the substrate immersed for a period of several minutes to several hours in the hot water bath kept at a temperature in the range of 40° to 100° C., preferably 50° to 95° C. More preferably, the oil absorbing material of this invention can be produced more quickly and more uniformly by bubbling an inert gas through the hot water bath thereby keeping the hot water bath free from dissolved oxygen.

From the technical point of view, the water bath to be used in this invention is desired to be filled with hot water. The hot water bath, when necessary, may contain an organic solvent such as ethylene glycol and other additives to an extent short of inducing adverse effects such as dissolution of the monomer component from the hydrophobic porous substrate and deterioration of the quality of the substrate.

The oil absorbent material of this invention which is produced as described above may be put to use immediately after its removal from the hot water bath or may be used after being dried as occasion demands. The drying of the wet oil absorbing material can be effected by any desired method resorting to hot air, microwave, infrared ray, or ultraviolet light, for example.

In this invention, the use of the cross-linked polymer (P) as an absorbent for the oil dissolved in water is accomplished by simply admixing this absorbent with the water containing the dissolved oil thereby allowing the dissolved oil to be absorbed and retained by the absorbent. Specifically, this absorbent can be used by following the known methods (such as the method of contact filtration adsorption, the method of fixed-bed adsorption, and the method of moving-bed adsorption) using such adsorbents as activated carbon and activated alumina for the removal of oil dissolved in water, with necessary modifications.

The oil the absorption of which is aimed at by this invention is not particularly restricted but is expected to be meagerly or sparingly soluble in water. The oils which answer this description include hydrocarbon oils such as pentane, hexane, octane, decane, cyclohexane, benzene, toluene, xylene, ethyl benzene, butyl benzene, dodecyl benzene, styrene, petroleum ether, petroleum benzine, petroleum naphtha, petroleum gasoline, and kerosene; halogenated hydrocarbon oils such as chloroform, carbon tetrachloride, trichloroethane, and trichloroethylene; alcohol oils such as hexanol, octanol, and dodecyl alcohol; phenol oils such as cresol, xylenol, octyl phenol, and nonyl phenol; ether oils such as diethyl ether, dibutyl ether, butyl vinyl ether, and butyl phenyl ether; ketone oils such as hexanone and heptanone; fatty acid oils such as caproic acid and oleic acid; and ester oils such as butyl acetate and amyl acetate, for example.

In accordance with the method of contact filtration adsorption, the cross-linked polymer (P) is required to be mixed by stirring with the polluted water in a mixing tank and, after absorbing the oil, to be separated from the water by filtration or sedimentation. This operation may be carried out batchwise or continuously. The purification of the polluted water is attained more thoroughly by using in this operation a device capable of effecting the required adsorption cyclically or in a multi-stage pattern.

In accordance with the method of fixed-bed adsorption, the cross-linked polymer (P) is required to be used in the form of a packed bed through which the polluted water is passed and, after passing a prescribed amount of the polluted water, to be replaced with a fresh supply. The cross-linked polymer (P) may be used in the series multi-stage pattern or the parallel multi-stage pattern.

In accordance with the method of moving-bed adsorption, the cross-linked polymer (P) is required to absorb the oil till saturation from the polluted water in an absorption column, depart sequentially from the absorption column, undergo regeneration, and return to the absorption column and resume service therein. In this case, the method for effecting the regeneration of the used cross-linked polymer (P) may be selected to suit the kind of oil recovered. For example, the cross-linked polymer (P) which has absorbed a low-boiling oil can be easily regenerated by the heat which is intense enough to vaporize the absorbed oil. The cross-linked polymer (P) which has absorbed a high-boiling oil can be regenerated by extracting the absorbed oil with a low-boiling solvent and subsequently vaporizing the low-boiling solvent by heating.

Preferably, the use of the cross-linked polymer (P) as an absorbent for the oil dissolved in water is accomplished by depositing the cross-linked polymer (P) on a porous substrate and passing the waste water or polluted water through the porous substrate carrying thereon the cross-linked polymer (P). This treatment enables the purification of the polluted water to be effected with high efficiency. The porous substrate to be used in this case is desired to possess hydrophobicity enough to avoid dissolving in or swelling with water, preferably possess high oleophilicity enough to allow adsorption of oil, and further possess a large surface area enough to provide effective deposition of the cross-linked polymer (P) and voids enough to absorb oil and retain the absorbed oil. It may be formed of a non-woven fabric or woven fabric of a synthetic resin selected from the group consisting of polyolefins such as polypropylene and polyethylene, polyesters, nylons, and polyurethane, for example. The deposition of the cross-linked polymer (P) on the porous substrate is accomplished, for example, by blowing a monomer component composed of a monomer (A), a monomer (B), and a polymerization initiator against the porous substrate by the use of a spray, by applying the monomer component to the porous substrate by the use of a brush, by effecting this application by the known technique using a roller or a screen, or by immersing the porous substrate in the monomer component and then optionally squeezing the wet substrate until the amount of the contained monomer component is decreased to a prescribed level and thereafter polymerizing the monomer component deposited on the porous substrate by heating or exposing to an ultraviolet light.

In the method for removing oil dissolved in water of this invention, the cross-linked polymer (P) can be used in combination with such conventional adsorbents as activated carbon, bentonite, and activated silica.

Now, this invention, i.e. the swelling oil-absorbing agent, will be described below with reference to working examples and controls. The examples are intended to be merely illustrative of and not in any sense limitative of the invention.

The term "parts" used in these examples is meant to refer to "parts by weight" unless otherwise specified.

EXAMPLE 1

In a flask having an inner volume of 500 ml and provided with a thermometer, a stirrer, a gas inlet pipe, and a reflux condenser, a solution of 2 parts of completely saponified polyvinyl alcohol (polymerization degree 1,500) and 0.08 part of partially saponified polyvinyl alcohol (polymerization degree 1,000 and saponification value 80%) in 300 parts of water was placed, kept stirred while the gas phase in the flask was displaced with nitrogen gas, and heated to 40° C. as kept covered with a current of nitrogen. Then, a solution comprising 99.823 parts of dodecyl acrylate as monomer (A), 0.177 part of ethylene glycol diacrylate as cross-linkable monomer (B), and 0.5 part of 2,2'-Azobis (2,4-dimethylvaleronitrile) was added at once to the flask interior and the resultant mixture was vigorously stirred at 400 rpm. Subsequently, the flask interior was heated to 70° C. and kept at this temperature for two hours to effect polymerization of the monomer components and the flask interior was further heated to 80° C. and kept at this temperature to complete the polymerization. After the completion of the polymerization, a granular cross-linked polymer consequently produced was separated by filtration, washed with water, and dried at 60° C., to obtain a swelling oil-absorbent agent (1) having particle diameters of 100 to 1,000 μm.

EXAMPLE 2

In a flask having an inner volume of 500 ml and provided with a thermometer, a stirrer, a gas inlet pipe, and a reflux condenser, a solution of 2 parts of completely saponified polyvinyl alcohol (polymerization degree 1,500) and 0.08 part of partially saponified polyvinyl alcohol (polymerization degree 1,000 and saponification value 80%) in 300 parts of water was placed, kept stirred while the gas phase in the flask was displaced with nitrogen, and heated at 40° C. as kept covered with a current of nitrogen. Then, a solution consisting of 99.895 parts of hexadecyl methacrylate as monomer (A), 0.105 part of divinyl benzene as cross-linkable monomer (B), and 0.5 part of benzoyl peroxide was added at once to the flask interior and vigorously stirred at 400 rpm. Subsequently, the flask interior was heated to 80° C. and kept at this temperature for two hours to effect polymerization of the monomer components and the flask interior was further heated to 90° C. and kept at this temperature for two hours to complete the polymerization. After the completion of the polymerization, a granular cross-linked polymer consequently produced was separated by filtration, washed with water, and dried at 60° C., to obtain a swelling oil-absorbent agent (2) having particle diameters of 100 to 1,000 μm.

EXAMPLE 3

A swelling oil-absorbent agent (3) was obtained by following the procedure of Example 2, except that 99.734 parts of decyl acrylate was used as monomer (A) and 0.266 part of 1,6-hexanediol diacrylate was used as cross-linkable monomer (B) instead.

EXAMPLE 4

A swelling oil-absorbent agent (4) was obtained by following the procedure of Example 1, except that the amount of dodecyl acrylate was changed to 92.308 parts and 7.692 parts of polypropylene glycol diacrylate (molecular weight 4,000) was used instead as cross-linkable monomer (B).

EXAMPLE 5

A swelling oil-absorbent agent (5) was obtained by following the procedure of Example 2, except that 59.908 parts of hexadecyl methacrylate and 39.938 parts of butyl methacrylate were jointly used as monomer (A) and 0.154 part of divinyl benzene was used as cross-linkable monomer (B) instead.

Control 1

An oil-absorbent agent for comparison (1) was obtained by following the procedure of Example 1, except that 44.863 parts of dodecyl acrylate and 54.833 parts of styrene were jointly used in the place of 99.823 parts of dodecyl acrylate and the amount of ethylene glycol diacrylate was changed to 0.304 part.

Control 2

An oil-absorbent agent for comparison (2) was obtained by following the procedure of Example 1, except that 44.848 parts of dodecyl acrylate, 14.949 parts of acrylic acid, and 39.866 parts of methyl methacrylate were jointly used in the place of 99.823 parts of dodecyl acrylate and the amount of ethylene glycol diacrylate was changed to 0.337 part.

Control 3

An oil-absorbent agent for comparison (3) was obtained by following the procedure of Example 1, except that 99.770 parts of 2-ethylhexyl acrylate was used in the place of 99.823 parts of dodecyl acrylate and the amount of ethylene glycol diacrylate was changed to 0.230 part.

Control 4

An oil-absorbent agent for comparison (4) was obtained by following the procedure of Example 1, except that 99.869 parts of octadecyl acrylate was used in the place of 99.823 parts of dodecyl acrylate and the amount of ethylene glycol diacrylate was changed to 0.131 part.

Control 5

An oil-absorbent agent for comparison (5) was obtained by following the procedure of Example 2, except that 99.797 parts of t-butyl styrene was used in the place of 99.895 parts of hexadecyl methacrylate and the amount of divinyl benzene was changed to 0.203 part.

Control 6

An oil-absorbent agent for comparison (6) was obtained by following the procedure of Example 2, except that 99.772 parts of t-butyl methacrylate was used in the place of 99.895 parts of hexadecyl methacrylate and the amount of divinyl benzene was changed to 0.228 part.

Control 7

An oil-absorbent agent for comparison (7) was obtained by following the procedure of Example 2, except that 99.780 parts of menthyl methacrylate was used in the place of 99.895 parts of hexadecyl methacrylate and 0.220 part of ethylene glycol dimethacrylate was used in the place of 0.105 part of divinyl benzene.

EXAMPLE 6

The swelling oil-absorbent agents (1) to (5) obtained in Examples 1 to 5, the oil-absorbent agents for comparison (1) to (7) obtained in Controls 1 to 7, and an oil-absorbing agent of polynorbornene rubber were tested for oil-absorbing capacity and water absorbability by the following method.

<Method for evaluation>

A 5 g sample oil-absorbent agent was immersed in a varying oil indicated in Table 1 or water at 20° C., left standing therein for 30 minutes and 24 hours, and then recovered by filtration on a metallic net. The sample was left standing on the metallic net for 30 minutes in order for the part of the oil or water loosely adhering to the sample to flow down thoroughly. Then, the swelled sample was weighed. The absorption ratio (oil absorption ratio or water absorption ratio) of the sample was calculated in accordance with the following formula using the found weight.

Absorption ratio (g/g) = (weight of swelled sample − weight of sample before immersion) − weight of sample before immersion.

The results of the test are shown in Table 1.

TABLE 1

| | Oil absorbing capacity (oil absorption ratio, g/g) | | | | | | | | | |
|---|---|---|---|---|---|---|---|---|---|---|
| | toluene | | n-decane | | kerosin | | B-heavy oil | | carbon tetrachloride | |
| Oil absorbent agent to be evaluated | 30 mins | 24 hrs. | 30 mins | 24 hrs. | 30 mins | 24 hrs. | 30 mins | 24 hrs. | 30 mins | 24 hrs. |
| Oil absorbent agent (1) | 18.7 | 19.1 | 13.8 | 13.9 | 14.2 | 14.3 | 3.1 | 7.9 | 30.3 | 30.5 |
| Oil absorbent agent (2) | 20.0 | 20.3 | 14.3 | 14.8 | 15.8 | 16.4 | 3.4 | 7.9 | 33.8 | 33.9 |
| Oil absorbent agent (3) | 19.8 | 19.9 | 13.3 | 13.5 | 15.5 | 15.9 | 4.5 | 8.1 | 31.0 | 31.4 |
| Oil absorbent agent (4) | 15.8 | 16.2 | 10.0 | 10.5 | 12.0 | 12.8 | 2.3 | 6.9 | 26.7 | 26.7 |
| Oil absorbent agent (5) | 16.4 | 16.9 | 9.6 | 9.6 | 11.5 | 11.8 | 3.5 | 6.6 | 28.8 | 29.1 |
| Oil absorbent agent for comparison (1) | 11.8 | 12.2 | 5.1 | 6.1 | 5.2 | 6.2 | 1.3 | 2.5 | 18.9 | 19.1 |
| Oil absorbent agent for comparison (2) | 1.4 | 1.5 | 0.2 | 0.4 | 0.2 | 0.3 | 0.1 | 0.2 | 2.0 | 3.8 |
| Oil absorbent agent for comparison (3) | 10.8 | 11.6 | 7.7 | 7.7 | 7.7 | 7.8 | 1.8 | 3.9 | 17.8 | 18.5 |
| Oil absorbent agent for comparison (4) | 18.3 | 18.5 | 0.6 | 1.0 | 0.9 | 1.5 | 0.5 | 0.5 | 30.1 | 30.3 |
| Oil absorbent agent for comparison (5) | 15.5 | 16.2 | 11.3 | 12.5 | 12.3 | 13.8 | 1.0 | 1.2 | 26.8 | 27.2 |
| Oil absorbent agent for comparison (6) | 12.5 | 14.1 | 0.8 | 1.0 | 0 | 0.1 | 0.5 | 0.6 | 23.9 | 25.3 |
| Oil absorbent agent for comparison (7) | 14.9 | 15.6 | 7.6 | 8.1 | 10.2 | 11.3 | 3.3 | 5.5 | 24.8 | 25.9 |
| Polynorbornene rubber (Norsolex, product of AP, CdF) | 8.9 | 13.7 | 2.6 | 3.1 | 5.0 | 10.4 | 3.3 | 5.7 | 17.3 | 19.6 |

TABLE 1-continued

|  | Oil absorbing capacity (oil absorption ratio, g/g) | | | | | | | | Water absorbability (water absorption ratio, g/g) | |
| --- | --- | --- | --- | --- | --- | --- | --- | --- | --- | --- |
|  | Dibutyl ether | | Oleic acid | | Octanol | | Soy bean oil | | Water | |
| Oil absorbent agent to be evaluated | 30 mins. | 24 hrs. | 30 mins. | 24 hrs. | 30 mins. | 24 hrs. | 30 mins. | 24 hrs. | 30 mins. | 24 hrs. |
| Oil absorbent agent (1) | 12.4 | 12.9 | 10.9 | 14.7 | 8.9 | 10.3 | 5.2 | 10.3 | 0 | 0 |
| Oil absorbent agent (2) | 13.6 | 13.6 | 10.3 | 15.2 | 6.8 | 9.9 | 5.4 | 10.5 | 0 | 0 |
| Oil absorbent agent (3) | 12.4 | 12.8 | 11.0 | 15.2 | 8.2 | 9.5 | 5.0 | 9.9 | 0 | 0 |
| Oil absorbent agent (4) | 9.2 | 9.2 | 7.8 | 10.6 | 5.6 | 7.6 | 2.9 | 6.1 | 0 | 0 |
| Oil absorbent agent (5) | 9.1 | 9.3 | 5.1 | 9.5 | 4.4 | 6.1 | 3.7 | 7.3 | 0 | 0 |
| Oil absorbent agent for comparison (1) | 4.4 | 5.5 | 1.4 | 2.9 | 1.0 | 3.1 | 0.4 | 1.4 | 0 | 0 |
| Oil absorbent agent for comparison (2) | 0.8 | 1.0 | 2.1 | 3.5 | 1.0 | 2.1 | 0.3 | 0.5 | 0.3 | 0.7 |
| Oil absorbent agent for comparison (3) | 7.8 | 8.5 | 4.2 | 5.7 | 3.0 | 4.2 | 0.6 | 2.1 | 0 | 0 |
| Oil absorbent agent for comparison (4) | 3.3 | 4.0 | 0.3 | 0.5 | 0.5 | 0.7 | 0.5 | 0.5 | 0 | 0 |
| Oil absorbent agent for comparison (5) | 12.1 | 12.6 | 0.1 | 0.4 | 0.1 | 0.3 | 0.4 | 0.5 | 0 | 0 |
| Oil absorbent agent for comparison (6) | 5.0 | 5.7 | 0.1 | 0.3 | 0 | 0.2 | 0.5 | 0.5 | 0 | 0 |
| Oil absorbent agent for comparison (7) | 7.9 | 8.7 | 6.3 | 8.2 | 3.1 | 5.4 | 0.4 | 0.6 | 0 | 0 |
| Polynorbornene rubber (Norsolex, product of AP, CdF) | 2.8 | 4.2 | 0.6 | 1.5 | 0.2 | 1.0 | 0.5 | 0.7 | 0 | 0 |

It is clearly noted from Table 1 that the swelling oil-absorbent agents conforming with this invention were able to absorb very quickly a large amount of an oil of widely varying kind.

EXAMPLE 7

A 5 g sample of each of the swelling oil-absorbent agents (1) to (5) obtained in Examples 1 to 5, the oil-absorbent agents for comparison (1) to (7) obtained in Controls 1 to 7, and polynorbornene rubber was immersed in toluene and n-decane at 5° C. and −10° C., left standing therein for 24 hours, and then recovered at the same temperature by filtration on a metal net. The sample was left standing on the metal net for 30 minutes in order for the part of the oil loosely adhering to the sample to flow down thoroughly. The swelled sample consequently obtained was weighed. The absorption ratio of the sample was calculated in accordance with the same formula as shown in Example 6, using the found weight.

The results of the test are shown in Table 2.

TABLE 2

|  |  | Absorbability (g/g) | |
| --- | --- | --- | --- |
| Oil absorbent agent to be evaluated | Temperature (°C.) | toluene | n-decane |
| Oil aborbent agent (1) | 5 | 17.9 | 12.6 |
|  | −10 | 16.9 | 10.9 |
| Oil aborbent agent (2) | 5 | 15.3 | 10.8 |
|  | −10 | 10.1 | 7.7 |
| Oil aborbent agent (3) | 5 | 18.7 | 12.4 |
|  | −10 | 17.2 | 11.5 |
| Oil aborbent agent (4) | 5 | 13.0 | 8.9 |
|  | −10 | 11.6 | 6.5 |
| Oil aborbent agent (5) | 5 | 14.9 | 8.0 |
|  | −10 | 12.2 | 6.0 |
| Oil aborbent agent for comparison (1) | 5 | 2.2 | 1.2 |
|  | −10 | 1.9 | 0.1 |
| Oil aborbent agent for comparison (2) | 5 | 0.5 | 0.2 |
|  | −10 | 0.1 | 0.1 |
| Oil aborbent agent for comparison (3) | 5 | 8.5 | 5.6 |
|  | −10 | 6.3 | 3.9 |
| Oil aborbent agent for comparison (4) | 5 | 10.1 | 0.4 |
|  | −10 | 5.5 | 0.2 |
| Oil aborbent agent for comparison (5) | 5 | 12.6 | 8.8 |
|  | −10 | 8.6 | 2.5 |
| Oil aborbent agent for comparison (6) | 5 | 8.4 | 0.1 |
|  | −10 | 3.0 | 0 |
| Oil aborbent agent for comparison (7) | 5 | 13.8 | 7.3 |
|  | −10 | 12.7 | 6.4 |
| Polynorbornene rubber (Norsolex, product of AP, CdF) | 5 | 9.6 | 2.3 |
|  | −10 | 6.9 | 1.1 |

It is noted from Table 2 that the swelling oil-absorbent agents conforming with this invention exhibited highly satisfactory oil-absorbing capacity at low temperatures.

EXAMPLE 8

A mixed solution comprising 99.823 parts of dodecyl acrylate as monomer (A), 0.177 part of ethylene glycol diacrylate as cross-linkable monomer (B), and 0.1 part of 2,2'-azobis(2,4-dimethyl valeronitrile) as a polymerization initiator was poured in a cast polymerization die (15×15×0.5 cm) made of glass and provided with a thermometer and a gas inlet pipe, heated therein as kept swept with nitrogen gas at 50° C. for two hours to effect polymerization of the monomer components, and then heated to 80° C. and kept at this temperature for two hours to complete the polymerization. The resultant polymerization system was left cooling. A gelled mass consequently formed was separated from the die, to obtain a plate-like cross-linked polymer (1).

A substrate of this invention formed of the cross-linked polymer (1) and intended for underwater gradual release of a chemical agent was impregnated with oleic acid (insecticide) by being immersed therein at normal room temperature for seven days, to obtain a gradual-release chemical agent composition (1). This gradual-release chemical agent composition (1) had an oleic acid content of 91.0% by weight.

EXAMPLE 9

In a flask having an inner volume of 500 ml and provided with a thermometer, a stirrer, two dropping funnels, a gas inlet pipe, and a reflux condenser, 100 parts of toluene was placed and, subsequent to displacement of the gaseous phase in the flask with nitrogen, heated to 80° C. as kept covered with a current of nitrogen. Then, to the toluene which was kept at the same temperature under the current of nitrogen, a monomer mixture solution comprising 187.13 parts of dodecyl acrylate as monomer (A), 12.864 parts of tetraethylene glycol dimethacrylate as cross-linkable monomer (B), and 50 parts of toluene was added dropwise through one of the dropping funnels over a period of 120 minutes and, at the same time, a polymerization initiator solution comprising 1.5 parts of 2,2'-azobis(2,4-dimethyl valeronitrile) and 48.5 parts of toluene was added dropwise through the other dropping funnel over a period of 180 minutes. After the dropwise addition was completed, the resultant mixture was heated at the same temperature for 60 minutes to complete polymerization of the monomer components. The resultant viscous liquid containing the cross-linked polymer (2) resulting from the polymerization had a cross-linked polymer (2) content of 50.0% by weight.

Twenty (20) parts of the viscous liquid containing the cross-linked polymer (2) was mixed with 20 parts of dibutyl phthalate (fungicide). The resultant mixed solution was applied in a thickness of 1 mm to one surface of a polyethylene sheet 5 cm × 2 cm in surface area and the applied layer of the mixed solution was dried to expel the contained toluene and obtain on the polyethylene sheet a coating comprising an underwater chemical agent gradual-release substrate formed of the cross-linked polymer (2) and a gradual-release chemical agent composition (2) formed of dibutyl phthalate. The amount of the gradual-release chemical agent composition (2) applied to the polyethylene sheet was 0.65 g.

EXAMPLE 10

In a flask having an inner volume of 500 ml and provided with a thermometer, a stirrer, a gas inlet pipe, two dropping funnels, and a reflux condenser, 3 parts of polyoxyethylene (polymerization degree 17) monononylphenyl ether and 100 parts of water were placed, stirred at 300 rpm while the gaseous phase in the flask was substituted with nitrogen, and heated to 70° C. as kept covered with a current of nitrogen. Then, to the resultant solution which was kept at the same temperature as covered with the current of nitrogen, 50.6 parts out of 253 parts of an aqueous monomer dispersion obtained by mixing a monomer consisting of 49.519 parts of decyl methacrylate and 49.519 parts of hexadecyl methacrylate as monomer (A) and 0.962 part of 1,6-hexanediol dimethacrylate as cross-linkable monomer (B) with an aqueous solution of 3 parts of polyoxyethylene (polymerization degree 17) monononylphenyl ether in 150 parts of water by the use of a homogenizer at 500 rpm for ten minutes and 5 parts out of 51 parts of an aqueous solution of 1 part of sodium persulfate in 50 parts of water were added at once severally through the two dropping funnels. Subsequently, the remaining aqueous monomer dispersion was added dropwise over a period of 120 minutes and, at the same time, the remaining aqueous sodium persulfate solution was added dropwise over a period of 240 minutes. After the dropwise addition was completed, the resultant mixture was kept standing at the same temperature for 120 minutes to complete polymerization of the monomer components, to obtain an aqueous dispersion of a cross-linked polymer (3). The cross-linked polymer (3) had an average particle diameter of 0.2 μm and the aqueous dispersion had a cross-linked polymer (3) content of 25.3% by weight. Forty (40) parts of the aqueous dispersion containing the cross-linked polymer (3) was vigorously mixed with 20 parts of o-dichlorobenzene (insecticide-fungicide). The resultant mixed solution was applied in a thickness of 1 mm to one surface of a vinyl chloride sheet 5 cm × 2 cm in surface area and the applied layer of the mixed solution was dried to expel the contained water and obtain on the vinyl chloride sheet a coat comprising an underwater chemical agent gradual-release substrate formed of the cross-linked monomer (3) and a gradual-release chemical agent composition (3) of o-dichlorobenzene. The amount of the gradual-release chemical agent composition (3) applied to the vinyl chloride sheet was 0.5 g.

Control 8

A cross-linked polymer for comparison (1) was obtained by following the procedure of Example 8, except that the amount of dodecyl acrylate was changed to 77.922 parts and that of ethylene glycol diacrylate to 22.078 parts respectively.

A chemical agent composition for comparison (1) was obtained by keeping the cross-linked polymer for comparison (1) immersed in oleic acid at normal room temperature for seven days. During this immersion, however, the cross-linked polymer for comparison (1) was not swelled. The chemical agent composition for comparison (1) had an oleic acid content of 2.1% by weight.

Control 9

A cross-linked polymer for comparison (2) was obtained by following the procedure of Example 8, except that 39.884 parts of dodecyl acrylate and 59.826 parts of hydroxyethyl acrylate were used in the place of 99.778 parts of dodecyl acrylate and the amount of ethylene glycol diacrylate was changed to 0.290 part.

A chemical agent composition for comparison (2) was obtained by keeping the cross-linked polymer for comparison (2) immersed in oleic acid at normal room temperature for seven days. During the immersion, the cross-linked polymer for comparison (2) was not conspicuously swelled. This chemical agent composition for comparison (2) had an oleic acid content of 15.2% by weight.

Control 10

A solution containing a polymer for comparison (3) was obtained by following the procedure of Example 9, except that the use of tetraethylene glycol dimethacrylate was omitted.

The resultant solution containing the polymer for comparison (3) was mixed with dibutyl phthalate and the produced mixed solution was applied to a polyethylene sheet and the applied layer of the mixed solution was dried in the same manner as in Example 9 to expel the contained toluene and obtain on the polyethylene sheet a coat of the chemical agent composition for comparison (3) comprising the polymer for comparison (3) and dibutyl phthalate. The amount of the chemical agent composition for comparison (3) applied to the polyethylene sheet was 0.65 g.

EXAMPLE 11

10 g samples of each of the gradual-release chemical agent composition (1) obtained in Example 8 and the chemical agent compositions for comparison (1) and (2) obtained Controls 8 and 9 were each packed in a bag of non-woven fabric of polyester and were simultaneously immersed under sea water to a depth of 1 m below the surface. With 15 days' intervals following the start of the immersion, the six bags containing the chemical agent composition were removed one at a time and the chemical agent composition removed from each of the bags was subjected to Soxhlet extraction using tetrahydrofuran. The extract was analyzed by gas chromatography to determine the chemical agent content remaining in the chemical agent composition. Then, the release ratio of the chemical agent content was calculated in accordance with the following formula. The results are shown in Table 3.

Release ratio (%) = [1 − (amount of chemical agent remaining after immersion/amount of chemical agent before immersion)] × 100

TABLE 3

| Chemical agent composition to be evaluated | Release ratio (%) Time for immersion in sea water (day) | | | | | | |
|---|---|---|---|---|---|---|---|
| | 0 | 15 | 30 | 45 | 60 | 75 | 90 |
| Gradual-release chemial agent compositon (1) | 0 | 25 | 36 | 46 | 57 | 65 | 75 |
| chemical agent composition for comparison (1) | 0 | 100 | 100 | 100 | 100 | 100 | 100 |
| chemical agent composition for comparison (2) | 0 | 92 | 100 | 100 | 100 | 100 | 100 |

EXAMPLE 12

Six polyethylene or vinyl chloride sheets coated with each of the gradual-release chemical agent compositions (2) and (3) obtained in Examples 9 and 10 and the chemical agent composition for comparison (3) obtained in Control 10 were immersed in a fresh water pool 50 m × 20 m in surface area and 1 m in depth. With 15 days' intervals following the start of the immersion, the six sheets coated with the chemical agent composition were removed one at a time and the chemical agent composition removed from each of the sheets was subjected to Soxhlet extraction using tetrahydrofuran. The extract was analyzed by gas chromatography to determine the chemical agent content remaining in the chemical agent composition. The release ratio of the chemical agent content was calculated in accordance with the following formula. The results are shown in Table 4.

Release ratio (%) = [1 − (amount of chemical agent remaining after immersion/amount of chemical agent before immersion)] ×100

TABLE 4

| Chemical agent composition to be evaluated | Release ratio (%) Time for immersion in fresh water (day) | | | | | | |
|---|---|---|---|---|---|---|---|
| | 0 | 15 | 30 | 45 | 60 | 75 | 90 |
| Gradual-release chemial agent composition (2) | 0 | 30 | 46 | 58 | 69 | 79 | 86 |
| Gradual-release chemial agent composition (3) | 0 | 40 | 56 | 67 | 78 | 87 | 94 |
| chemical agent composition for comparison (3) | 0 | 70 | 92 | 100 | 100 | 100 | 100 |

EXAMPLE 13

In a flask having an inner volume of 500 ml and provided with a thermometer, a stirrer, two dropping funnels, a gas inlet pipe, and a reflux condenser, 100 parts of toluene was placed, stirred while the gaseous phase in the flask was displaced with nitrogen, and heated to 80° C. as kept covered with a current of nitrogen. Then, to the toluene which was kept at the same temperature under the current of nitrogen, a monomer mixture solution comprising 189.80 parts of dodecyl acrylate as monomer (A), 10.20 parts of triethylene glycol diacrylate as cross-linkable monomer (B), and 50 parts of toluene was added dropwise through one of the two dropping funnels over a period of 120 minutes and, at the same time, a polymerization initiator solution comprising 1.5 parts of 2,2'-azobis(2,4-dimethyl valeronitrile) and 48.5 parts of toluene was added dropwise through the other dropping funnel over a period of 180 minutes. After the dropwise addition was completed, the resultant mixture was left standing at the same temperature for 60 minutes to complete polymerization of the monomer components.

The resultant viscous liquid containing the produced cross-linked polymer (4) had a cross-linked polymer (4) content of 50.0% by weight. An underwater antifouling agent composition (1) was obtained by mixing 50.0 parts of the viscous liquid containing the cross-linked polymer (4) with 25.0 parts of copper naphthenate and 175.0 parts of xylene.

EXAMPLE 14

An underwater antifouling agent composition (2) was obtained by vigorously mixing 98.8 parts of an aqueous dispersion containing the cross-linked polymer (3) obtained in Example 10 with a solution of 25.0 parts of tributyltin oxide in 126.2 parts of xylene.

EXAMPLE 15

A mixed solution comprising 99.823 parts of dodecyl acrylate as monomer (A), 0.177 part of ethylene glycol diacrylate as cross-linkable monomer (B), and 0.1 part of 2,2'-azobis(2,4-dimethyl valeronitrile) as a polymerization initiator was poured in a cast polymerization die (30×30×0.1 cm) made of glass and provided with a thermometer and a gas inlet pipe, heated at 50° C. as kept covered with a current of nitrogen for two hours to effect polymerization of the monomer components, and then heated to 80° C. and kept standing at this temperature for two hours to complete the polymerization. The resultant polymerization system was left cooling and subsequently separated from the die, to obtain a sheet-like cross-linked polymer (5).

An underwater antifouling agent composition (3) was obtained by swelling the cross-linked polymer (5) with tributyltin oxide by being kept immersed in the tributyltin oxide at normal room temperature for seven days. This underwater antifouling composition (3) had a tributyltin oxide content of 88.0% by weight.

Control 11

A toluene solution containing 50.0% by weight of a polymer for comparison (4) was obtained by following the procedure of Example 13, except that 200.00 parts of dodecyl acrylate was used as monomer (A) and the use of a cross-linkable monomer (B) was omitted.

An antifouling agent composition for comparison (1) was obtained by mixing 50.0 parts of the solution containing the polymer for comparison (4) with 25.0 parts of copper naphthenate and 175.0 parts of xylene.

Control 12

An aqueous dispersion containing 25.2% by weight of a cross-linked polymer for comparison (5) was obtained by following the procedure of Example 14, except that 37.50 parts of decyl methacrylate and 37.50 parts of hexadecyl methacrylate were used as monomer (A) and 25.00 parts of 1,6-hexanediol dimethacrylate was used as cross-linkable monomer (B).

An antifouling agent composition for comparison (2) was obtained by vigorously mixing 99.2 parts of an aqueous dispersion containing the cross-linked polymer for comparison (5) with a solution of 25.0 parts of tributyltin oxide in 125.8 parts of xylene.

EXAMPLE 16

A sample was prepared by applying each of the underwater antifouling agent compositions (1) to (2) and the antifouling agent compositions for comparison (1) and (2) obtained respectively in Examples 13 to 14 and Controls 11 and 12 to a FRP sheet 20×30 cm in surface area in an amount calculated to form a dry layer 1 mm in thickness and subsequently drying the applied layer of the antifouling agent composition. The sample was kept immersed in sea water at a depth of 1 m from the surface and then kept under observation as to the adhesion of organisms to the sample.

The efficacy of the antifouling agent composition of the sample was evaluated by finding the proportion of the surface of the sample covered with the adhering organisms and rating this proportion on the following six-point scale. The results of the evaluations conducted each after three months, six months, and nine months following the start of the immersion are shown in Table 5.

0: Less than 5% of surface area of adhesion
1: 5 to 20% of surface area of adhesion
2: 20 to 40% of surface area of adhesion
3: 40 to 60% of surface area of adhesion
4: 60 to 80% of surface area of adhesion
5: Not less than 80% of surface area of adhesion

EXAMPLE 17

A sample was prepared by cutting a part 20×30 cm in surface area from the sheet-like underwater antifouling agent composition (3) obtained in Example 15 and attaching the cut part fast to a FRP sheet 20×30 cm in surface area. This sample was subjected to an immersion test under sea water by following the procedure of Example 16. The results are shown in Table 5.

TABLE 5

| Kind of antifouling agent composition | Immersion time | | |
|---|---|---|---|
| | 3 months | 6 months | 9 months |
| Antifouling agent composition (1) | 0 | 0 | 0 |
| Antifouling agent composition (2) | 0 | 0 | 0 |
| Antifouling agent composition (3) | 0 | 0 | 0 |
| Antifouling agent composition for comparision (1) | 2 | 3 | 5 |
| Antifouling agent composition for comparision (2) | 2 | 3 | 5 |

EXAMPLE 18

A cross-linked polymer (6) was obtained by following the procedure of Example 15, except that a cast polymerization die (shaped like a tray measuring 5×5×1 cm) made of glass and provided with a thermometer and a gas inlet pipe was used instead.

A transparent gel-like aromatic agent composition (1) was obtained by swelling the cross-linked polymer (6) with an aroma component formed of an orange type perfume by being kept immersed in the aroma component at normal room temperature for seven days. The gel-like aromatic agent composition (1) had an aromatic component content of 92.7% by weight.

Control 13

A cross-linked polymer for comparison (6) was obtained by following the procedure of Example 18, except that 39.854 parts of dodecyl acrylate and 59.780 parts of methacrylic acid were used in the place of 99.823 parts of dodecyl acrylate as monomer (A) and the amount of ethylene glycol diacrylate was changed to 0.366 part.

A translucent aromatic agent composition for comparison (1) was obtained by keeping the cross-linked polymer for comparison (6) in an aromatic component formed of an orange type perfume at normal room temperature for seven days. During this immersion, however, the cross-linked polymer for comparison (6) was not notably swelled. This aromatic agent composition for comparison (1) had an aromatic component content of 45.5% by weight.

Control 14

A cross-linked polymer for comparison (7) was obtained by following the procedure of Example 18, except that the use of a cross-linkable monomer (B) was omitted.

When the produced cross-linked polymer for comparison (7) was kept immersed in an aromatic component formed of an orange type perfurme at normal room temperature for seven days, the cross-linked polymer for comparison (7) was dissolved into the aromatic component and failed to form a gelled mass.

EXAMPLE 19 (Test for transparency)

The gel-like aromatic component composition (1) obtained in Example 18 and the aromatic agent composition for comparison (1) obtained in Control 13 were each compressed or cut to form a sheet 10 mm in thickness.

The sheet was superposed on a white paper bearing letters inscribed with 3 mm types and tested for transparency by deciphering the letters on the white paper through the sheet. The transparency was rated on the following four-point scale. The results are shown in Table 6.

⊙ - Letters deciphered clearly
- Letters slightly blurred
Δ - Letters heavily blurred
X - Letters not deciphered at all

EXAMPLE 20 (TEST FOR DIFFUSIBILITY)

In a tall beaker having an inner volume of 200 ml, a 100 g sample of each of the gel-like aromatic agent composition (1) and the aromatic agent composition for comparison (1) obtained respectively in Example 18 and Control 13 was placed, left standing therein indoors at normal room temperature, and weighed after one, two, three, and four weeks' standing to determine the remaining amount of the aromatic component. Then, the diffusion ratio of the aromatic component was calculated in accordance with the following formula. The results are shown in Table 6.

Diffusion ratio (%) = (Weight of diffused aromatic component/initial weight of aromatic component) × 100

EXAMPLE 21 (TEST FOR STABILITY OF AROMATIC TONE)

The samples which had just undergone weighing in the course of the test for diffusibity described above were subjected to a sensory test for aroma by a panel of 10 members. The aroma was rated on the basis of the total of points given by the members of the panel in accordance with the scale shown below. The results of this test are shown in Table 6.

0 point - Complete difference from inherent aroma 1 point - Loss of freshness and slight difference from in herent aroma 2 points—Slight loss of freshness 3 points - No change linked polymer (7) of Example 22 immersed at room temperature for seven days in a fungicidally active component prepared by mixing 10 parts of p-chloro-m-xylenol with 90 parts of kerosene so as to be swelled therewith. This gel-like insectifugal-insecticidal-fungicidal agent composition (2) had a fungicidally active component content of 91.8% by weight.

Control 15

A cross-linked polymer for comparison (8) was obtained by following the procedure of Example 22, except that 39.854 parts of dodecyl acrylate and 59.780 parts of methacrylic acid were used in the place of 99.823 parts of dodecyl acrylate and the amount of ethylene glycol diacrylate was changed to 0.366 part.

An insectifugal-insecticidal-fungicidal agent composition for comparison (1) was produced by keeping this cross-linked polymer for comparison (8) immersed at normal room temperature for seven days in an insecticidally active component. During this immersion, however, the cross-linked polymer for comparison (8) was not conspicuously swelled. This insectifugal-insecticidal-fungicidal agent composition for comparison (1) had an insecticidally active component content of 48.7% by weight.

Control 16

An insectifugal-insecticidal-fungicidal agent composition for comparison (2) was produced by keeping the cross-linked polymer for comparison (8) of Control 15 immersed at normal room temperature for seven days in a fungicidally active component prepared by mixing 10 parts of p-chloro-m-xylenol with 90 parts of kerosene. During this immersion, however, the cross-linked polymer for comparison (8) was not conspicuously swelled. This insectifugal-insecticidal-fungicidal agent composition for comparison (2) had an insecticidally active component content of 41.1% by weight.

TABLE 6

| Aromatic agent composition | Transparency | Diffusibility (%) | | | | Stability of aromatic tone (point) | | | |
|---|---|---|---|---|---|---|---|---|---|
| | | after 1 week | after 2 weeks | after 3 weeks | after 4 weeks | after 1 week | after 2 weeks | after 3 Weeks | after 4 weeks |
| Gel-like aromatic agent composition (1) | ⊙ | 37 | 58 | 69 | 80 | 30 | 30 | 28 | 24 |
| Aromatic agent composition for comparison (1) | Δ | 51 | 71 | 90 | 94 | 21 | 10 | 0 | 0 |

EXAMPLE 22

A cross-linked polymer (7) was obtained by following the procedure of Example 15, except that a cast polymerization die (shaped after a tray measuring 15×15×0.5 cm) made of glass and provided with a thermometer and a gas inlet pipe was used instead.

A transparent gel-like insectifugal-insecticidal-fungicidal agent composition (1) was produced by keeping this cross-linked polymer (7) immersed at normal room temperature for seven days in an insecticidally active component prepared by mixing 5 parts of Empenthline with 95 parts of kerosene so as to be swelled therewith. This gel-like insectifugal-insecticidal-fungicidal agent composition (1) had an insecticidally active component content of 92.1% by weight.

EXAMPLE 23

A transparent gel-like insectifugal-insecticidal-fungicidal agent composition (2) was produced by keeping the cross-

Control 17

A cross-linked polymer for comparison (9) was obtained by following the procedure of Example 22, except that the use of the cross-linkable monomer (B) was omitted.

When the cross-linked polymer for comparison (9) was kept immersed at normal room temperature for seven days in an insecticidally active component prepared by mixing 5 parts of Empenthline with 95 parts of kerosene, the cross-linked polymer for comparison (9) was dissolved in the insecticidally active component and no gelled mass was produced.

EXAMPLE 24 (TEST FOR DIFFUSIBILITY)

Samples cut in a fixed size of 100 g severally from the gel-like insectifugal-insecticidal-fungicidal agent compositions (1) and (2) and insectifugal-insecticidal-fungicidal agent compositions for comparison (1) and (2) obtained respectively in Examples 22 and 23 and Controls 15 and 16 were placed one each in tall beakers having an inner volume of 200 ml, left standing therein indoors at normal room temperature, and weighed after one, two, four, and six months' standing to determine the residual amounts of the insectifugal-insecticidal-fungicidal component. Then, the ratios of diffusion of insectifugal-insecticidal-fungicidal component from the samples were calculated in accordance with the following formula. The results are shown in Table 7.

Radio of diffusion (%) = (weight of diffused insectifugal-insecticidal-fungicidal component/initial weight of insectifugal-insecticidal-fungicidal component) × 100

EXAMPLE 25 (TEST FOR INSECTICIDAL EFFECT)

Samples cut in a fixed size of 30 g severally from the gel-like insectifugal-insecticidal-fungicidal agent compositions (1) and the insectifugal-insecticidal-fungicidal agent composition for comparison (1) obtained respectively in Example 22 and Control (1) were placed one each in aluminum petri dishes (50 mm in diameter) and left standing in clothes cases (72 liters in inner volume) made of polyethylene at normal room temperature for four months.

Subsequently, specimens prepared by placing five larvae of family Tineoidea and 2 g of feather in a sample vial having an inner volume of 140 ml and made of glass and covering the upper opening of the vial with a 200-mesh metallic gauze were placed one each in the clothes cases. For the subsequent three months, the changes in weight of the feather were measured. The insecticidal effects of the samples were calculated in accordance with the following formula. With intervals of one month, the vials were replenished with five larvae to allow continuation of the test. The results are shown in Table 8.

Insecticidal effect (%) = (weight of feather after placement of specimen in clothes case/initial weight of feather) × 100

EXAMPLE 26 (TEST FOR FUNGICIDAL EFFECT)

Samples cut in a fixed size of 30 g severally from the gel-like insectifugal-insecticidal-fungicidal agent composition (2) and the insectifugal-insecticidal-fungicidal agent composition (2) obtained respectively in Example 23 and Control 16 were placed one each in aluminum petri dishes (50 mm in diameter) and left standing therein at normal room temperature for four months.

After the standing, the samples were placed one each in wide-mouthed vials (5 liters in inner volume) made of polypropylene and, at the same time, petri dishes containing a culture medium inoculated with green mold were placed in the vials. After 72 hours' standing at 40° C., the conditions of growth of the green mold were visually examined and the fungicidal effects of the samples were evaluated on the following scale. The results are shown in Table 9

○: Absolutely no growth observed

Δ: Slight growth observed

X: Growth throughout entire surface of culture medium inpetri dish observed

TABLE 7

| Insectifugal-insecticidal-fungicidal composition | Diffusibility (%) | | | |
|---|---|---|---|---|
| | After 1 month | After 2 months | After 4 months | After 6 months |
| Gel like insectifugal-insecticidal-fungicidal composition (1) | 15 | 29 | 63 | 88 |
| Gel like insectifugal-insecticidal-fungicidal composition (2) | 14 | 30 | 64 | 87 |
| Insectifugal-insecticidal-composion for comparison (1) | 29 | 54 | 79 | 96 |
| Insectifugal-insecticidal-composion for comparison (2) | 31 | 56 | 80 | 95 |

TABLE 8

| Insectifugal-insecticidal-fungicidal composition | Insecticidal effect (%) | | |
|---|---|---|---|
| | After 1 month | After 2 months | After 3 months |
| Gel like insectifugal-insecticidal-fungicidal composition (1) | 100 | 100 | 100 |
| Insectifugal-insecticidal-composition for comparison (1) | 100 | 97 | 94 |

TABLE 9

| Insectifugal-insecticidal-fungicidal composition | Fungicidal effect (%) |
|---|---|
| Gel like insectifugal-insecticidal-fungicidal composition (2) | ○ |
| Insectifugal-insecticidal-composion for comparison (2) | X |

EXAMPLE 27

A fish-luring agent composition (1) was obtained by keeping the cross-linked polymer (8) obtained in Example 22 immersed in cod-liver oil at normal room temperature for seven days so as to be swelled therewith. This fish-luring agent composition (1) had a cod-fish oil content of 88.1% by weight.

Control 18

A fish-luring agent composition for comparison (1) was obtained by keeping the cross-linked polymer for comparison (8) of Control 15 immersed in cod-liver oil at normal room temperature for seven days. During this immersion, however, the cross-linked polymer for comparison (8) was not conspicuously swelled. The fish-luring agent composition for comparison (1) had a cod-liver oil content of 5.2% by weight.

Control 19

A cross-linked polymer for comparison (9) was obtained by following the procedure of Example 27, except that the use of the cross-linkable monomer (B) was omitted. When the cross-linked polymer for comparison (9) was kept immersed in cod-liver oil at normal room temperature for seven days, the cross-linked polymer for comparison (9) was dissolved in the cod-liver oil and formed no gelled mass.

EXAMPLE 28 (TEST FOR FISH-LURING EFFECT)

Samples cut in a fixed size of 20 g severally from the fish-luring agent composition (1) and the fish-luring agent composition for comparison (1) obtained respectively in Example 27 and Control 18 were placed one each in bowls made of metallic net. The bowls were suspended from a fishing line and immersed in one corner of a water tank containing 15 young yellowtails (15 to 20 cm) and 200 liters of sea water. The fish-luring effects of the samples were evaluated on the basis of the number of young fishes lured by the samples. The results are shown in Tables 10.

EXAMPLE 29 (TEST FOR ABILITY TO RETAIN FISH-LURING EFFECT)

The metallic-net bowls packed with the fish-luring agent compositions used in Example 28 were immersed for 24 hours in a water tank containing only 200 liters of sea water. Then, the samples in the bowls were tested for fish-luring effect by following the procedure of Example 28. The results are shown in Table 10.

TABLE 10

| Fish-luring agent composition | Fish-luring effect | Ability to retain fish-luring effect |
|---|---|---|
| Fish-luring agent composition (1) | 15 | 14 |
| Fish-luring agent composition for comparison (1) | 10 | 0 |

EXAMPLE 30

A solid fuel composition (1) was produced by keeping the cross-linked polymer (6) obtained in Example 18 immersed in kerosene (calorific value about 11,000 cal/g) at normal room temperature for seven days so as to be swelled therewith. The solid fuel composition (1) had a kerosene content of 93.5% by weight.

Control 20

A cross-linked polymer for comparison (11) was produced by following the procedure of Example 18, except that the amount of dodecyl acrylate was changed to 87.591 parts and that of ethylene glycol diacrylate to 12.409 parts respectively.

A solid fuel composition for comparison (1) was produced by keeping the cross-linked polymer for comparison (11) immersed in kerosene (calorific value about 11,000 cal/g) at normal room temperature for seven days so as to be swelled therewith. During this immersion, however, the cross-linked polymer for comparison (11) was not conspicuously swelled. This solid fuel composition for comparison (1) had a kerosene content of 21.3% by weight.

Control 21

Into a flask having an inner volume of 500 ml and provided with a thermometer, a stirrer, and a reflux condenser, 10 parts of sodium stearate as a gelling agent and 90 parts of methanol (calorific value about 5,500 cal/g) as a fuel component were charged respectively, the mixture was stirred at a temperature of 60° C. for 15 minutes and then was cooled to obtain a solid fuel composition for comparison (2).

EXAMPLE 31

Samples taken in a fixed size of 20 g severally from the solid fuel composition (1) and the solid fuel compositions for comparison (1) and (2) obtained respectively in Examples 30 and Controls 20 and 21 were placed one each in petri dishes made of aluminum and having a diameter of 6 cm and then ignited at normal room temperature. The combustions of the samples were clocked as to duration and, at the same time, examined visually as to appearance.

The results of the test are shown in Table 11.

TABLE 11

| Solid fuel composition | Ignition time (sec) | Appearance during ignition |
|---|---|---|
| Solid fuel composition (1) | 1070 | Solid was retained |
| Solid fuel composition for comparison (1) | 250 | Solid was retained |
| Solid fuel composition for comparison (2) | 520 | Solid was flowed |

EXAMPLE 32

In a vat having an inner volume of 1.9 liters and made of stainless steel, a solution comprising of 99.823 parts of dodecyl acrylate as monomer (A), 0.177 part of ethylene glycol diacrylate as cross-linkable monomer (B), and 0.5 part of benzoyl peroxide as a polymerization initiator was placed.

A cut piece, 20 cm × 15 cm in surface area, of non-woven polypropylene fabric (basis weight 200 g/m$^2$ and bulk density 0.1 g/cm$^3$) was immersed in the solution, pulled out of the solution, and wrung with a simple roller. Thereafter, the non-woven polypropylene fabric wetted with the monomer solution was placed in a hot air drier kept at 80° C. in an atmosphere of nitrogen, heated at 80° C. for two hours, and then heated further to 90° C. and kept at this temperature for two hours to effect polymerization of the monomer components. Consequently, an oil-absorbent material (1) of this invention having the resultant cross-linked polymer (9) deposited on the non-woven polypropylene fabric was obtained. The amount of the cross-linked polymer (9) deposited in this case on the non-woven polypropylene fabric was 100 parts based on 100 parts of the non-woven fabric.

EXAMPLE 33

An oil-absorbent material (2) was produced by following the procedure of Example 32, except that non-woven polyester fabric (basis weight 200 g/m$^2$ and bulk density 0.1 g/cm³) was used in the place of the non-woven polypropylene fabric and the amount of the cross-linked polymer (9) deposited on the non-woven fabric was changed to 200 parts based on 100 parts of the non-woven fabric.

EXAMPLE 34

On a cut piece, 20 cm×15 cm in surface area, of non-woven nylon fabric (basis weight 200 g/m² and bulk density 0.1 g/cm3), a solution comprising of 99.823 parts of dodecyl acrylate as monomer (A), 0.177 part of ethylene glycol diacrylate as cross-linkable monomer (B), and benzoyl peroxide as a polymerization initiator was uniformly sprayed by the use of a spray.

Then, an oil-absorbent material (3) was produced by placing the non-woven nylon fabric wetted with the monomer solution in a hot air drier kept at 80° C. in an atmosphere of nitrogen, heating the non-woven fabric at 80° C. for two hours, and subsequently heating it further to 90° C. and keeping it at this temperature for two hours to effect polymerization of the monomer components. The amount of the cross-linked polymer (10) deposited in this case on the non-woven nylon fabric was 50 parts based on 100 parts of the non-woven fabric.

EXAMPLE 35

In a flask having an inner volume of 500 ml and provided with a thermometer, a stirrer, a gas inlet pipe, and a reflux condenser, a solution of 3 parts of Softanol 90 (trademark designation of an ethylene oxide adduct of secondary alcohol of 12 to 14 carbon atoms produced by Nippon Shokubai Kagaku Kogyo Co., Ltd.) in 300 parts of water was placed, stirred while the gas phase of the flask interior was displaced with nitrogen, and heated to 40° C. as kept covered with a current of nitrogen. Then, a solution comprising 99.823 parts of dodecyl acrylate as monomer (A), 0.177 part of ethylene glycol diacrylate as cross-linkable monomer (B), and 0.5 part of benzoyl peroxide as a polymerization initiator was added at once to the flask interior. The resultant mixture was vigorously stirred at 500 rpm.

Then, the flask interior was heated to 80° C. and kept at this temperature for two hours to effect polymerization of the monomer components and further heated to 90° C. and kept at this temperature for two hours to complete the polymerization, to obtain an aqueous suspension of a cross-linked polymer (11) having particle diameters of 1 to 100 μm (resin content of suspension 25% by weight).

An oil-absorbent material (4) was produced by uniformly spraying 12 g of the aqueous suspension of the cross-linked polymer (11) on a cut piece, 20 cm × 15 cm in surface area, of a non-woven polypropylene fabric (basis weight 200 g/m² and bulk density 0.03 g/cm³) by the use of a spray and then drying the wet non-woven fabric. The amount of the cross-linked polymer (11) deposited in this case on the non-woven polypropylene fabric was 50 parts based on 100 parts of the non-woven fabric.

Control 22

An oil-absorbent material for comparison (1) was produced by following the procedure of Example 32, except that 89.820 parts of dodecyl acrylate was used as monomer (A) and 10.180 parts of ethylene glycol diacrylate was used as cross-linkable monomer (B) instead. The amount of the cross-linked polymer deposited in this case on the non-woven polypropylene fabric was 100 parts based on 100 parts of the non-woven fabric.

Control 23

An oil-absorbent material for comparison (2) was produced by following the procedure of Example 32, except that 39.854 parts of dodecyl acrylate and 59.780 parts of methacrylic acid were used as monomer (A) and 0.366 part of ethylene glycol diacrylate was used as cross-linkable monomer (B) instead. The amount of the cross-linked polymer deposited in this case on the non-woven polypropylene fabric was 100 parts based on 100 parts of the non-woven fabric.

Control 24

An oil-absorbent material for comparison (3) was produced by following the procedure of Example 32, except that the use of ethylene glycol diacrylate as cross-linkable monomer (B) was omitted. The amount of the polymer deposited in this case on the non-woven polypropylene fabric was 100 parts based on 100 parts of the non-woven polypropylene fabric.

EXAMPLE 36 (TEST FOR OIL-ABSORBING PROPERTY)

Samples cut in a fixed surface area of 10 cm × 10 cm severally from the oil-absorbent materials (1) to (4) obtained in Examples 32 to 35, the oil-absorbent materials for comparison (1) to (3) obtained in Controls 22 to 24, and the same non-woven polypropylene fabric as used in Example 32 were immersed in kerosene or spindle oil at 20° C. After 24 hours' standing in the oil, the samples were taken out of the oil, left suspended in the air for 30 minutes from a clip in order for the oil loosely adhering to the samples to flow down thoroughly, and weighed. The amounts of oil retained (absorbed) finally in the samples were calculated in accordance with the following formula.

Amount of oil absorbed (g) = Weight of sample after absorption of oil − weight of sample before immersion The results are shown in Table 12.

EXAMPLE 37 (TEST FOR OIL RETAINING PROPERTY)

The samples which had absorbed oil in Example 36 were placed on a 200-mesh metallic net and left standing under a load of 10 kg/cm² for one minute. The amounts of oil which flowed out of the samples during the standing were measured. The ratios of oil retention after application of the load were calculated in accordance with the following formula.

Ratio of oil retention (%) = [(Amount of absorbed oil − amount of released oil)/Amount of absorbed oil] × 100

The results are shown in Table 12.

TABLE 12

| Oil-absorbent material | Oil-absorbing property | | Oil-retaining property | |
|---|---|---|---|---|
| | kerosine | spindle oil | kerosine | spindle oil |
| Oil-absorbent material (1) | 19.3 | 18.2 | 96.1 | 93.1 |
| Oil-absorbent material (2) | 18.6 | 17.7 | 97.1 | 96.5 |
| Oil-absorbent material (3) | 18.1 | 17.6 | 80.1 | 75.1 |
| Oil-absorbent material (4) | 18.2 | 17.5 | 80.0 | 76.3 |
| Oil-absorbent material for comparison (1) | 7.2 | 8.6 | 45.3 | 40.5 |

TABLE 12-continued

| Oil-absorbent material | Oil-absorbing property | | Oil-retaining property | |
|---|---|---|---|---|
| | kerosine | spindle oil | kerosine | spindle oil |
| Oil-absorbent material for comparison (2) | 4.5 | 4.7 | 25.6 | 33.1 |
| Oil-absorbent material for comparison (3) | 13.5 | 12.1 | 39.3 | 45.7 |
| Polypropylene non-woven fabric | 5.3 | 6.5 | 24.1 | 27.5 |

EXAMPLE 38 (TEST FOR RECOVERY OF FLOATING OIL)

In a water tank having an inner volume of 36 liters, 30 liters of water was placed (surface area of water top 1,350 cm$^2$) and 15 g of grade A heavy oil was superposed on the water top. Samples cut in a fixed surface area of 10 cm × 10 cm severally from the oil-absorbent materials (1) to (4) obtained in Examples 32 to 35, the oil-absorbent materials for comparison (1) to (3) obtained in Controls 22 to 24, and the same non-woven polypropylene fabric as used in Example 32 were left floating on the water top for four hours and then removed from the water top. The ability of sample for recovery of floating oil was evaluated in accordance with the following scale, based on the state of residue of heavy oil on the water top. The results are shown in Table 13.

○: Complete absence of residual heavy oil on water top

Δ: Slight presence of residual heavy oil on water top

X: Conspicuous presence of residual heavy oil on water top

TABLE 13

| Oil-absorbent material | Recovery of floating oil |
|---|---|
| Oil-absorbent material (1) | ○ |
| Oil-absorbent material (2) | ○ |
| Oil-absorbent material (3) | ○ |
| Oil-absorbent material (4) | ○ |
| Oil-absorbent material for comparison (1) | x |
| Oil-absorbent material for comparison (2) | x |
| Oil-absorbent material for comparison (3) | Δ |
| Polypropylene non-woven fabric | x |

EXAMPLE 39

An oil mist filter (1) was produced by following the procedure of Example 32. The amount of the cross-linked polymer (9) deposited in this case on the non-woven polypropylene fabric was 20 parts based on 100 parts of the non-woven fabric.

EXAMPLE 40

An oil mist filter (2) was produced by following the procedure of Example 33. The amount of the cross-linked polymer (9) on the non-woven polyester fabric was 40 parts based on 100 parts of the non-woven fabric.

EXAMPLE 41

An oil mist filter (3) was produced by following the procedure of Example 34. The amount of the cross-linked polymer (10) on the non-woven nylon fabric was 10 parts based on 100 parts of the non-woven fabric.

EXAMPLE 42

An oil mist filter (4) was produced by following the procedure of Example 35. The amount of the cross-linked polymer (11) on the non-woven polypropylene fabric was 100 parts based on 100 parts of the non-woven fabric.

Control 25

An oil mist filter for comparison (1) was obtained by following the procedure of Control 22. The amount of the cross-linked polymer deposited in this case on the non-woven polypropylene fabric was 20 parts based on 100 parts of the fabric.

Control 26

An oil mist filter for comparison (2) was obtained by following the procedure of Control 23. The amount of the cross-linked monomer deposited in this case on the non-woven polypropylene fabric was 20 parts based on 100 parts of the fabric.

Control 27

An oil mist filter for comparison (3) was obtained by following the procedure of Control 24. The amount of the cross-linked polymer deposited in this case on the non-woven polypropylene fabric was 20 parts based on 100 parts of the fabric.

EXAMPLE 43 (TEST FOR OIL MIST RECOVERY)

The oil mist filters (1) to (4) obtained in Examples 39 to 42, the oil mist filters for comparison (1) to (3) obtained in Controls 25 to 27, and the same non-woven polypropylene fabric as used in Example 39 were each nipped between wooden frames measuring 20 cm × 15 cm in overall surface area and 1 cm in width and set upright. Then, from a distance of 10 cm, spindle oil was sprayed onto the filters a total of ten times with intervals of 30 minutes by the use of a spray. One round of spray consumed 0.5 g of the spindle oil. After the last round of spray, the filters were removed from the wooden frames, left hanging down in the air for one hour from a clip in order for the oil loosely adhering to the filters to flow down thoroughly, and weighed. The ratios of oil mist recovery were calculated in accordance with the following formula.

Ratio of oil mist recovery (%) = [(Weight of filter after spraying of spindle oil − weight of filter before the spraying) /5] × 100

The results are shown in Table 14.

EXAMPLE 44 (TEST FOR EVALUATION OF VISCOUSNESS)

The oil mist filters sprayed with the spindle oil in Example 43 were examined by touch as to viscousness of filter surface. The viscousness was evaluated by the following scale.

○: Dry surface

Δ: Wetness of oil perceivable

X: Heavy viscousness of oil perceived

The results are shown in Table 14.

TABLE 14

| Oil mist filter | Recovery ratio of oil mist (%) | Touch as to viscousness |
|---|---|---|
| Oil mist filter (1) | 98.1 | o |
| Oil mist filter (2) | 98.2 | o |
| Oil mist filter (3) | 80.4 | o |
| Oil mist filter (4) | 98.5 | o |
| Oil mist filter for comparision (1) | 60.2 | Δ |
| Oil mist filter for comparision (2) | 59.4 | x |
| Oil mist filter for comparision (3) | 65.8 | x |
| Polypropylene non-woven fabric | 51.4 | x |

EXAMPLE 45

In a flask having an inner volume of 500 ml and provided with a thermometer, a stirrer, a gas inlet pipe, two dropping funnels, and a reflux condenser, 3 parts of polyethylene glycol (polymerization degree 17) monononylphenyl ether and 100 parts of water were placed, stirred at 300 rpm while the gas phase of the flask interior was displaced with nitrogen, and heated to 70° C. as kept covered with a current of nitrogen.

Separately, in an aqueous solution of 3 parts of polyethylene glycol (polymerization degree 17) monononylphenyl ether in 150 parts of water, a monomer mixture comprising 99.823 parts of dodecyl acrylate as monomer (A) and 0.177 part of ethylene glycol diacrylate as cross-linkable monomer (B) was mixed by the use of a homogenizer at 5,000 rpm for 10 minutes, to prepare 253 parts of an aqueous dispersion of polymer. Further, 1 part of sodium persulfate was dissolved in 50 parts of water, to prepare 51 parts of an aqueous solution of polymerization initiator. The aqueous dispersion of monomer and the aqueous solution of polymerization initiator were placed in the two separate dropping funnels. First, 50 parts of the aqueous dispersion of monomer and 5 parts of the aqueous solution of polymerization initiator were transferred into the flask to initiate polymerization of the monomer components. Thereafter, the remaining aqueous dispersion of monomer was added dropwise thereto over a period of 120 minutes and, at the same time, the remaining aqueous sodium persulfate solution was added dropwise thereto over a period of 240 minutes while the flask interior was kept under a current of nitrogen at 70° C. After the dropwise addition was completed, the reaction mixture was kept at 70° C. for 120 minutes to complete the polymerization and produce an aqueous dispersion (resin content 25% by weight) of a cross-linked polymer (12) having an average particle diameter of 0.2 μm.

Then, various thermosensitive coloring layer forming liquids were prepared as follows.

| (1) Preparation of liquid A | |
|---|---|
| 3,3'-Bis(p-dimethylaminophenyl)-6-dimethyl-aminophthalide | 20 parts |
| Polyvinyl alcohol | 5 parts |
| Water | 75 parts |

These components were mixed and the resultant mixture was pulverized by the use of a sand mill into particles 1 to 5 μm in diameter.

| (2) Preparation of liquid B | |
|---|---|
| Bisphenol A | 20 parts |
| Polyvinyl alcohol | 7.5 parts |
| Water | 72.5 parts |

These components were mixed and the resultant mixture was pulverized by the use of a sand mill into particles 1 to 5 μm in diameter.

| (3) Preparation of liquid C | |
|---|---|
| Calcium carbonate | 20 parts |
| Polyvinyl alcohol | 5 parts |
| Water | 75 parts |

These components were uniformly dispersed by the use of a stirrer.

| (4) Preparation of liquid D | |
|---|---|
| Stearic acid amide | 25 parts |
| Polyvinyl alcohol | 5 parts |
| Water | 70 parts |

These components were uniformly mixed and dissolved by the use of a stirrer.

The aforementioned liquids A to D and the aqueous dispersion of cross-linked polymer (12) were mixed in an A:B:C:D:aqueous dispersion of cross-linked polymer (12) gravimetric ratio of 10:40:5:25:20. The resultant mixture was uniformly applied at a rate of 7 g/m² to quality paper by the use of a bar coater and the applied layer of the mixture was dried at normal room temperature, to obtain a thermosensitive recording material (1).

EXAMPLE 46

Various thermosensitive coloring layer forming liquids were prepared as follows.

| (1) Preparation of liquid E | |
|---|---|
| Ferric stearate | 20 parts |
| Polyvinyl alcohol | 5 parts |
| Water | 75 parts |

These components were mixed and the resultant mixture was pulverized by the use of a sand mill into particles 1 to 5 μm in diameter.

| (2) Preparation of liquid F | |
|---|---|
| Gallic acid | 20 parts |
| Polyvinyl alcohol | 5 parts |
| Water | 75 parts |

These components were mixed and the resultant mixture was pulverized by the use of a sand mill into particles 1 to 5 μm in diameter.

| (3) Preparation of liquid G | |
|---|---|
| Calcium carbonate | 3.333 parts |
| Stearic acid amide | 5.334 parts |
| Polyvinyl alcohol | 8.333 parts |
| Water | 83 parts |

These components were uniformly mixed and dissolved by the use of a stirrer.

The aforementioned liquids E to G and the aqueous dispersion of cross-linked polymer (12) obtained in Example 45 were mixed in an E:F:G:aqueous dispersion of cross-linked polymer (12) gravimetric ratio of 40:10:30:20. The resultant mixture was uniformly applied at a rate of 7 g/m$^2$ on quality paper by the use of a bar coater and the applied layer of the mixture was dried at normal room temperature, to obtain a photosensitive recording material (2).

EXAMPLE 47

The aqueous dispersion of cross-linked polymer (12) (resin content 25% by weight) obtained in Example 45 was uniformly applied at a rate of 2 g/m$^2$ to quality paper by the use of a bar coater and the applied layer of the aqueous dispersion was dried at 60° C. Then, a mixture prepared by mixing the aqueous dispersions A to D obtained in Example 45 in an A:B:C:D gravimetric ratio of 10:40:5:25 was uniformed applied at a rate of 5 g/m$^2$ to the aforementioned dried layer by the use of a bar coater and the superposed layer of the mixture was dried at normal room temperature, to obtain a thermosensitive recording material (3).

Control 28

A thermosensitive recording material for comparison (1) was produced by following the procedure of Example 45, except that 84.956 parts of dodecyl acrylate was used as monomer (A) and 15.044 parts of ethylene glycol diacrylate was used as cross-linkable monomer (B) instead.

Control 29

A thermosensitive recording material for comparison (2) was produced by following the procedure of Example 45, except that 39.854 parts of dodecyl acrylate and 59.780 parts of methacrylic acid were used as monomer (A) and 0.366 part of ethylene glycol diacrylate was used as cross-linkable monomer (B) instead.

Control 30

A thermosensitive recording material for comparison (3) was produced by following the procedure of Example 45, except that 100 parts of dodecyl acrylate was used as monomer (A) and the use of ethylene glycol diacrylate as cross-linking monomer (B) was omitted.

Control 31

A thermosensitive recording material for comparison (4) was produced by mixing the liquids A to D prepared in Example 45 in an A:B:C:D gravimetric ratio of 10:40:5:25, applying the resultant mixture uniformly at a rate of 7 g/m$^2$ to the same quality paper as used in Example 50 by the use of a bar coater, and drying the applied layer of the mixture at normal room temperature.

EXAMPLE 48

On the thermosensitive recording materials (1) to (3) obtained in Examples 45 to 47 and the thermosensitive recording materials for comparison (1) to (4) obtained in Controls 28 to 31, letters of printing types were continuously recorded by the use of Chromatopack (Shimadzu CR-2A). Then, the thermal head used for the recording was visually examined as to the degree of adhesion of dirt thereto. The ability of thermosensitive recording material to prevent adhesion of dirt to the thermal head was evaluated on the following scale. The results are shown in Table 15.

○: Absolutely no discernible adhesion of dirt

Δ: Slightly discernible adhesion of dirt

X: Conspicuous adhesion of dirt

EXAMPLE 49

Rubber stamps to which triolein had been transferred were kept pressed one each against the thermosensitive recording materials to which the letters of print types had been recorded in Example 48. After three days' fast contact with the rubber stampls, the records on the thermosensitive recording materials were visually examined as to the degree of fading or vanishing. The oilproofness was evaluated on the following scale. The results are shown in Table 15.

○: Only slight fading of records

Δ: Conspicuous fading of records

X: Discernible vanishing of records

TABLE 15

| Thermosensitive recording material | Thermal head wasevaluation | Oilproofness |
|---|---|---|
| Thermosensitive recording material (1) | ○ | ○ |
| Thermosensitive recording material (2) | ○ | ○ |
| Thermosensitive recording material (3) | ○ | ○ |
| Thermosensitive recording material for comparison (1) | X | X |
| Thermosensitive recording material for comparison (2) | X | X |
| Thermosensitive recording material for comparison (3) | Δ | Δ |
| Thermosensitive recording material for comparison (4) | X | X |

REFERENTIAL EXAMPLE 1

In a beaker having an inner volume of 100 ml, 12 g of a leuco dye solution prepared by dissolving 3 parts of 3,3-bis-(p-dimethylaminophenyl)-6-dimethylaminophthalide as a color-forming dye in 97 parts of diphenyl methane and 30 g of an aqueous 10 wt % gelatin solution were placed and mixed at 2,000 rpm for five minutes by the use of a homogenizer, to obtain an oil-in-water type emulsion having particle diameters of 1 to 5 μm.

Then, in a flask having an inner volume of 500 ml, the produced emulsion and 30 g of an aqueous 10 wt % gum arabic solution were mixed and heated to 40° C. Further, the emulsion was diluted with 140 ml of warm water at 40° C. and the diluted emulsion was coacervated by having the pH value thereof adjusted to 4.3 by the use of an aqueous 10 wt % acetic acid solution.

Subsequently, the coacervated wall was gelled by being cooled to 5° C., admixed with 1 ml of an aqueous 30 wt % formaldehyde solution, and adjusted to pH 9 by the addition thereto of an aqueous 10 wt % sodium hydroxide solution. Thereafter, the coacervated wall was solidified by being gradually heated to 50° C. and stirred at 50° C. for one hour, to give rise to a dispersion of microcapsules 1 to 20 μm in particle diameter.

The microcapsule dispersion was applied at a rate of 6 g/m² to quality paper by the use of a bar coater and the applied layer of the dispersion was dried in a hot air drier at 60° C. for eight hours. Consequently, there was obtained an upper pressure-sitive recording sheet provided with a layer containing microcapsules which contained the diphenyl methane solution of the color-forming dye.

EXAMPLE 50

In a flask having an inner volume of 500 ml and provided with a thermometer, a stirrer, a gas inlet pipe, two dropping funnels, and a reflux condenser, 3 parts of polyethylene glycol (polymerization degree 17) monononylphenyl ether and 100 parts of water were placed, stirred while the gaseous phase of the flask interior was displaced with nitrogen, and heated to 70° C. as kept covered with a current of nitrogen.

Separately, 253 parts of an aqueous dispersion of monomer was prepared by mixing a monomer mixture comprising 99.823 parts of dodecyl acrylate as monomer (A) and 0.177 part of ethylene glycol diacrylate as cross-linkable monomer (B) in an aqueous solution resulting from dissolution of 3 parts of polyethylene glycol (polymerization degree 17) monononylphenyl ether in 160 parts of water at 5,000 rpm for ten minutes by the use of a homogenizer. Further, 51 parts of an aqueous polymerization initiator solution was prepared by dissolving 1 part of sodium persulfate in 50 parts of water.

The aqueous dispersion of monomer and the aqueous solution of polymerization initiator were placed in the two separate dropping funnels. First, 50 parts of the aqueous dispersion of monomer and 5 parts of the aqueous solution of polymerization initiator were introduced into the flask to initiate polymerization of the monomer components. Thereafter, to the flask interior which was kept at 70° C. under a current of nitrogen, the remaining aqueous dispersion of monomer was added dropwise over a period of 120 minutes and, at the same time, the remaining aqueous solution of sodium persulfate was added dropwise over a period of 240 minutes. After the dropwise addition was completed, the reaction mixture was further kept at 70° C. for 120 minutes to complete the polymerization and obtain an aqueous dispersion (resin content 25% by weight) of cross-linked polymer (13) having an average particle diameter of 0.2 μm.

In an aqueous solution comprising 35 parts of water and 20 parts of polyvinyl alcohol, 20 parts of the aqueous dispersion of the cross-linked polymer (13) and 25 parts of activated clay were uniformly dispersed. The resultant mixed dispersion was uniformly applied at a rate of 10 g/m² to quality paper by the use of a bar coater. Then, the applied layer of the mixed dispersion was dried in a hot air drier at 60° C. for eight hours, to obtain a lower sheet provided with a developing agent layer containing the cross-linked polymer (13).

Then, a pressure-sensitive recording sheet (1) was obtained by superposing the upper sheet obtained in Referential Example 1 and the lower sheet in such a manner that the coated faces thereof were opposed to each other.

Control 32

A pressure-sensitive recording sheet for comparison (1) was obtained by following the procedure of Example 50, except that 84.956 parts of dodecyl acrylate was used as monomer (A) and 15.044 parts of ethylene glycol diacrylate was used as cross-linkable monomer (B) instead.

Control 33

A pressure-sensitive recording sheet for comparison (2) was obtained by following the procedure of Example 50, except that 39.854 parts of dodecyl acrylate and 59.780 parts of methacrylic acid were used as monomer (A) and 0.366 part of ethylene glycol diacrylate was used as cross-linkable monomer (B) instead.

Control 34

A pressure-sensitive recording sheet for comparison (3) was obtained by following the procedure of Example 50, except that 100 parts of dodecyl acrylate was used as monomer (A) instead and the use of ethylene glycol diacrylate as cross-linkable monomer (B) was omitted.

Control 35

A lower sheet provided with a developing agent layer containing no cross-linked polymer was obtained by applying a mixed dispersion comprising 25 parts of activated clay, 55 parts of water, and 20 parts of polyvinyl alcohol at a rate of 10 g/m² to the same quality paper as used in Example 50 by the use of a bar coater and then drying the applied layer of the aqueous dispersion in a hot air drier at 60° C. for eight hours. Then, a pressure-sensitive recording sheet for comparison (4) was obtained by superposing the upper sheet obtained in Referential Example 1 and the lower sheet in such a manner that the coated faces thereof were opposed to each other.

EXAMPLE 51

On the pressure-sensitive recording sheet (1) obtained in Example 50 and the pressure-sensitive recording sheets for comparison (1) to (4) obtained in Controls 32 to 35, letters of 20 different print types were recorded by the use of a typewriter. Then, the upper sheets were removed from the pressure-sensitive recording sheets and the recorded images formed thereon were visually examined as to the clarity of image. This clarity was rated by the following scale. The results are shown in Table 16.

○: Clear recorded image obtained

X: Recorded image blurred and obscured

EXAMPLE 52

Rubber stamps to which triolein had been transferred were kept pressed against the recorded images formed on the recording sheets in Example 51. After three days' fast contact, the recorded images were visually examined as to the degree of blurring or vanishing. The oilproofness was rated in accordance with the following scale. The results are shown in Table 16.

○: Only slight fading of recorded image

Δ: Conspicuous fading of recorded image

X: Discernible vanishing of recorded image

TABLE 16

| Pressure-sensitive recording sheet | Clarity of image | Oilproofness |
|---|---|---|
| Pressure-sensitive recording sheet (1) | ○ | ○ |
| Pressure-sensitive recording sheet for comparison (1) | X | X |
| Pressure-sensitive recording sheet for comparison (2) | X | X |
| Pressure-sensitive recording sheet for comparison (3) | X | Δ |
| Pressure-sensitive recording sheet for comparison (4) | X | X |

EXAMPLE 53

An oil sealing material (1) molded in the shape of a sheet 2 mm in thickness was obtained by kneading 20 parts of the cross-linked polymer (7) obtained in Example 22 with 80 parts of an ethylene-vinyl acetate copolymer at 100° C. for 15 minutes by the use of a roll and pressing the resultant mixture at 100° C.

EXAMPLE 54

An oil sealing material (2) molded in the shape of a sheet 2 mm in thickness was obtained by mixing 18.005 parts of the aqueous dispersion of the cross-linked polymer (3) obtained in Example 10 with 81.995 parts of an aqueous dispersion of styrene-butadiene rubber (resin content 50% by weight) and drying the resultant mixture by heating at 110° C.

EXAMPLE 55

A cross-linked polymer (14) was obtained by following the procedure of Example 22, except that 74.777 parts of dodecyl acrylate and 24.926 parts of hydroxyethyl acrylate were used as monomer (A) and 0.297 part of 1,6-hexane diol diacrylate was used as cross-linkable monomer (B) instead.

An oil sealing material (3) molded in the shape of a sheet 2 mm in thickness was obtained by kneading 20 parts of the produced cross-linked polymer (14) with 80 parts of an ethylene-vinyl acetate copolymer at 100° C. for 15 minutes by the use of a roll and then pressing the resultant blend at 100° C.

Control 36

An oil sealing material for comparison (1) molded in the shape of a sheet 2 mm in thickness was obtained by following the procedure of Example 53, except that the amount of dodecyl acrylate was changed to 73.846 parts and that of ethylene glycol diacrylate to 26.154 parts.

Control 37

An oil sealing material for comparison (2) molded in the shape of a sheet 2 mm in thickness was obtained by following the procedure of Example 53, except that 39.854 parts of dodecyl acrylate and 59,780 parts of methacrylic acid were used in the place of 99.823 parts of dodecyl acrylate and the amount of ethylene glycol diacrylate was changed to 0.366 part.

Control 38

An oil sealing material for comparison (3) molded in the shape of a sheet 2 mm in thickness was obtained by following the procedure of Example 53, except that the use of ethylene glycol diacrylate was omitted.

EXAMPLE 56 (TEST FOR DEGREE OF SWELLING)

Samples taken in a fixed size of 2 g from the oil sealing materials (1) to (3) obtained in Examples 53 to 55 and the oil sealing materials (1) to (3) obtained in Controls 36 to 38 were kept immersed in spindle oil or kerosene for one hour and the swelled samples were pulled out of the oil. The degree of swelling was calculated in accordance with the following formula, using the change in weight before and after the swelling.

Ratio of swelling (%) = {(Weight of sealing material after swelling − weight of sealing material before swelling)/ weight of sealing material before swelling} × 100

The results are shown in Table 17.

EXAMPLE 57 (TEST FOR OIL STOPPING ABILITY)

The oil sealing materials (1) to (3) obtained in Examples 53 to 55 and the oil sealing materials for comparison (1) to (3) obtained in Controls 36 to 38 were each attached under a surface pressure of 200 kg/cm$^2$ to a joint part of a flat blind flange, retained under an inner pressure of 50 kg/cm$^2$ with spindle oil, and visually examined after one hour and five hours of this retention as to the degree of wetting with the spindle oil. The results are shown in Table 17.

TABLE 17

| Oil sealing material | Ratio of swelling (%) | | Oil stopping ability | |
|---|---|---|---|---|
| | spindle oil | kerosene | After 1 hour | After 5 hours |
| Oil sealing material (1) | 286 | 270 | no | no |
| Oil sealing material (2) | 238 | 207 | no | no |
| Oil sealing material (3) | 98 | 77 | no | no |
| Oil sealing material for comparison (1) | 20 | 18 | yes | yes |
| Oil sealing material for comparison (2) | 16 | 12 | yes | yes |
| Oil sealing material for comparison (3) | 253 | 240 | yes | yes |

EXAMPLE 58

An aqueous dispersion of monomer was obtained by mixing an aqueous solution resulting from dissolution of 3 parts of polyethylene glycol (polymerization degree 10) monolauryl ether in 300 parts of water with a solution comprising 99.823 parts of dodecyl acrylate as monomer (A), 0.177 part of ethylene glycol diacrylate as cross-linkable monomer (B), and 0.5 part of 2,2'-azobis-isobutylonitrile at 5,000 rpm for 10 minutes by the use of a homomixer.

Then, in a flask having an inner volume of 500 ml and provided with a thermometer, a stirrer, a gas inlet pipe, and a reflux condenser, the aforementioned aqueous dispersion of the monomer was placed and vigorously stirred at 400 rpm while the gaseous phase of the flask interior was displaced with nitrogen. Subsequently, the flask interior was heated to 70° C. as kept under a current of nitrogen, kept at this temperature for two hours to effect polymerization of the monomer components, and then heated further to 90° C. and kept at this temperature for two hours to complete the polymerization and obtain an aqueous dispersion of a cross-linked polymer (15).

The cross-linked polymer (15) had an average particle diameter of 10 μm. The aqueous dispersion had the cross-linked polymer (15) content of 25.5% by weight.

EXAMPLE 59

In a flask having an inner volume of 500 ml and provided with a thermometer, a stirrer, a gas inlet pipe, two dropping funnels, and a reflux condenser, 3 parts of polyethylene glycol (polymerization degree 17) mononylphenyl ether and 100 parts of water were placed, stirred at 300 rpm while the gaseous phase of the flask interior was displaced with nitrogen, and heated to 70° C. as kept under a current of nitrogen.

Separately, in an atmosphere kept at 70° C. under a current of nitrogen, a monomer mixture comprising 49.519 parts of decyl methacrylate and 49.519 parts of hexadecyl methacrylate as monomer (A) and 0.962 part of hexamethylene dimethacrylate as cross-linkable monomer (B) was mixed with an aqueous solution resulting from dissolution of 3 parts of polyethylene glycol (polymerization degree 17) mononylphenyl ether in 150 parts of water at 5,000 rpm for ten minutes by the use of a homogenizer, to prepare 253 parts of an aqueous dispersion of monomer. Further, 1 part of sodium persulfate was dissolved in 50 parts of water, to prepare 51 parts of an aqueous solution of a polymerization initiator.

The aqueous dispersion of monomer and the aqueous solution of polymerization initiator were separately placed in the two dropping funnels. First, 50 parts of the aqueous dispersion of monomer and 5 parts of the aqueous solution of polymerization initiator were added at once to the flask to initiate polymerization of the monomer components. Thereafter, the remaining aqueous dispersion of monomer was added dropwise over a period of 120 minutes and, at the same time, the remaining aqueous solution of sodium persulfate was added dropwise over a period of 240 minutes. After the dropwise addition was completed, the flask interior was kept at 70° C. for 120 minutes to complete the polymerization and obtain an aqueous dispersion of a cross-linked polymer (16).

The cross-linked polymer (16) had an average particle diameter of 0.2 μm and the aqueous dispersion had a cross-linked polymer (16) content of 25.3% by weight.

EXAMPLES 60 AND 61

Two species of pulp slurry were obtained by mixing 100 parts of kraft pulp, 5 parts of talc, 1 part of rosin type sizing agent, 0.5 part of aluminum sulfate, and 2 parts (as solids content) severally of the cross-linked polymer (15) and the cross-linked polymer (16) obtained respectively in Examples 58 and 59 in water and adjusting the resultant mixtures to a solid concentration of 0.5% by weight. Papers were obtained by molding the pulp slurry in accordance with the method described in Japanese Industrial Standard (JIS) P-8209 by the use of a handmade paper testing machine. The ability of paper to receive ink was evaluated by the following method. The results are shown in Table 18.

(Method of evaluation)

A print was made on a sample paper by the use of an RI printing machine. The print was visually examined as to the ability of paper to receive ink by a panel of five members. This ability was rated on the four-point scale, i.e. excellent, good, acceptable, and rejectable. The scale for this evaluation was as follows.

Excellent: Dense clear print perfectly free from blurring and fogging

Good: Clear print free from blurring and fogging but not from partial loss of uniformity of density Acceptable: Clear print not free from partial occurrence of blurring and fogging Rejectable: Unclear print of poor density not free from occurrence of blurring and fogging Control 39

A pulp slurry was prepared by following the procedure of Example 60, except that the addition of the cross-linked polymer (15) was omitted. A paper for comparison was obtained by molding the pulp slurry in the same manner as in Example 60. This paper was tested for ability to receive ink by following the procedure of Example 60. The results are shown in Table 18.

EXAMPLES 62 AND 63

Coating solutions having a solids content of 50% by weight were obtained by mixing 80 parts of clay, 20 parts of calcium carbonate, 8 parts (as solids content) of a styrene-butadiene latex, 8 parts of denatured starch, and 5 parts (as solids content) severally of the cross-linked polymers (15) and (16) obtained respectively in Examples 58 and 59 with a prescribed amount of water. Coated papers were produced by applying the coating solutions each at a rate of 10 g/m$^2$ (on one surface) to quality paper and drying the applied layers of coating solution at normal room temperature. The coated papers were tested for ability to receive ink by following the procedure of Example 60. The results are shown in Table 18.

Control 40

A coating solution was prepared by by following the procedure of Example 62, except that the addition of the cross-linked polymer (15) was omitted. A coated paper for comparison was produced in the same manner as in Example 62. This coated paper was tested for ability to receive ink in the same manner as in Example 60. The results are shown in Table 18.

TABLE 18

| | Cross-linked polymer | | Ability to receive ink |
|---|---|---|---|
| Example 60 | Cross-linked polymer (15) | 2 parts | excellent |
| Example 61 | Cross-linked polymer (16) | 2 parts | excellent |
| Control 39 | none use | | rejectable |
| Example 62 | Cross-linked polymer (15) | 5 parts | excellent |
| Example 63 | Cross-linked polymer (16) | 5 parts | excellent |
| Control 40 | none use | | acceptable |

EXAMPLE 64

In a flask having an inner volume of 500 ml and provided with a thermometer, a stirrer, a gas inlet pipe, and a reflux condenser, 3 parts of gelatin and 300 parts of water were placed, stirred while the gaseous phase of the flask interior was displaced with nitrogen, and heated to 40° C. as kept covered with a current of nitrogen. Then, a solution comprising 99.823 parts of dodecyl acrylate as monomer (A), 0.177 parts of ethylene glycol diacrylate as cross-linkable monomer (B), and 0.5 parts of benzoyl peroxide as a polymerization initiator was added at once to the flask interior and vigorously stirred at 400 rpm.

Then, the flask interior was heated to 80° C. and kept at this temperature for two hours to effect polymerization of the monomer components and the flask interior was further heated to 90° C. and kept at this temperature for two hours to complete the polymerization. After the polymerization was completed, a granular product was separated by filtration and then washed with water, to obtain a hydrate (resin content 70% by weight) of a cross-linked polymer (17) having particle diameters of 100 to 1,000 μm.

A bag, 10 cm × 7.5 cm in surface area, made of a non-woven polypropylene fabric (basis weight 50 g/m$^2$) was packed with 20 g of the hydrate of the cross-linked polymer (17), sealed by having the mouth thereof thermally fused, then squeezed between rollers to expel excess water therefrom, and dried at 60° C., to obtain an oil-absorbing pack (1).

EXAMPLE 65

An oil-absorbent pack (6) was obtained by packing a bag, 20 ×10 cm in surface area, made of a non-woven polyester fabric (basis weight 50 g/m$^2$) with 20 g of the hydrate of the cross-linked polymer (17) obtained in Example 64, sealing the bag by thermally fusing the mouth thereof, squeezing the bag between rollers to expel excess water therefrom, and drying the bag at 60° C.

Control 41

An oil-absorbent pack for comparison (1) was obtained by following the procedure of Example 64, except that 89.820 parts of dodecyl acrylate was used as monomer (A) and 10.180 parts of ethylene glycol diacrylate was used as cross-linkable monomer (B) instead.

Control 42

An oil-absorbent pack for comparison (2) was obtained by following the procedure of Example 64, except that 39.854 parts of dodecyl acrylate and 59.780 parts of methacrylic acid were used as monomer (A) and 0.366 part of ethylene glycol diacrylate was used as cross-linkable monomer (B) instead.

Control 43

An oil-absorbent pack for comparison (3) was obtained by following the procedure of Example 64, except that 100 parts of dodecyl acrylate was used instead as monomer (A) and the use of a cross-linkable monomer (B) was omitted.

EXAMPLE 66 (TEST FOR OIL-RETAINING PROPERTY)

The oil-absorbent packs (1) and (2) obtained in Examples 64 and 65, the oil-absorbent packs for comparison (1) to (3) obtained in Controls 41 to 43, and a non-woven polypropylene fabric (surface area 10 ×7.5 cm, basis weight 500 g/m$^2$, and bulk density 0.1 g/cc) were each kept immersed in kerosene or spindle oil for 24 hours, pulled out of the oil, and left standing on a 200-mesh metallic net to be drained for one minute. The amounts of oil absorbed were found by weighing. The oil-absorbent materials which had absorbed the oil were placed on a 200-mesh metallic net and kept under a load of 10 kg/cm$^2$ for one minute. The amounts of oil which flowed out of the materials were weighed. The ratios of oil retention were calculated in accordance with the following formula. The results are shown in Table 19.

Ratio of oil retention (g/g) × {(Amount of oil absorbed – amount of oil released)/amount of oil absorbed} × 100

EXAMPLE 67 (TEST FOR RECOVERY OF FLOATING OIL)

In a water tank having an inner volume of 36 liters, 30 liters of water (surface area of water top 1,350 cm$^2$) was placed and 100 g of grade A heavy oil was added to the water top. The all-absorbent packs (1) and (2) obtained in Examples 64 and 65, the oil-absorbent packs for comparison (1) to (3) obtained in Controls 41 to 43, and the non-woven polypropylene fabric (surface area 10×7.5 cm, basis weight 500 g/m$^2$, and bulk density 0.1 g/cc) were each left floating on the water top for four hours and then pulled out of the water top. The ability to recover the floating oil was evaluated in accordance with the following formula. The results are shown in Table 19.

○: Perfect absence of remaining oil

Δ: Presence of small amount of remaining oil

X: Presence of large amount of remaining oil

TABLE 19

| Oil-absorbent material | Oil-retaining property | | Ability to recover the floating oil |
|---|---|---|---|
| | kerosene | spindle oil | |
| Oil-absorbent pack (1) | 91.3 | 87.9 | ○ |
| Oil-absorbent pack (2) | 90.1 | 87.2 | ○ |
| Oil-absorbent pack for comparison (1) | 42.7 | 40.1 | X |
| Oil-absorbent pack for comparison (2) | 16.2 | 19.4 | X |
| Oil-absorbent pack for comparison (3) | 20.1 | 28.8 | X |
| Polypropylene non-woven fabric | X | 18.3 | X |

EXAMPLE 68

In a flask having an inner volume of 500 ml and provided with a thermometer, a stirrer, a gas inlet pipe, and a reflux condenser, 3 parts of gelatin and 300 parts of water were placed, stirred while the gaseous phase of the flask interior was displaced with nitrogen, and heated to 40° C. as kept covered with a current of nitrogen. Then, a solution comprising 99.823 parts of dodecyl acrylate as monomer (A), 0.177 part of ethylene glycol diacrylate as cross-linkable monomer (B), and 0.5 part of benzoyl peroxide as a polymerization initiator was added at once to the flask interior and vigorously stirred at 400 rpm.

Then, the flask interior was heated to 80° C. and kept at this temperature for two hours to effect polymerization of the monomer components and the flask interior was further heated to 90° C. and kept at this temperature for two hours to complete the polymerization. After the polymerization was completed, a granular product was separated by filtration, washed with water, and dried at 60° C., to obtain a cross-linked polymer (18) having particle diameters of 100 to 1,000 μm.

EXAMPLE 69

A cross-linked polymer (19) was obtained by following the procedure of Example 68, except that the amount of dodecyl acrylate was changed to 90.909 parts and 9.091 parts of polypropylene glycol diacrylate (molecular weight 4,000) was used instead as cross-linkable monomer (B).

EXAMPLE 70

A cross-linked polymer (20) was obtained by following the procedure of Example 68, except that 59.908 parts of hexadecyl methacrylate and 39.938 part of butyl methacrylate were used as monomer (A) and 0.154 part of divinyl benzene was used as cross-linkable monomer (B) instead.

Control 44

A polymer for comparison (12) was obtained by following the procedure of Example 68, except that 99.728 parts of hexyl acrylate was used in the place of 99.823 parts of dodecyl acrylate and the amount of ethylene glycol diacrylate was changed to 0.272 part.

Control 45

A polymer for comparison (13) was obtained by following the procedure of Example 68, except that the amount of dodecyl acrylate was changed to 84.956 parts and that of ethylene glycol diacrylate to 15.044 parts respectively.

Control 46

A polymer for comparison (14) was obtained by following the procedure of Example 68, except that 39.831 parts of dodecyl acrylate and 59.746 parts of acrylic acid were used in the place of 99.823 parts of dodecyl acrylate and the amount of ethylene glycol diacrylate was changed to 0.423 part.

EXAMPLE 71 (TEST FOR RECOVERY OF FLOATING OIL BY CONTACT FILTRATION METHOD)

In an Erlenmeyer flask having an inner volume of 300 ml and fitted with a ground stopper, a saturated aqueous solution of trichloroethylene was prepared by stirring 300 ml of purified water and 0.33 g of trichloroethylene for four hours. Then, in this aqueous solution, samples taken in a fixed size of 0.25 g from the cross-linked polymers (18) to (20) obtained in Examples 68 to 70, the polymers for comparison (12) to (14) obtained in Controls 44 to 46, and activated carbon (average particle diameter 1.5 mm and total pore volume 0.8 cm³/g) were each stirred gently with a magnet stirrer held in a constant temperature bath at 25° C. and, after the elapse of ten minutes and one hour, tested for trichloroethylene concentration by gas chromatography. The ratios of removal of oil dissolved in water were calculated in accordance with the following formula. The results are shown in Table 20.

Ratio of removal (%) = {(Dissolved trichloroethylene concentration before addition of absorbent agent) − (dissolved trichloroethylene concentration after addition of absorbent agent)/(dissolved trichloroethylene concentration before addition of absorbing agent} × 100

TABLE 20

| Oil-absorbent agent | Ratio of removal (%) | |
|---|---|---|
| | After 10 mins. | After 1 hour |
| Cross-linked polymer (18) | 56 | 58 |
| Cross-linked polymer (19) | 51 | 53 |
| Cross-linked polymer (20) | 50 | 52 |
| Cross-linked polymer for comparison (12) | 40 | 41 |
| Cross-linked polymer for comparison (13) | 35 | 37 |
| Cross-linked polymer for comparison (14) | 15 | 20 |
| Activated carbon | 30 | 58 |

EXAMPLE 72 (TEST FOR RECOVERY OF DISSOLVED OIL BY FIXED BED METHOD)

Columns of glass 3.5 cm in inside diameter and 30 cm in length were severally packed with samples taken in a fixed size of 60 ml from the cross-linked polymers (18) to (20) obtained in Examples 68 to 70, the polymers for comparison (12) to (14) obtained in Controls 44 to 46, and the same activated carbon as used in Example 71. Into these columns, an aqueous solution containing 500 ppm of trichloroethylene and 1,000 ppm of butanol was delivered upstream by a metering pump at a flow rate of 5 ml/minute (SV 5 mi/ml.hr) and a flow rate of 20 ml/minute (SV 20 ml/ml.hr). The aqueous solution emanating from the column was analyzed for time-course change in trichloroethylene concentration by gas chromatography. The results are shown in Table 21.

TABLE 21

| Oil-absorbent agent | | Concentration of trichloroethylene (ppm) | | | | |
|---|---|---|---|---|---|---|
| | | After 1 day | After 2 days | After 3 days | After 4 days | After 5 days |
| Cross-linked polymer (18) | SV 5 | 0 | 0 | 0 | 0 | 0 |
| Cross-linked polymer (18) | SV 20 | 0 | 0 | 15 | 126 | 208 |
| Cross-linked polymer (19) | SV 5 | 0 | 0 | 0 | 0 | 10 |
| Cross-linked polymer (19) | SV 20 | 0 | 15 | 98 | 201 | 335 |
| Cross-linked polymer (20) | SV 5 | 0 | 0 | 0 | 0 | 0 |
| Cross-linked polymer (20) | SV 20 | 0 | 0 | 72 | 182 | 270 |
| Cross-linked polymer for comparison (12) | SV 5 | 0 | 0 | 0 | 58 | 220 |
| Cross-linked polymer for comparison (12) | SV 20 | 13 | 59 | 282 | 366 | 401 |
| Cross-linked polymer for comparison (13) | SV 5 | 0 | 0 | 71 | 248 | 290 |
| Cross-linked polymer for comparison (13) | SV 20 | 20 | 123 | 311 | 392 | 426 |
| Cross-linked polymer for comparison (14) | SV 5 | 30 | 103 | 210 | 386 | 480 |
| Cross-linked polymer for comparison (14) | SV 20 | 123 | 282 | 394 | 450 | 490 |
| Activated carbon | SV 5 | 0 | 0 | 0 | 0 | 0 |
| Activated carbon | SV 20 | 5 | 186 | 301 | 396 | 408 |

EXAMPLE 73

In a vat of stainless steel having an inner volume of 1.9 liters, a solution consisting of 99.823 parts of dodecyl acrylate as monomer (A), 0.177 part of ethylene glycol diacrylate as cross-linkable monomer (B), and 0.5 part of benzoyl peroxide as a polymerization initiator was placed.

Then, a piece cut in a surface area of 20 cm × 15 cm from non-woven polypropylene fabric (basis weight 150 g/m² and bulk density 0.1 g/cm³) was immersed in the solution, pulled out of the solution, and wrung by the use of a simple roller. The non-woven polypropylene fabric wetted with the monomer solution was placed in a hot air drier kept at 80° C. in an atmosphere of nitrogen, heated at 80° C. for two hours, and then heated further to 90° C. and kept at this temperature for two hours to effect polymerization of the monomer components. A cross-linked polymer (21) formed by the polymerization was carried on the non-woven polypropylene fabric. The gravimetric ratio of the cross-linked polymer (21)/non-woven fabric was 100/100.

The same columns as used in Example 72 were severally packed with the non-woven polypropylene fabric carrying the produced cross-linked polymer (21) and a piece cut in a surface area of 20 cm × 15 cm from the non-woven polypropylene fabric in the unmodified form. To the columns, an aqueous solution containing 500 ppm of trichloroethylene or an aqueous solution containing 500 ppm of toluene was delivered upstream at a flow rate of 5 ml/minute by the use of a metering pump. The aqueous solution emanating from the column was tested for time-course change in trichloroethylene concentration by gas chromatography. The results are shown in Table 22.

density 0.1 g/cm3), a solution consisting of 99.823 parts of dodecyl acrylate as monomer (A), 0.177 part of benzoyl peroxide as cross-linkable monomer (B), and benzoyl peroxide as a polymerization initiator was uniformly sprayed by the use of a spray. The amount of the monomer solution deposited in this case on the non-woven nylon fabric was 50 parts based on 100 parts of the non-woven fabric.

Then, the non-woven nylon fabric having the monomer solution deposited thereon was kept immersed for two hours in a hot water bath kept at 80° C. and bubbled with nitrogen gas, heated further to 90° C., and kept at this temperature for two hours to effect polymerization of the monomer components. The non-woven nylon fabric pulled out of the water bath was dried in a hot air drier at 100° C. for one hour, to obtain an oil-absorbent material (7).

Control 47

An oil-absorbent material for comparison (4) was obtained by following the procedure of Example 74, except

TABLE 22

| | Concentration of trichloroethylene (ppm) | | | | | Concentration of toluene (ppm) | | | | |
|---|---|---|---|---|---|---|---|---|---|---|
| Oil-absorbent agent | After 1 day | After 2 days | After 3 days | After 4 days | After 5 days | After 1 day | After 2 days | After 3 days | After 4 days | After 5 days |
| Cross-linked polymer (21) supported polypropylene non-woven fabrics | 0 | 0 | 0 | 2 | 18 | 0 | 0 | 0 | 24 | 169 |
| Untreated polypropylene non-woven fabric | 450 | 480 | 475 | 476 | 482 | 450 | 495 | 489 | 491 | 490 |

EXAMPLE 74

In a vat of stainless steel having an inner volume of 1.9 liters, a solution comprising 99.823 parts of dodecyl acrylate as monomer (A), 0.177 part of ethylene glycol diacrylate as cross-linkable monomer (B), and 0.5 part of benzoyl peroxide as a polymerization initiator was placed.

Then, a piece cut in a surface area of 20 cm × 15 cm from a non-woven polypropylene fabric (basis weight 200 g/m² and bulk density 0.1 g/cm³) was immersed in the solution, pulled out of the solution, and wrung by the use of a simple roller. The amount of the monomer solution deposited at this time on the non-woven polypropylene fabric was 100 parts based on 100 parts of the non-woven fabric.

Thereafter, the non-woven polypropylene fabric having the polymer solution deposited thereon was kept immersed for two hours in a hot water bath kept at 80° C. and bubbled with nitrogen gas and heated further to 90° C. and kept at this temperature for two hours to effect polymerization of the monomer components. The non-woven polypropylene fabric pulled out of the water bath was dried in a hot air drier at 100° C. for one hour, to obtain an oil-absorbent material (5).

EXAMPLE 75

An oil-absorbent material (6) was obtained by following the procedure of Example 74, except that a non-woven polyester fabric (basis weight 200 g/m² and bulk density 0.1 g/cm³) was used in the place of the non-woven polypropylene fabric. The amount of the monomer solution deposited in this case on the non-woven polyester fabric was 200 parts based on 100 parts of the non-woven fabric.

EXAMPLE 76

On a piece cut in a surface area of 20 cm × 15 cm from a non-woven nylon fabric (basis weight 200 g/m² and bulk that 89.820 parts of dodecyl acrylate was used as monomer (A) and 10.180 parts of ethylene glycol diacrylate was used as cross-linkable monomer (B) instead. The amount of the monomer solution deposited in this case on the non-woven polypropylene fabric was 100 parts based on 100 parts of the non-woven fabric.

Control 48

An oil-absorbent material for comparison (5) was obtained by following the procedure of Example 74, except that 39.854 parts of dodecyl acrylate and 59.780 parts of methacrylic acid were used as monomer (A) and 0.366 part of ethylene glycol diacrylate was used as cross-linkable monomer (B) instead. The amount of the monomer solution deposited in this case on the non-woven polypropylene fabric was 100 parts based on 100 parts of the non-woven fabric.

Control 49

An oil-absorbent material for comparison (6) was obtained by following the procedure of Example 74, except that the use of ethylene glycol diacrylate as cross-linkable monomer (B) was omitted. The amount of the monomer solution deposited in this case on the non-woven polypropylene fabric was 100 parts based on 100 parts of the non-woven fabric.

EXAMPLE 77 (TEST FOR OIL-ABSORBING PROPERTY)

Samples cut in a fixed size of 10 cm × 10 cm from the oil-absorbent materisls (5) to (7) obtained in Examples 74 to 76, the oil-absorbent materials for comparison (4) to (6) obtained in Controls 47 to 49, and the same non-woven polypropylene fabric as used in Example 74 were each immersed in kerosene or spindle oil at 20° C. After 24 hours' immersion in the oil, the samples were pulled out of the oil, nipped by a clip, left suspended in the air for 30 minutes in order for the oil loosely adhering to the sample to flow down thoroughly, and weighed. The amounts of oil retained (absorbed) in the oil-absorbent materials were calculated in accordance with the following formula.

Amount of oil absorbed (g) = Weight of sample after absorption of oil − weight of sample before immersion The results are shown in Table 23.

EXAMPLE 78 (TEST FOR OIL-RETAINING PROPERTY)

The samples which had absorbed oil in Example 77 were placed on a 200-mesh metallic net and kept under a load of 10 kg/cm$^2$ for one minute. The amounts of oil which flowed out of the samples during the application of the load were weighed. The ratios of oil retention after the application of load were calculated in accordance with the following formula.

Ratio of oil retention (%) = {(Amount of oil absorbed − amount of oil released)/amount of oil absorbed} × 100 wherein, the amount of oil absorbed (g) is what is obtained in accordance with the formula given in Example 77.

The results are shown in Table 23.

The results are shown in Table 24.

TABLE 24

| Oil-absorbent material | Recovery of floating oil |
| --- | --- |
| Oil-absorbent material (5) | o |
| Oil-absorbent material (6) | o |
| Oil-absorbent material (7) | o |
| Oil-absorbent material for comparison (4) | X |
| Oil-absorbent material for comparison (5) | X |
| Oil-absorbent material for comparison (6) | Δ |
| Polypropylene non-woven fabric | X |

What is claimed is:

1. A method for improving the aroma in a space comprising placing in said space a gel-like aromatic agent, wherein said gel-like aromatic agent is formed by incorporating an aromatic component composition in an oil-absorbent, swelling cross-linked polymer (P), said polymer being obtained by polymerization of a monomer component (A) comprising 90 to 99.999% by weight of a monomer having as a main moiety thereof an alkyl (meth)acrylate, the alkyl group of which has 10 to 16 carbon atoms and

TABLE 23

| | Oil-absorbing property | | Oil-retaining property | |
| --- | --- | --- | --- | --- |
| Oil-absorbent material | kerosene | spindle oil | kerosene | spindle oil |
| Oil-absorbent material (5) | 19.5 | 18.9 | 97.1 | 94.4 |
| Oil-absorbent material (6) | 18.8 | 17.7 | 96.4 | 96.9 |
| Oil-absorbent material (7) | 19.0 | 17.8 | 83.5 | 82.0 |
| Oil-absorbent material for comparison (4) | 7.5 | 8.9 | 48.9 | 44.1 |
| Oil-absorbent material for comparison (5) | 4.7 | 4.7 | 24.6 | 30.5 |
| Oil-absorbent material for comparison (6) | 14.5 | 12.2 | 43.2 | 44.8 |
| Polypropylene non-woven fabric | 5.3 | 6.5 | 24.1 | 27.5 |

EXAMPLE 79 (TEST FOR RECOVERY OF FLOATING OIL)

In a water tank having an inner volume of 36 liters, 30 liters of water (surface area of water top 1,350 ml) was placed and 15 g of grade A heavy oil was added to the water top. Samples cut in a surface area of 10 cm × 10 cm from the oil-absorbent materials (5) to (7) obtained in Examples 74 to 76, the oil-absorbent materials for comparison (7) to (9) obtained in Controls 47 to 49, and the same non-woven polypropylene fabric as used in Example 77 were left floating on the water top for four hours and pulled out of the water top. The water top was visually examined as to the condition of the residual heavy oil. The ability of the sample to recover the floating oil was evaluated in accordance with the following scale.

: Complete absence of residual heavy oil on water top

Δ: Presence of only a few spots of redidual heavy oil on water top

X: Presence of conspicuous amount of residual heavy oil on water top possessing one polymerizable unsaturated group in the molecular unit thereof, and 0.001 to 10% by weight of a cross-linkable monomer (B) possessing at least two polymerizable unsaturated groups in the molecular unit thereof, such that the total of the amount of the polymerizable monomer and that of the cross-linkable monomer is 100% by weight and polymerization of said swelling cross-linked polymer occurs before said aromatic component is incorporated in said polymer, wherein said aromatic component is a perfume selected from the group consisting of jasmine oil and citric oils.

2. The method according to claim 1, wherein said space is a room or vehicle.

3. The method according to claim 1, wherein said aromatic component is a citric oil selected from the group consisting of lemon oil and lime oil.

4. A method for improving the aroma in a space comprising placing in said space a gel-like aromatic agent, wherein said gel-like aromatic agent is formed by incorporating an aromatic component composition in an oil-absorbent, swelling cross-linked polymer (P), said polymer being obtained by polymerization of a monomer component (A) comprising 90 to 99.999% by weight of a monomer having as a main moiety thereof an alkyl (meth)acrylate, the alkyl group of which has 10 to 16 carbon atoms and possessing one polymerizable unsaturated group in the molecular unit thereof, and 0.001 to 10% by weight of a cross-linkable monomer (B) possessing at least two polymerizable unsaturated groups in the molecular unit thereof, such that the total of the amount of the polymerizable monomer and that of the cross-linkable monomer is 100% by weight and polymerization of said swelling cross-linked polymer occurs before said aromatic component is incorporated in said polymer, wherein said aromatic component is a synthetic perfume.

5. The method according to claim 4, wherein said synthetic perfume is selected from the group consisting of monoterpene hydrocarbons, diterpene hydrocarbons, aromatic hydrocarbons, terpene alcohols, aliphatic aldehydes, terpene aldehydes, aromatic aldehydes terpene ketones, aromatic ketones, alicyclic ketones, macrocyclic ketones, ethers, acetals, carboxylic esters, lactones, heterocyclic compounds and mixtures thereof.

6. The method according to claim 4, wherein said synthetic perfume is selected from the group consisting of limonen; abietene; parathimen; linalool; citronelool; nelol; 1-menthol; benzyl alcohol; α-phenyl ethanol; decanal; citrol; citroneral; lilal; benzaldehyde; cinnamaldehyde; menthone; carbone; p-methyl acetophenone; benzophenone; α, β, γ-ionone; α, β, γ-ilone; muscone; civetone; diphenyl ether; rose oxide; linalool oxide; cytral dimethyl acetal; isocyalacetate; -heptyl butyrolactone; indole; and methyl quinoline.

7. The method according to claim 1, wherein said aromatic component is a perfume alone.

8. The method according to claim 1, wherein said aromatic component comprises a perfume and an oily diluent.

9. The method according to claim 8, wherein said oily diluent is selected from the group consisting of paraffin oils, alcohols, ketones, esters and ethers.

10. The method according to claim 1, wherein said aromatic agent comprises 2 to 40% by weight aromatic component and 60 to 98% by weight cross-linked polymer (P).

11. The method according to claim 1, wherein said aromatic agent further comprises an antioxidant, coloring matter, insecticide or medicine.

12. The method according to claim 1, wherein said aromatic component is incorporated in said polymer by immersing said polymer in the aromatic component at room temperature for sufficient time to cause the cross-linked polymer (P) to absorb the aromatic component.

13. A method for emitting fragrances in a space comprising placing in said space a gel-like aromatic agent, wherein said gel-like aromatic agent is formed by incorporating an aromatic component in a swelling oil-absorbent cross-linked polymer (P) obtained by polymerization of a monomer component (A) comprising 90 to 99.999% by weight of a monomer having as a main moiety thereof an alkyl (meth) acrylate, the alkyl group of which has 10 to 16 carbon atoms and possessing one polymerizable unsaturated group in the molecular unit thereof, and 0.001 to 10% by weight of a cross-linkable monomer (B) possessing at least two polymerizable unsaturated groups in the molecular unit thereof, such that the total of the amount of the polymerizable monomer and that of the cross-linkable monomer is 100% by weight and polymerization of said swelling cross-linked polymer occurs before said aromatic component is incorporated in said polymer.

14. A method for retaining the intensity and tone of an aroma comprising placing in said space a gel-like aromatic agent, wherein said gel-like aromatic agent is formed by incorporating an aromatic component in a swelling oil-absorbent cross-linked polymer (P) obtained by polymerization of a monomer component (A) comprising 90 to 99.999% by weight of a monomer having as a main moiety thereof an alkyl (meth)acrylate, the alkyl group of which has 10 to 16 carbon atoms and possessing one polymerizable unsaturated group in the molecular unit thereof, and 0.001 to 10% by weight of a cross-linkable monomer (B) possessing at least two polymerizable unsaturated groups in the molecular unit thereof, such that the total of the amount of the polymerizable monomer and that of the cross-linkable monomer is 100% by weight and polymerization of said swelling oil-absorbent cross-linked polymer occurs before said aromatic component is incorporated in said polymer.

* * * * *